(12) United States Patent
Semple et al.

(10) Patent No.: US 6,586,405 B2
(45) Date of Patent: Jul. 1, 2003

(54) NON-COVALENT INHIBITORS OF UROKINASE AND BLOOD VESSEL FORMATION

(75) Inventors: Joseph Edward Semple, San Diego, CA (US); Michael I. Weinhouse, Escondido, CA (US); Odile Esther Levy, San Diego, CA (US); Edwin L. Madison, San Diego, CA (US); Amir P. Tamiz, San Diego, CA (US)

(73) Assignee: Corvas International, Inc., San Diego, CA (US)

( * ) Notice: Subject to any disclaimer, the term of this patent is extended or adjusted under 35 U.S.C. 154(b) by 0 days.

(21) Appl. No.: 09/733,645

(22) Filed: Dec. 7, 2000

(65) Prior Publication Data

US 2002/0037857 A1 Mar. 28, 2002

Related U.S. Application Data

(63) Continuation-in-part of application No. 09/637,483, filed on Aug. 11, 2000, now abandoned.

(51) Int. Cl.[7] ................................................. C07K 5/06
(52) U.S. Cl. ............................ 514/19; 514/18; 530/331
(58) Field of Search ....................... 514/18, 19; 530/331

(56) References Cited

U.S. PATENT DOCUMENTS 5,932,567 A    8/1999  Seitz et al. .................. 514/210

FOREIGN PATENT DOCUMENTS

| EP | 0 601 459 A2 | 6/1994 |
|---|---|---|
| EP | 0 669 317 A1 | 8/1995 |
| WO | WO 96/17860 | 6/1996 |
| WO | WO 00/05245 | 2/2000 |
| WO | WO 00/61608 | 10/2000 |
| WO | WO 01/96286 A2 | 12/2001 |
| WO | WO 01/96366 A2 | 12/2001 |

OTHER PUBLICATIONS

Stürzebecher, J., et al., 3–Amidinophenylalanine–based Inhibitors of Urokinase, *Bioorganic & Medicinal Chemistry Letters*, 9:3147–3152 (1999).

Tamura, S.Y., et al., Synthesis and biological activity of peptidyl aldehyde urokinase inhibitors, *Bioorganic & Medicinal Chemistry Letters*, 10:983–987 (2000).

*Primary Examiner*—Christopher S. F. Low
*Assistant Examiner*—David Lukton
(74) *Attorney, Agent, or Firm*—Suzanne L. Biggs; Pillsbury Winthrop LLP

(57) ABSTRACT

Novel compounds having activity as non-covalent inhibitors of urokinase and having activity in reducing or inhibiting blood vessel formation are provided. These compounds have P1 a group having an amidino or guanidino moiety or derivative thereof. These compounds are useful in vitro for monitoring plasminogen activator levels and in vivo in treatment of conditions which are ameliorated by inhibition of or decreased activity of urokinase and in treating pathologic conditions wherein blood vessel formation is related to a pathologic condition.

90 Claims, 17 Drawing Sheets

6-1

*i*

6-2

| Compound | Structure |
|---|---|
| A | 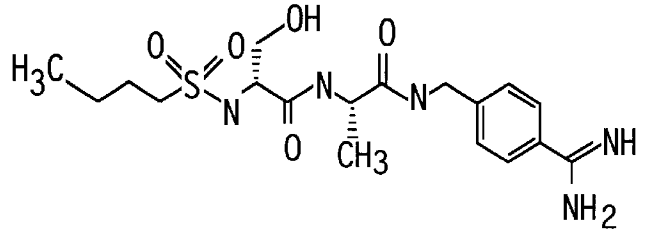 |
| B | 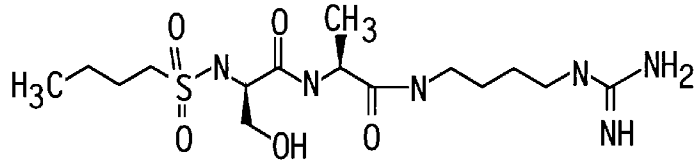 |
| C | 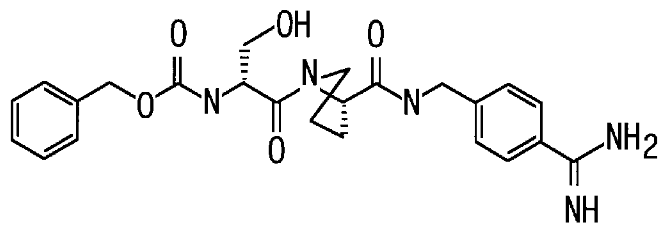 |
| D | 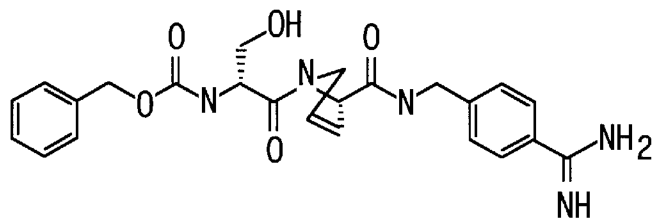 |
| E | 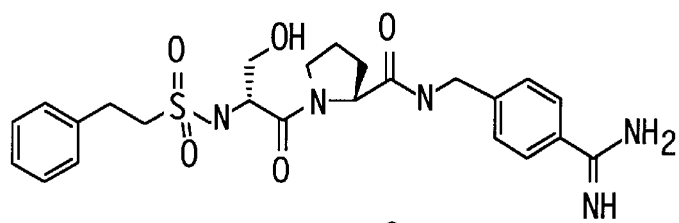 |
| F | 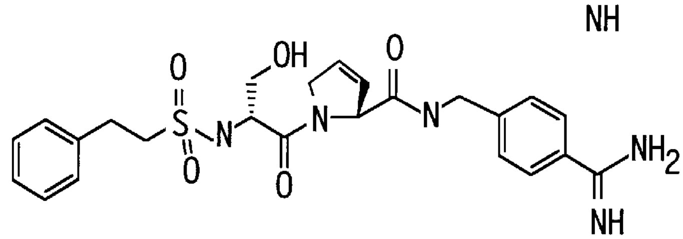 |
| G | 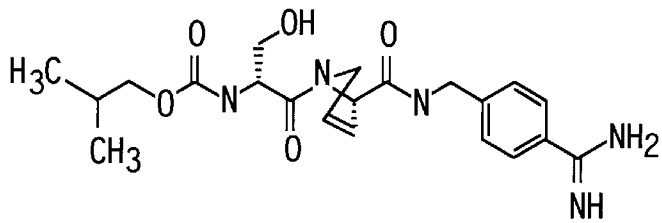 |

| Compound | Structure |
|---|---|
| H | 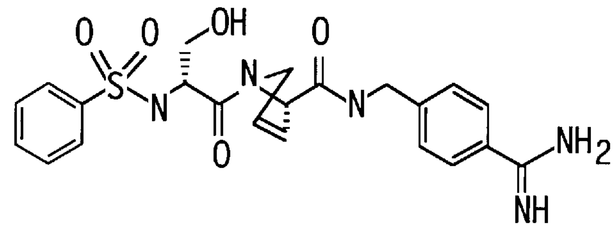 |
| I | 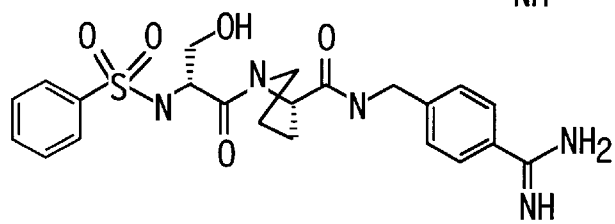 |
| J | 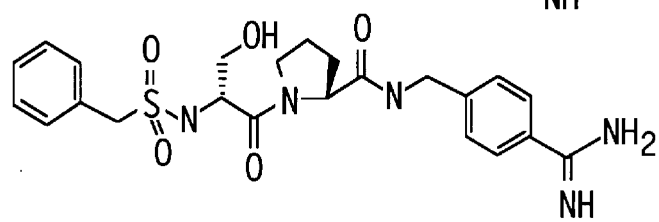 |
| K | 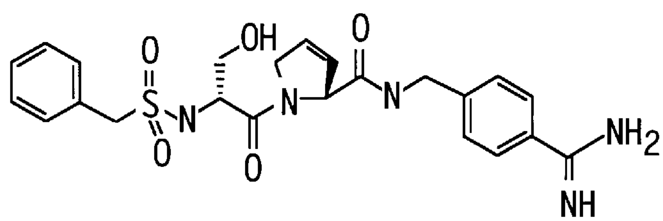 |
| L | 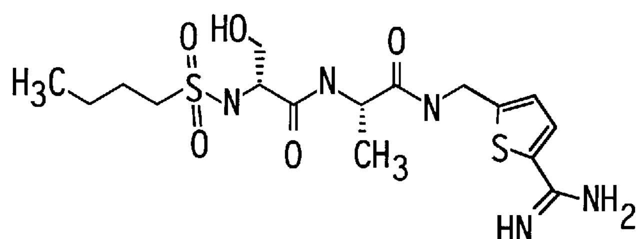 |
| M | 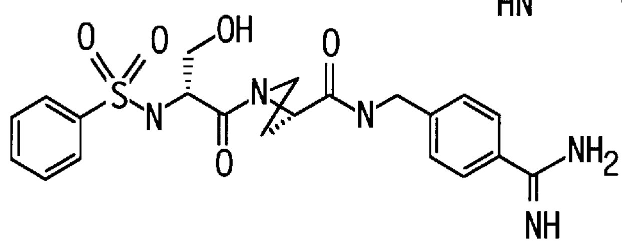 |

| Compound | Structure |
|---|---|
| N | 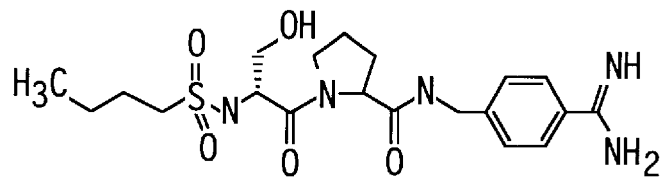 |
| O | 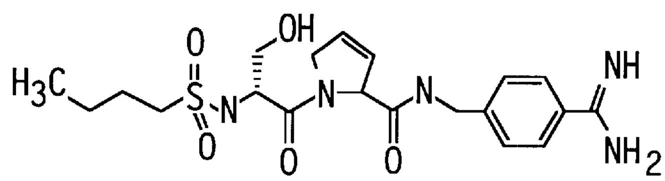 |
| P | 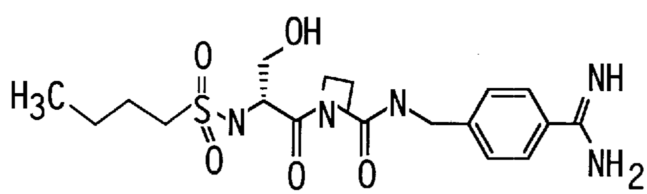 |
| Q | 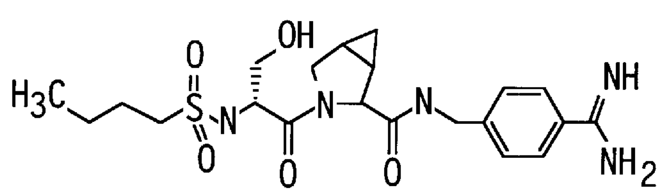 |
| R | 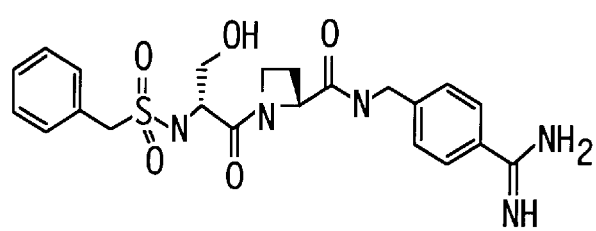 |
| S | 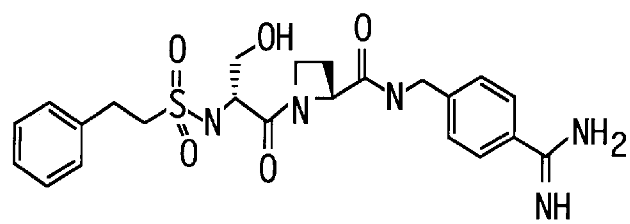 |

| Compound | Structure |
|----------|-----------|
| T | 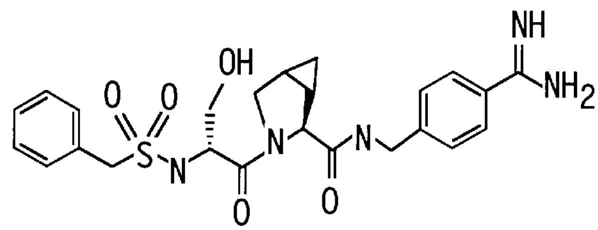 |
| U | 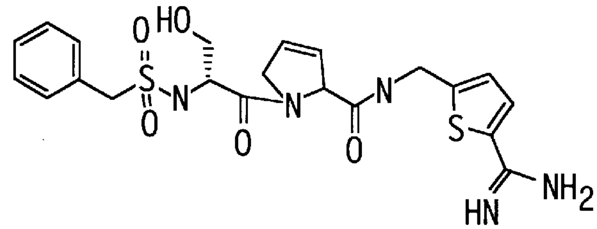 |
| V | 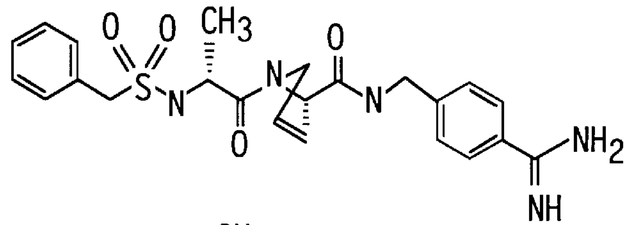 |
| W | 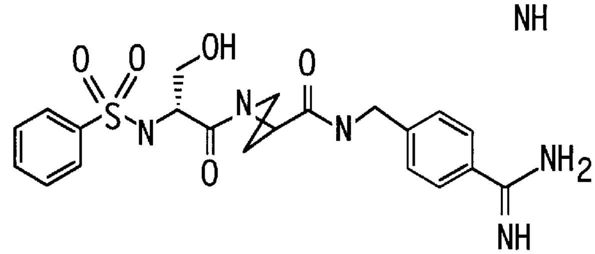 |
| X | 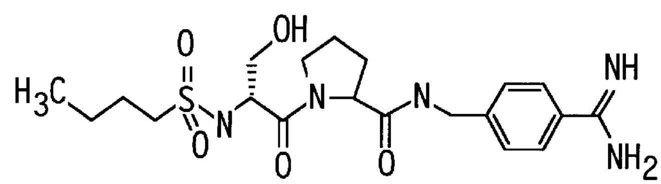 |
| Y | 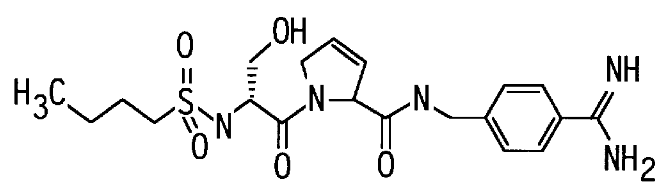 |
| Z | 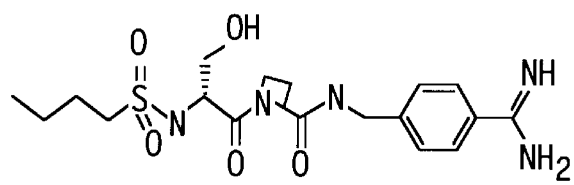 |

| Compound | Structure |
|---|---|
| AA | 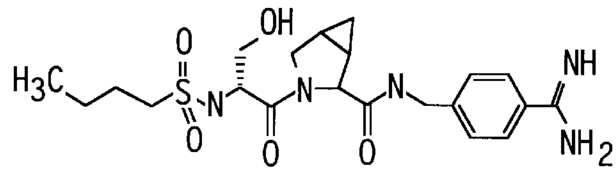 |
| AB | 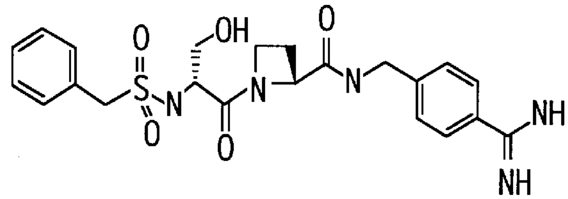 |
| AC | 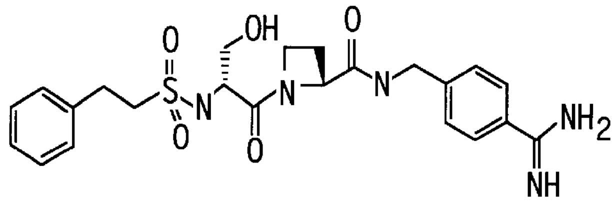 |
| AD | 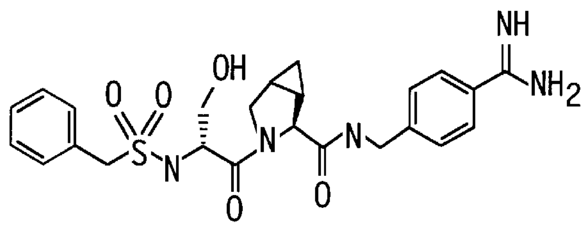 |
| AE | 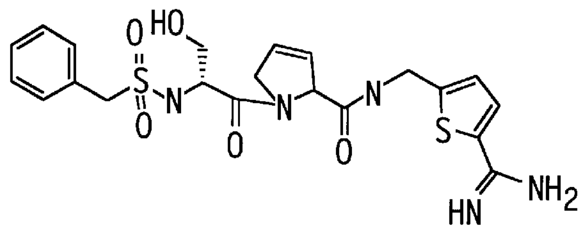 |
| AF | 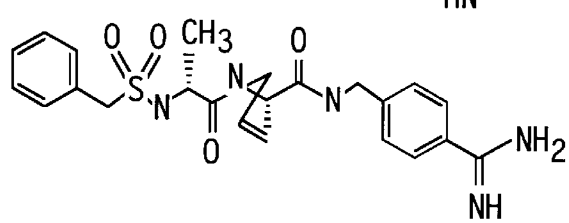 |
| AG | 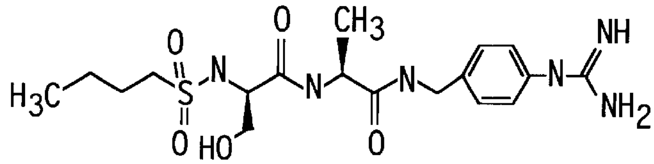 |

FIG. 10E

| Compound | Structure |
|---|---|
| AH | 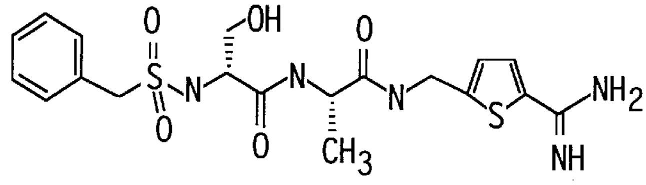 |
| AI | 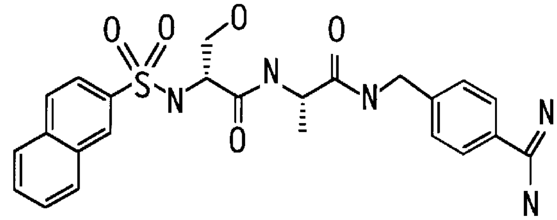 |
| AJ | 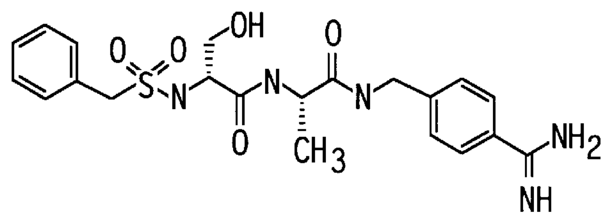 |
| AK | 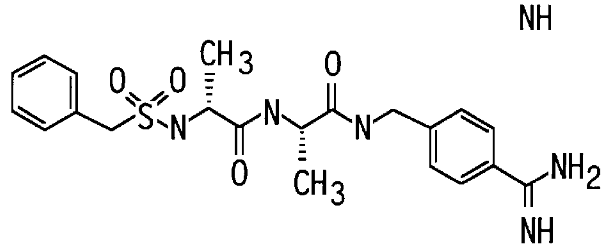 |
| AL | 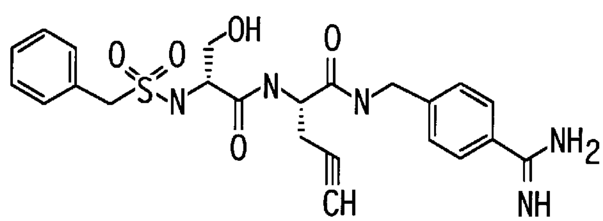 |
| AM | 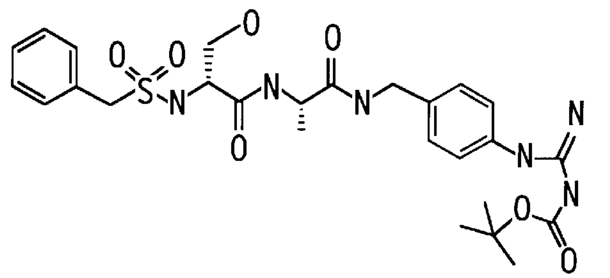 |

FIG. 10F

| Compound | Structure |
|---|---|
| AN | 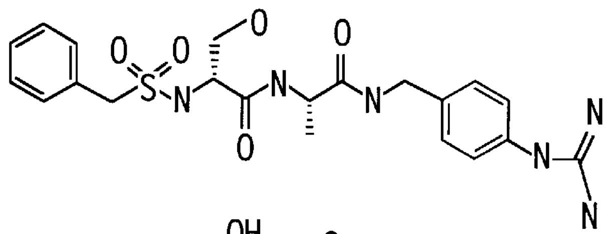 |
| AO | 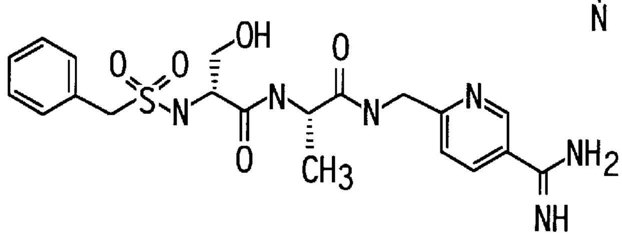 |
| AP | 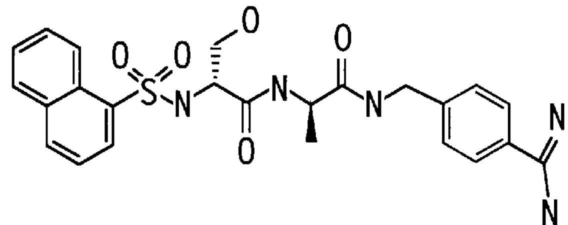 |
| AQ | 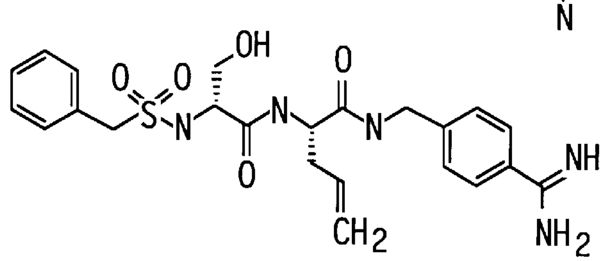 |
| AR | 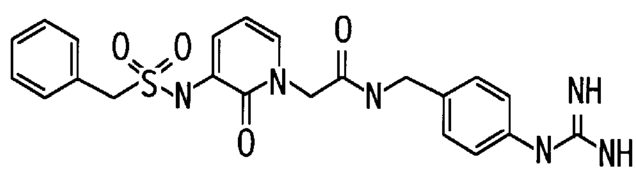 |
| AS | 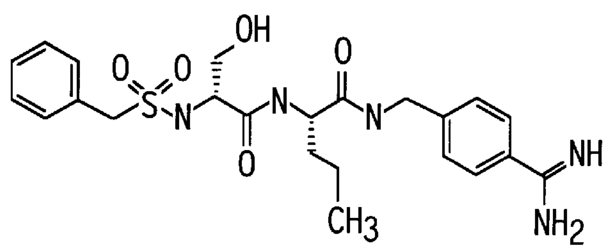 |

FIG. 10G

| Compound | Structure |
|----------|-----------|
| AT | 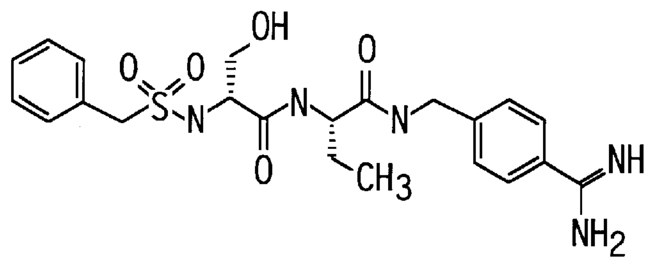 |
| AU | 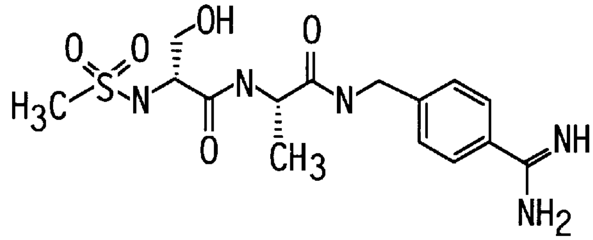 |
| AV | 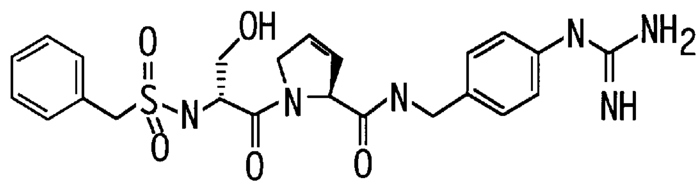 |
| AW | 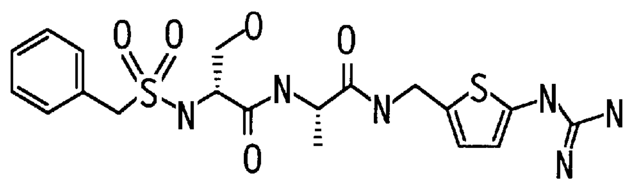 |

FIG. 10H

NON-COVALENT INHIBITORS OF UROKINASE AND BLOOD VESSEL FORMATION

CROSS REFERENCE TO RELATED APPLICATIONS

This application is a continuation-in-part of U.S. Ser. No. 09/637,483, filed Aug. 11, 2000 now abandoned, the disclosures of which is incorporated by reference herein.

FIELD OF THE INVENTION

Urokinase is an enzyme involved in the metastasis of tumor cells, neovascularization, and other activities. One purpose of the present invention is to provide novel compounds which are active as inhibitors of urokinase that can be used to inhibit the activity of urokinase and thereby attenuate its deleterious effects. Another purpose of the present invention is to provide novel compounds which inhibit blood vessel formation, particularly blood vessel formation related to a pathologic condition.

BACKGROUND AND INTRODUCTION TO THE INVENTION

Urinary-type plasminogen activator (uPA; urokinase) is a serine protease within the trypsin/chymotrypsin family. In its physiological state, uPA is found in three forms: single chain pro-uPA, two chain uPA, and low molecular weight uPA (lacks N-terminal domains). The zymogen, pro-uPA, is converted to u-PA by cleavage of the peptide bond at K158-I159. The resultant two chain uPA is linked by disulfide bridges, has an $M_r$ of about 50 kD, and a C-terminal serine proteinase domain.

The activity of uPA is focused to cell surfaces upon binding to its receptor, uPAR. uPAR is a single-chain glycosyl phosphatidyl inositol (GPI)-anchored membrane receptor. The N-terminal 92 amino acids of uPAR play a dominant role in binding to uPA and pro-uPA. Receptor for uPA has been located on T-cells, NK cells, monocytes, and neutrophils, as well as vascular endothelial cells, fibroblasts, smooth muscle cells, keratinocytes, placental trophoblasts, hepatocytes, and a wide variety of tumor cells.

After conversion of pro-uPA to uPA, which occurs primarily at the uPAR on the cell surface, uPA activates plasminogen to plasmin. Activation occurs upon cleavage at residues PGR-VV for human plasminogen, or at residues SGR-IV for bovine plasminogen. Because plasminogen also is present on the cell surface, this activation cascade focuses the activity of u-PA and plasmin on the plasma membrane. Plasmin has many roles, including activation of additional uPA and other enzymes, digestion of fibrin, and digestion of components of the extracellular matrix (ECM). Digestion of the ECM surrounding a tumor removes the ECM as a physical barrier to metastasizing cells, which are then free to leave primary tumors and invade secondary sites. A review of the role of the uPA/uPAR system in cancer metastasis is provided in "The Urokinase-type Plasminogen Activator System in Cancer Metastasis: A Review", Andreasen et al., Int. J. Canc. 72:1–22 (1997).

A correlation between a high level of uPA and a high rate of metastasis, and poor prognosis, has been noted in certain tumors, especially breast cancer [Quax et al., J. Cell Biol. 115:191–199 (1991); Duffy et al., Cancer Res. 50:6827–6829 (1990)]. For instance, tumors of the lung [Oka et al., Cancer Res. 51:3522–3525 (1991)], bladder [Hasui et al., Int. J. Cancer 50:871–873 (1992)], stomach [Nekarda et al., Lancet 343:117 (1994)], cervical cancer [Kobayashi et al., Cancer Res. 54:6539–6548 (1994)], ovary [Kuhn et al., Gynecol. Oncol. 55:401–409 (1994)], kidney [Hofmann et al., Cancer 78:487–492 (1996)], brain [Bindahl et al., J. Neuro-Oncol. 22:101–110 (1994)], and soft tissue sarcoma [Choong et al., Int. J. Cancer (Pred. Oncol.) 69:268–272 (1996)] have exhibited a high level of uPA and/or uPA activity and a high rate of metastases. Overproduction of uPA has been reported to result in increased skeletal metastasis by prostate cancer cells in vivo [Achbarou et al., Cancer Res. 54:2372–2377 (1994)].

Inhibition or lowering of uPA activity, or disruption/inhibition of the interaction between uPA and its receptor (uPAR) has been shown to have a positive effect on maintenance of the extracellular matrix and an inhibitory effect on metastasis [Ossowski and Reich, Cell 35:611–619 (1983); Ossowski, Cell 52:321–328 (1988); Ossowski, J. Cell Biol. 107:2437–2445 (1988); Wilhelm et al., Clin. Exp. Metastasis 13:296–302 (1995); Achbarou et al., Cancer Res. 54:2372–2377 (1994); Crowley et al., Proc. Natl. Acad. Sci. USA 90:5021–5025 (1993); Kook et al., EMBO J. 13:3983–3991 (1994)]. The results of such experimental studies suggest that uPA-catalyzed plasminogen activation is rate-limiting for tumor progression, local tumor invasion and/or formation of distant metastasis. [Andreasen et al., Int. J. Canc. 72:1–22 (1997)].

The effects of the uPA system on cell migration and invasion are thought to be due to both a proteolytic effect of plasmin-mediated degradation of the extracellular matrix, as well as more a direct interaction of the uPA receptor with components of the extracellular matrix. Degradation of the extracellular matrix permits a metastasizing cell to invade the matrix, whereas interaction between uPA receptor and the matrix itself assists a cell in its migration. Localization of the uPA/plasmin system on the cell surface, or the leading edge of metastasizing cells, is consistent with postulated role of uPA in metastasis [Plesner et al., Stem Cells 15:398–408 (1997)].

Interaction of uPAR with vitronectin, a component of the extracellular matrix, mediates cell adhesion and can be enhanced when uPAR is bound by uPA. Cell surface adhesion molecules, integrins, also appear to be involved in this adhesion function, particularly beta-1 and beta-2 integrins [Paysant et al., Br. J. Haematol. 100:45–51 (1998); Simon et al., Blood 88:3185–3194 (1996)]. The CD11b/CD18 integrin can associate with the uPA-uPAR complex and promote adhesion of cells bearing these receptors, e.g., neutrophils, leukocytes.

The uPA/uPAR system also is involved in the establishment of new vasculature, or neovascularization.

Establishment of new vasculature is required for sustaining primary and metastatic tumor growth. Pathological neovascularization also is a characteristic of retinal disease, rubeosis iritis, proliferative vitreo retinopathy inflammatory disease, diabetic retinopathy, chronic uveitis, Fuch's heterochromic iridocyclitis, neovascular glaucoma, corneal or optic nerve neovascularization, vascular disease, pterygium, glaucoma surgery bleb failure, hyperkeratosis, cheloid and polyp formation (see EP 451,130). Undesired angiogenesis also can occur in the following conditions or can be a result of the following activities: macular degeneration, retinopathy of prematurity, corneal graft rejection, retrolental fibroplasia, epidemic keratoconjunctivitis, Vitamin A deficiency, contact lens overwear, atopic keratitis, superior limbic keratitis, pterygium keratitis sicca, sogrens disease, acne rosacea, phylectenulosis, syphilis, Mycobacteria infections other than leprosy, lipid degeneration, chemical burns, bacterial or fungal ulcers, Herpes simplex or zoster infections, protozoan infections, Kaposi's sarcoma, Mooren ulcer, Terrien's marginal degeneration, marginal keratolysis, trauma, rheumatoid arthritis, systemic lupus, polyarteritis, Wegeners sarcoidosis, sleritis, Steven's Johnson disease, radial keratotomy, sickle cell anemia, sarcoid, pseudoxanthoma elasticum, Pagets disease, vein or artery occlusion, carotid obstructive disease, chronic uveitis, chronic vitritis, Lyme's disease, Eales disease, Bechets disease, myopia, optic pits, Stargarts disease, pars planitis, chronic retinal detachment, hyperviscosity syndromes, toxoplasmosis, post-laser complications, abnormal proliferation of fibrovascular tissue, hemangiomas, Osler-Wever-Rendu, solid tumors, blood borne tumors, AIDS, ocular neovascular disease, osteoarthritis, chronic inflammation, Crohn's disease, ulcerative colitis, tumors of rhabdomyosarcoma, tumors of retinoblastoma, tumors of Ewing sarcoma, tumors of neuroblastoma, tumors of osteosarcoma, leukemia, psoriasis, atherosclerosis, pemphigoid, as recited in U.S. Pat. No. 5,712,291.

An antagonist of uPA/uPAR binding (EGF-like domain of uPA fused to Fc of IgG) was said to inhibit neovascularization and growth of the murine B16 melanoma. [Min et al., Cancer Res. 56:2428–2433 (1996)]. Consistent with this finding is the correlation noted between microvessel density, vascular invasion and uPA levels in breast carcinomas [Hildenbrand et al., Brit. J. Cancer 72:818–823 (1995)]. The known uPA inhibitor amiloride also was said to inhibit a variety of neovascularization pathologies [Glaser et al., EP 451,130; Avery et al., Arch. Ophthalmol. 108:1474–1476 (1990)].

There are two primary physiological inhibitors of uPA, PAI-1 and PAI-2, which are members of the serpin family of proteinase inhibitors. The binding of serpins to their cognate proteases involves a large number of interactions between amino acids of each protein, including those in the serpin reactive loop (Ser-Ala-Arg-Met-Ala (SEQ. ID. NO. 1) for PAI-1, Thr-Gly-Arg-Thr-Gly (SEQ. ID. NO. 2) for PAI-2). Introduction of exogenous PAI-2 into experimental animals was reported to inhibit the rate of lung metastasis [Evans and Lin, Amer. Surg. 61:692–697 (1995); Mueller et al., Proc. Natl. Acad. Sci. USA 92:205–209 (1995)]. The ability of PAI-1 to inhibit metastasis has not yet been consistently shown. The gene for PAI-1, and means for its recombinant expression, are disclosed in Loskutoff et al., U.S. Pat. No. 4,952,512. Recombinant and native human PAI-2 is disclosed in Stephens et al., U.S. Pat. No. 5,422,090.

The most widely studied uPA inhibitors may be within the 4-substituted benzo[b]thiophene-2-carboxamidine class of inhibitors, of which B428 (4-iodo-benzo[b]thiophene-2-carboxamidine) and B623 are members [Towle et al., Cancer Res. 53:2553–2559 (1993); Bridges et al., Bioorg. Med. Chem. 1:403–410 (1993); Bridges et al., U.S. Pat. No. 5,340,833]. Infusion of B428 in experimental rats inoculated with tumor cells was said to inhibit uPAR gene expression, decrease the primary tumor volume and decrease metastases [Xing et al., Cancer Res. 57:3585–3593 (1997)]. Daily intraperitoneal treatment of mice bearing tumors with B428 or B623 was said to block metastasis to muscle and fat, but did not inhibit tumor-induced angiogenesis or reduce the rate of spontaneous lung metastasis. In fact, B623 enhanced the formation of lung metastasis (Alonso et al., Breast Cancer Res. Treat. 40:209–223 (1996)]. Infusion of B428 in a syngeneic model of rat prostate cancer also lead to a decrease in primary tumor volume and tumor weight, and a decrease in metastasis [Rabbani et al., Int. J. Cancer 63:840–845 (1995)].

Other known inhibitors of uPA include p-aminobenzamidine, which is a competitive inhibitor of uPA, and amiloride. Both compounds have been shown to reduce tumor size in experimental animals [Jankan et al., Cancer Res. 57:559–563 (1997); Billstrom et al., Int. J. Cancer 61:542–547 (1995)]. Recently, epigallo-cathecin-3 gallate (EGCG), a polyphenol found in green tea, was reported to bind uPA and inhibit its activity [Jankun et al., Nature 387:561 (1997)]. Those researchers concluded EGCG is a weaker inhibitor of uPA than amiloride, but suggested EGCG can be consumed in much higher doses than amiloride without toxic effect. A competitive inhibitor of uPA, α-N-benzylsulfonyl-p-aminophenylalanine, is disclosed by Pye et al. in U.S. Pat. No. 4,165,258.

Other approaches at inhibiting the uPA/uPAR system include development of a bifunctional hybrid molecule consisting of the uPAR-binding domain of uPA and PAI-2, which is said to inhibit uPA and bind uPAR in vitro [Ballance et al., Eur. J. Biochem. 207:177–183 (1992)]. Antagonists of uPAR also have been studied [Doyle and Rosenberg, U.S. Pat. No. 5,656,726; Min et al., Cancer Res. 56:2428–2433 (1996)], as have antisense oligonucleotides complementary to uPA [Wilhelm et al., Clin. Exp. Metast. 13:296–302 (1995); Iversen and Scholar, U.S. Pat. No. 5,552,390]. Antibodies directed against uPAR, and said to inhibit the binding of uPA to uPAR, are disclosed by Dano et al. in U.S. Pat. No. 5,519,120. Small molecules said to inhibit urokinase, along with a variety of other serine proteases, include those disclosed by Abe et al. in U.S. Pat. No. 5,508,385 and U.S. Pat. No. 5,153,176, and by Takano et al. in J. Pharmacol. Exp. Therapeut. 271:1027–1033 (1994).

Compounds have been developed to directly inhibit the binding of u-PA to uPAR (Crowley et al., Proc. Natl. Acad. Sci. USA 90:5021–5025 (1993); Goodson et al., Proc. Natl. Acad. Sci. USA 91:7129–7133 (1994); Kobayashi et al., Brit. J. Cancer 67:537–544 (1993), and Int. J. Cancer 57:727–73f3 (1994), and J. Biol. Chem. 270:8361–8366 (1995); Lu et al., FEBS Lett. 356:56–59 (1994) and FEBS Lett. 380:21–24 (1996)]. Additionally, pro-hepatocyte growth factor (HGF), a cell migration stimulating protein, is a substrate of uPA [Naldinie et al., EMBO J. 11:4825–4833 (1992)]. Direct cleavage of a 66 kDa extracellular matrix protein and fibronectin by uPA also has been reported, which suggests a more direct role for uPA in facilitating cell migration [Quigley et al., Proc. Natl. Acad. Sci. 84:2776–2780 (1987)]. Thus, inhibition of uPA may affect these activities, as well.

SUMMARY OF THE INVENTION

The present invention is directed to novel pepitidic non-covalent urokinase inhibitors. The compounds have an arginine mimic at P1. These compounds have activity as potent inhibitors of urokinase and thereby are useful in decreasing its deleterious effects. Compounds of the present invention are active in inhibiting blood vessel formation, particularly that related to a pathologic process.

Thus in one aspect, the present invention is directed to compounds of the formula (I):

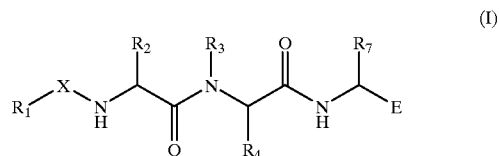

wherein:
(a) X is selected from the group consisting of —S(O)$_2$—, —N(R')—S(O)$_2$—, —(C=O)—, —OC(=O)—, —NH—C(=O)—, —P(O)(R')—, and a direct link, wherein R' is independently hydrogen, alkyl of 1 to about 4 carbon atoms, aryl of about 6 to about 14 carbon atoms or aralkyl of about 7 to about 16 carbon atoms, with the proviso that when X is —P(O)(R')—, then R' is not hydrogen;
(b) R$_1$ is selected from the group consisting of:
(1) alkyl of 1 to about 12 carbon atoms which is optionally substituted with Y$_1$ and/or Y$_2$,
(2) alkyl of 1 to about 3 carbon atoms substituted with cycloalkyl of about 3 to about 8 carbon atoms which is optionally mono-, di- or tri-substituted with Y$_1$, Y$_2$, and/or Y$_3$,
(3) cycloalkyl of 3 to about 15 carbon atoms, which is optionally mono-, di-, or tri-substituted on the ring with Y$_1$, Y$_2$, and/or Y$_3$,
(4) heterocycloalkyl of 4 to about 10 ring atoms with the ring atoms selected from carbon and heteroatoms, wherein the heteroatoms are selected from the group consisting of oxygen, nitrogen, and S(O)$_i$, wherein i is 0, 1 or 2, which is optionally mono-, di-, or tri-substituted on the ring with Y$_1$, Y$_2$, and/or Y$_3$,
(5) heterocyclo of 4 to about 10 ring atoms with the ring atoms selected from carbon and heteroatoms, wherein the heteroatoms are selected from the group consisting of oxygen, nitrogen, and S(O)$_i$, wherein i is 0, 1, or 2, including,

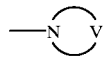

wherein

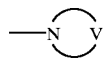

is a 5 to 7 member heterocycle having 3 to 6 ring carbon atoms, where V is —CH$_2$—, —O—, —S(=O)—, —S(O)$_2$— or —S—, which is optionally mono-, di-, or tri-substituted on the ring carbons with Y$_1$, Y$_2$, and/or Y$_3$,
(6) alkenyl of 2 to about 6 carbon atoms which is optionally substituted with cycloalkyl of about 3 to about 8 carbon atoms, which is optionally mono-, di-, or tri-substituted on the ring with Y$_1$, Y$_2$, and/or Y$_3$,
(7) aryl of about 6 to about 14 carbon atoms which is optionally mono-, di- or tri-substituted with Y$_1$, Y$_2$, and/or Y$_3$,
(8) heteroaryl of about 5 to about 14 ring atoms with the ring atoms selected from carbon and heteroatoms, wherein the heteroatoms are selected from oxygen, nitrogen, and sulfur, and which is optionally mono-, di- or tri-substituted with Y$_1$, Y$_2$, and/or Y$_3$,
(9) aralkyl of about 7 to about 15 carbon atoms which is optionally substituted on the alkyl chain with hydroxy or halogen and which is optionally mono-, di-, or tri-substituted on the aryl ring with Y$_1$, Y$_2$, and/or Y$_3$,
(10) heteroaralkyl of about 5 to about 14 ring atoms with the ring atoms selected from carbon and heteroatoms, wherein the heteroatoms are selected from oxygen, nitrogen, and sulfur, which is optionally substituted on the alkyl chain with hydroxy or halogen and which is optionally mono-, di- or tri-substituted on the ring with Y$_1$, Y$_2$, and/or Y$_3$,
(11) aralkenyl of about 8 to about 16 carbon atoms which is optionally mono-, di-, or tri-substituted on the aryl ring with Y$_1$, Y$_2$, and/or Y$_3$,
(12) heteroaralkenyl of about 5 to about 14 ring atoms with the ring atoms selected from carbon and heteroatoms, wherein the heteroatoms are selected from oxygen, nitrogen, and sulfur, and which is optionally mono-, di- or tri-substituted on the ring carbons with Y$_1$, Y$_2$, and/or Y$_3$,

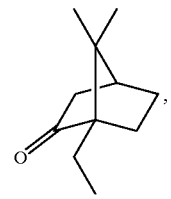

(13)

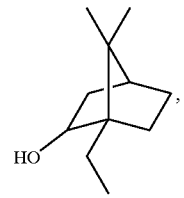

(14)

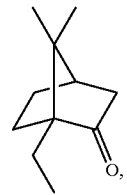

(15)

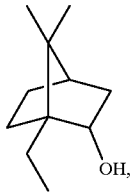

(16)

(17) fused carbocyclic alkyl of about 9 to about 15 carbon atoms;
(18) difluoromethyl or perfluoroalkyl of 1 to about 12 carbon atoms,
(19) perfluoroaryl of about 6 to about 14 carbon atoms,
(20) perfluoroaralkyl of about 7 to about 15 carbon atoms, and
(21) hydrogen when X is a direct link; wherein each Y$_1$, Y$_2$, and Y$_3$ is independently selected and is
(i) selected from the group consisting of halogen, cyano, nitro, tetrazolyl, guanidino, amidino, methylguanidino, —CF$_3$, —CF$_2$CF$_3$, —CH(CF$_3$)$_2$, —C(OH)(CF$_3$)$_2$, —OCF$_3$, —OCF$_2$H, —OCF$_2$CF$_3$, —OC(O)NH$_2$, —OC(O)NHZ$_1$, —OC(O)NZ$_1$Z$_2$, —NHC(O)Z$_1$, —NHC(O)NH$_2$, —NHC(O)NZ$_1$, —HC(O)NZ$_1$Z$_2$, —C(O)OH, —C(O)OZ$_1$, —C(O)NH$_2$, —C(O)NHZ$_1$, —C(O)NZ$_1$Z$_2$, —P(O)$_3$H$_2$, —P(O)$_3$(Z$_1$)$_2$, —S(O)$_3$H, —S(O)$_m$Z$_1$, —Z$_1$, —OZ$_1$, —OH, —NH$_2$, —NHZ$_1$, —NZ$_1$Z$_2$, —N-morpholino, and —S(O)$_m$(CF$_2$)$_q$CF$_3$, wherein m is 0, 1 or 2, q is an integer from 0 to 5, and Z$_1$ and Z$_2$ are independently selected from the group consisting of alkyl of 1 to about 12 carbon atoms, aryl of about 6 to about 14 carbon atoms, heteroaryl of about 5 to about 14 ring atoms, aralkyl of about 7 to about 15 carbon atoms, and heteroaralkyl of about 5 to about 14 ring atoms, or (ii) Y$_1$ and Y$_2$ are selected together to be —O[C(Z$_3$)(Z$_4$)]$_r$O— or —O[C(Z$_3$)(Z$_4$)]$_{r+1}$—, wherein r is an integer from 1 to 4 and Z$_3$ and Z$_4$ are independently selected from the group consisting of hydrogen, alkyl of 1 to about 12 carbon atoms, aryl of about 6 to about 14 carbon atoms, heteroaryl of about 5 to about 14 ring atoms, aralkyl of about 7 to about 15 carbon atoms, and heteroaralkyl of about 5 to about 14 ring atoms;

(c) R$_2$ is selected from the group consisting of —CH$_3$, —C$_2$H$_5$, —(CH$_2$)$_2$OH, —(CH$_2$)$_2$OA$_1$, —CH(R$_5$) OH, —CH (R$_5$) OA$_1$ and —CH$_2$NH—X'—R$_6$ wherein A$_1$ is —C(=O)OR$_6$, —C(=O)R$_6$ or —C(=O)NR$_5$R$_6$; X' is selected from the group consisting of —S(O)$_2$—, —S(O)$_2$—N(R")—, —(C=O)—, —C(=O)—O—, —C(=O)—NH—, —P(O) (R")—, and a direct link, wherein R" is hydrogen, alkyl of 1 to about 4 carbon atoms, aryl of about 6 to about 14 carbon atoms or aralkyl of about 7 to about 16 carbon atoms with the proviso that when X' is —P(O)(R")—, then R" is not hydrogen; R$_5$ is selected from the group consisting of:

(1) alkyl of 1 to about 4 carbon atoms, optionally substituted with Y$_1$ and/or Y$_2$,
(2) alkyl of 1 to about 3 carbon atoms substituted with cycloalkyl of 3 to about 6 carbon atoms, which is optionally mono-, di-, or tri-substituted on the ring with Y$_1$, Y$_2$, and/or Y$_3$,
(3) cycloalkyl of 3 to about 6 carbon atoms, which is optionally mono-, di-, or trisubstituted on the ring with Y$_1$, Y$_2$, and/or Y$_3$,
(4) heterocycloalkyl of 4 to about 6 ring atoms with the ring atoms selected from carbon and heteroatoms, wherein the heteroatoms are selected from the group consisting of oxygen, nitrogen, and S(O)$_i$, wherein i is 0, 1 or 2, which is optionally mono-, di-, or tri-substituted on the ring with Y$_1$, Y$_2$, and/or Y$_3$,
(5) heterocyclo of 4 to about 6 ring atoms with the ring atoms selected from carbon and heteroatoms, wherein the heteroatoms are selected from the group consisting of oxygen, nitrogen, and S(O)$_i$, wherein i is 0, 1, or 2, including

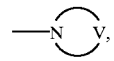

wherein

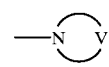

is a 5 to 6 member heterocycle having 3 to 5 ring carbon atoms, where V is —CH$_2$—, —O—, —S(=O)—, —S(O)$_2$— or —S—, which is optionally mono-, di-, or tri-substituted on the ring carbons with Y$_1$, Y$_2$, and/or Y$_3$, (6) alkenyl of 2 to about 6 carbon atoms which is optionally substituted with cycloalkyl of 3 to about 6 carbon atoms, which is optionally mono-, di-, or tri-substituted on the ring with Y$_1$, Y$_2$, and/or Y$_3$,
(7) phenyl which is optionally mono-, di- or tri-substituted with Y$_1$, Y$_2$, and/or Y$_3$,
(8) heteroaryl of about 5 to about 6 ring atoms with the ring atoms selected from carbon and heteroatoms, wherein the heteroatoms are selected from oxygen, nitrogen, and sulfur, and which is optionally mono-, di- or tri-substituted with Y$_1$, Y$_2$, and/or Y$_3$,
(9) alkyl of 1 to about 4 carbon atoms which is substituted with phenyl and which is optionally mono-, di-, or tri-substituted on the phenyl ring with Y$_1$, Y$_2$, and/or Y$_3$,
(10) heteroaralkyl of about 5 to about 6 ring atoms with the ring atoms selected from carbon and heteroatoms, wherein the heteroatoms are selected from oxygen, nitrogen, and sulfur, and which is optionally substituted on the alkyl chain with hydroxy or halogen and optionally mono-, di- or tri-substituted on the ring with Y$_1$, Y$_2$, and/or Y$_3$,
(11) aralkenyl of about 8 to about 12 carbon atoms which is optionally mono-, di-, or tri-substituted on the aryl ring with Y$_1$, Y$_2$, and/or Y$_3$,
(12) heteroaralkenyl of 5 to about 6 ring atoms with the ring atoms selected from carbon and heteroatoms, wherein the heteroatoms are selected from oxygen, nitrogen, and sulfur, and which is optionally mono-, di- or tri-substituted on the ring carbons with Y$_1$, Y$_2$, and/or Y$_3$, and
(13) hydrogen; and R$_6$ is selected from the group consisting of:
(1) alkyl of 1 to about 12 carbon atoms, optionally substituted with Y$_1$ and/or Y$_2$,
(2) alkyl of 1 to about 3 carbon atoms substituted with cycloalkyl of 3 to about 8 carbon atoms, which is optionally mono-, di-, or tri-substituted on the ring with Y$_1$, Y$_2$, and/or Y$_3$,
(3) cycloalkyl of 3 to about 15 carbon atoms, which is optionally mono-, di-, or trisubstituted on the ring with Y$_1$, Y$_2$, and/or Y$_3$,
(4) heterocycloalkyl of 4 to about 10 ring atoms with the ring atoms selected from carbon and heteroatoms, wherein the heteroatoms are selected from the group consisting of oxygen, nitrogen, and S(O)$_i$, wherein i is 0, 1 or 2, which is optionally mono-, di-, or tri-substituted on the ring with Y$_1$, Y$_2$, and/or Y$_3$,
(5) heterocyclo of 4 to about 10 ring atoms with the ring atoms selected from carbon and heteroatoms, wherein the heteroatoms are selected from the group consisting of oxygen, nitrogen, and S(O)$_i$, wherein i is 0, 1, or 2, including

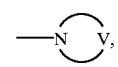

wherein

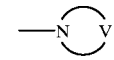

is a 5 to 7 member heterocycle having 3 to 6 ring carbon atoms, where V is —CH$_2$—, —O—, —S(=O)—, —S(O)$_2$— or —S—, which is optionally mono-, di-, or tri-substituted on the ring carbons with Y$_1$, Y$_2$, and/or Y$_3$,
(6) aryl of about 6 to about 14 carbon atoms which is optionally mono-, di- or tri-substituted with Y$_1$, Y$_2$, and/or Y$_3$,
(7) heteroaryl of about 5 to about 14 ring atoms with the ring atoms selected from carbon and heteroatoms, wherein the heteroatoms are selected from oxygen, nitrogen, and sulfur, and which is optionally mono-, di- or tri-substituted with Y$_1$, Y$_2$, and/or Y$_3$,
(8) aralkyl of about 7 to about 15 carbon atoms which is optionally mono-, di-, or tri-substituted on the aryl ring with Y$_1$, Y$_2$, and/or Y$_3$,
(9) heteroaralkyl of about 5 to about 14 ring atoms with the ring atoms selected from carbon and heteroatoms, wherein the heteroatoms are selected from oxygen, nitrogen, and sulfur, and which is optionally substituted on the alkyl chain with hydroxy or halogen and optionally mono-, di- or tri-substituted on the ring with Y$_1$, Y$_2$, and/or Y$_3$, and
(10) hydrogen, with the proviso that R$_6$ is not hydrogen when A$_1$ is —C(=O)OR$_6$;
(d) R$_3$ is selected from H or methyl, or R$_3$ and R$_4$ are selected together as set forth in (f);
(e) R$_4$ is in the S configuration and is selected from the group consisting of H, —CH$_2$—S—CH$_3$, —CH$_2$OH, —CH$_2$CN, lower alkyl of 1 to about 3 carbon atoms, —CH$_2$C≡CH, —CH$_2$CH=CH$_2$ and —CH=CH$_2$ or R$_3$ and R$_4$ are selected together as set forth in (f);
(f) alternatively, R$_3$ and R$_4$ are selected together to be in the S configuration to give a group at P2 selected from the group consisting of prolyl, pipecolyl, azetidine-2-carbonyl, 4-hydroxyprolyl, 3-hydroxyprolyl, 3,4-methanoprolyl, and 3,4-dehydroprolyl;
(g) R$_7$ is hydrogen or alkyl of 1 to about 4 carbon atoms; and
(h) E is selected from

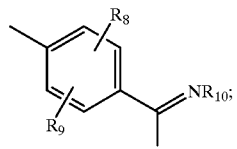

(1)

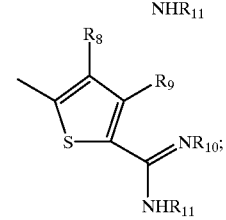

(2)

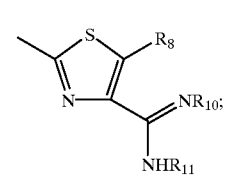

(3)

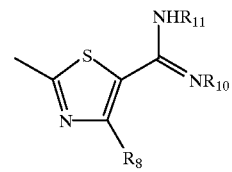

(4)

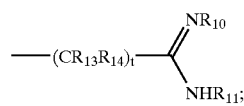

(5)

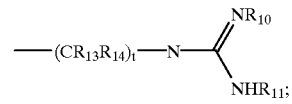

(6)

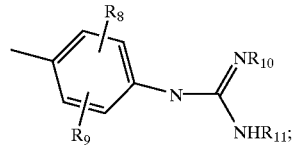

(7)

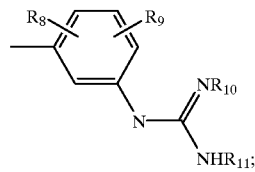

(8)

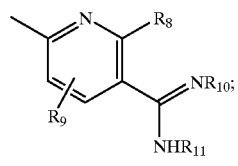

(9)

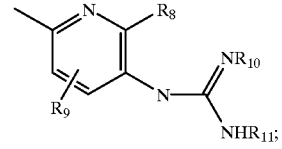

(10)

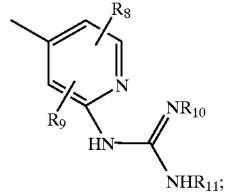

(11)

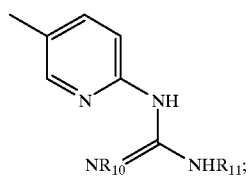

(12)

-continued

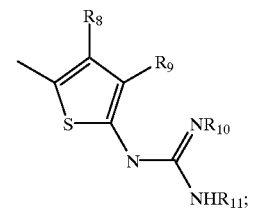
(13)

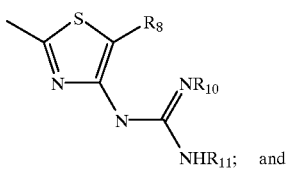
(14)

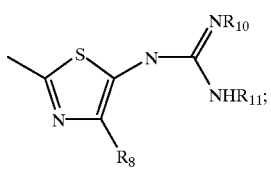
(15)

wherein $R_8$ and $R_9$ are independently selected from hydrogen, hydroxy, halogen, alkyl of 1 to about 4 carbon atoms, alkyl of 1 to about 4 carbon atoms substituted with alkoxy of 1 to about 4 carbon atoms, alkoxy of 1 to about 6 carbon atoms, and trifluoromethyl; $R_{10}$ and $R_{11}$ are independently hydrogen, hydroxy, alkoxy of 1 to about 3 carbon atoms, trihydrocarbylsilyl of 3 to about 16 carbon atoms, alkyl of 1 to about 3 carbon atoms or —C(=O)$R_{12}$; $R_{12}$ is hydrogen, alkyl of 1 to about 6 carbon atoms, alkoxy of 1 to about 6 carbon atoms or $(CF_2)_jCF_3$ wherein j is 0, 1, 2 or 3 with the proviso that $R_{10}$ and $R_{11}$ are not both hydroxy or alkoxy; each of $R_{13}$ and $R_{14}$ is independently selected from hydrogen or lower alkyl of 1 to about 3 carbon atoms; and t is an integer from 0 to 6; and pharmaceutically acceptable salts thereof.

The compounds of the present invention can be divided into parts termed $P_1$, $P_2$, $P_3$ and $P_4$ as shown in the following formula Ia:

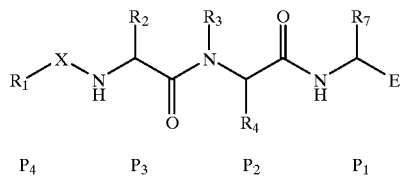

wherein X, $R_1$, $R_2$, $R_3$, $R_4$, $R_7$ and E are as defined in connection with formula (I). Thus, the portion of a compound of formula (I) referred to as $P_1$ or P1 is the moiety

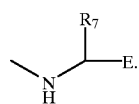
(Ia)

The portion of a compound of formula (I) referred to as $P_2$ or P2 is the moiety

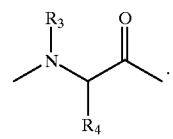

The portion of a compound of formula (I) referred to as $P_3$ or P3 is the moiety

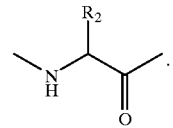

Among other factors, the present invention is based on our finding that the novel compounds of our invention are active as inhibitors of urokinase. Compounds of the present invention exhibit activity in inhibiting angiogenesis.

In another aspect, the present invention is directed to pharmaceutical compositions comprising a therapeutically effective amount of a compound of the present invention and a pharmaceutically acceptable carrier.

In yet another aspect, the present invention is directed to methods of using the compounds and pharmaceutical compositions of the present invention for inhibition of urokinase.

Definitions

In accordance with the present invention and as used herein, the following terms are defined to have following meanings, unless explicitly stated otherwise:

The term "alkenyl" refers to unsaturated aliphatic groups having at least one double bond.

The term "alkyl" refers to saturated aliphatic groups including straight-chain, branched-chain and cyclic (including polycyclic) groups.

The terms "alkoxy" and "alkoxyl" refer to a group having the formula, R—O—, wherein R is an alkyl group.

The term "alkoxycarbonyl" refers to —C(O)OR wherein R is alkyl.

The term "aralkenyl" refers to an alkenyl group substituted with an aryl group. Preferably the alkenyl group has from 2 to about 6 carbon atoms.

The term "aralkyl" refers to an alkyl group substituted with an aryl group. Suitable aralkyl groups include benzyl, phenethyl, and the like, all of which may be optionally substituted. Preferably the alkyl group has from 1 to about 6 carbon atoms.

The term "aryl" refers to an aromatic group which has at least one ring having a conjugated pi electron system and includes a carbocyclic aryl, heterocyclic aryl and biaryl groups, all of which may be optionally substituted.

The term "aryloxy" refers to a group having the formula, R—O—, wherein R is an aryl group.

The term "aralkoxy" refers to a group having the formula, R—O—, wherein R is an aralkyl group.

The term "amino acid" refers to both natural, unnatural amino acids in their D and L stereo isomers if their structures allow such stereoisomeric forms, and their analogs. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr) and valine (Val). Unnatural amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4 diaminoisobutyric acid, demosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine and pipecolic acid. Amino acid analogs include the natural and unnatural amino acids which are chemically blocked, reversibly or irreversibly, or modified on their N-terminal amino group or their side-chain groups, as for example, methionine sulfoxide, methionine sulfone, S-(carboxymethyl)-cysteine, S-(carboxymethyl)-cysteine sulfoxide and S-(carboxymethyl)-cysteine sulfone.

The term "amino acid analog" refers to an amino acid wherein either the C-terminal carboxy group, the N-terminal amino group or side-chain functional group has been chemically modified to another functional group. For example, aspartic acid-(beta-methyl ester) is an amino acid analog of aspartic acid; N-ethylglycine is an amino acid analog of glycine; or alanine carboxamide is an amino acid analog of alanine.

The term "amino acid residue" refers to radicals having the structure: (1) —C(O)—R—NH—, wherein R typically is —CH(R')—, wherein R' is H or a carbon containing substituent; or (2)

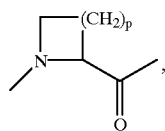

wherein p is 1, 2 or 3 representing the azetidinecarboxylic acid, proline or pipecolic acid residues, respectively.

"Biaryl" refers to phenyl substituted by carbocyclic or heterocyclic aryl as defined herein, ortho, meta or para to the point of attachment of the phenyl ring.

"Brine" refers to an aqueous saturated solution of sodium chloride.

"Carbocyclic aryl" refers to aromatic groups wherein the ring atoms on the aromatic ring are carbon atoms. Carbocyclic aryl groups include monocyclic carbocyclic aryl groups and naphthyl groups, all of which may be optionally substituted. Suitable carbocyclic aryl groups include phenyl and naphthyl. Suitable substituted carbocyclic aryl groups include indene and phenyl substituted by one to two substituents such being advantageously lower alkyl, hydroxy, lower alkoxy, lower alkoxycarbonyl, halogen, trifluoromethyl, difluoromethyl, nitro, and cyano. Substituted naphthyl refers to naphthyl, more preferably 1- or 2-naphthyl, substituted by $Y_1$, $Y_2$ and/or $Y_3$ as defined in connection with formula (I) hereinabove.

"Cycloalkenyl" refers to a cyclic alkenyl group. Suitable cycloalkenyl groups include, for example, cyclopentenyl and cyclohexenyl.

"Cycloalkyl" refers to a cyclic alkyl group having at least one ring and includes polycyclic groups, including fused ring cyclic alkyl groups. Suitable cycloalkyl groups include, for example, cyclohexyl, cyclopropyl, cyclopentyl, and cycloheptyl.

"Cyclohexylmethyl" refers to a cyclohexyl group attached to $CH_2$.

"Fused carbocyclic" refers to a multicyclic fused carbocyclic ring having both aromatic and non-aromatic rings. Suitable fused carbocyclic rings include fluorenyl, tetralin and the like.

"Fused carbocyclic alkyl" refers to an alkyl group substituted with a fused carbocyclic ring moiety, preferably a multicyclic fused carbocyclic ring including both aromatic and non-aromatic rings. Suitable fused carbocyclic alkyl groups include fluorenylmethyl, and the like.

The term "halogen" refers to fluorine, chlorine, bromine and iodine.

"Heteroaralkenyl" refers to an alkenyl group substituted with a heteroaryl, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems. Preferably the alkenyl group has from 2 to about 6 carbon atoms.

"Heteroaralkyl" refers to an alkyl group substituted with a heteroaryl, such as picolyl, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems. Preferably the alkyl group has from 1 to about 6 carbon atoms.

"Heteroaryl" refers to aromatic groups having from 1 to 14 carbon atoms and the remainder of the ring atoms are heteroatoms, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems. Suitable heteroatoms include oxygen, nitrogen, and $S(O)_i$, wherein i is 0, 1 or 2, and suitable heterocyclic aryls include furanyl, thienyl, pyridyl, pyrrolyl, pyrimidyl, pyrazinyl, imidazolyl, and the like.

"Heterocyclo" refers to a reduced heterocyclic ring system comprised of carbon, nitrogen, oxygen and/or sulfur atoms, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems.

"Heterocycloalkyl" refers to an alkyl group substituted with a heterocyclo group, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems. Preferably the alkyl group has from about 1 to about 6 carbon atoms.

The term "lower" referred to herein in connection with organic radicals or groups defines such radicals or groups with one and up to and including 5 carbon atoms, preferably up to and including 4 carbon atoms, and advantageously one or two carbon atoms. Such radicals or groups may be straight chain or branched chain.

"Perfluoroalkyl" refers to an alkyl group which has every hydrogen replaced with fluorine.

"Perfluoroaryl" refers to an aryl group which has every hydrogen replaced with fluorine.

"Perfluoroarylalkyl" refers to an aralkyl group in which every hydrogen on the aryl moiety is replaced with fluorine.

"Pharmaceutically acceptable salt" includes salts of the compounds of the present invention derived from the combination of such compounds and an organic or inorganic acid. In practice the use of the salt form amounts to use of the base form. The compounds of the present invention are useful in both free base and salt form, with both forms being considered as being within the scope of the present invention.

"AcN" or "MeCN" refers to acetonitrile.
"AIBN" refers to 2,2'-azobisisobutyronitrile.
"Bn" refers to benzyl.
"Boc" refers to t-butoxycarbonyl.
"Boc$_2$O" refers to Boc anhydride (di-tert-butyl carbonate).
"BzlSO$_2$" refers to benzylsulfonyl.
"Cbz" or "CBz" refers to benzyloxycarbonyl.
"CsCo$_3$" refers to cesium carbonate.
"DCA" refers to dichloroacetic acid.
"DCC" refers to N,N'-dicyclohexylcarbodiimide.
"DCM" refers to dichloromethane.
"DIEA" refers to diisopropylethylamine.
"DMF" refers to N,N-dimethylformamide.
"DMSO" refers to dimethyl sulfoxide.
"DMAP" refers to 4-N,N-dimethylaminopyridine.
"EDC" refers to 1-ethyl-3-(3-dimethylamino-propyl) carbodiimide hydrochloride salt.
"Et$_3$N" or "TEA" refers to triethylamine.
"EtOAc" refers to ethyl acetate.
"EtOH" refers to ethanol.
"HATU" refers to O-(7-azabenzotriazol-1-yl)-1,1,3,3-tetramethyluromium hexafluorophosphate.
"HBTU" refers to 2-(1H-benzotriazol-1-yl)-1,1,3,3-tetramethyluronium hexafluorophosphate.
"HCl" refers to hydrochloric acid.
"HOAc" refers to acetic acid.
"HOAt" or "HOAT" refers to 1-hydroxy-7-azabenzotriazole.
"HOBt" refers to 1-hydroxybenzotriazole monohydrate.
"1-BuOCOCl" refers to isobutylchloroformate.
"HPLC" refers to high pressure liquid chromatography.
"LiAlH$_4$" refers to lithium aluminum hydride.
"LiAlH$_2$(OEt)$_2$" refers to lithium aluminum hydride diethoxide.
"Me" refers to methyl.
"MeOH" refers to methanol.
"NMM" refers to N-methylmorpholine.
"NBS" refers to N-bromosuccinimide.
"PhB(OH)$_2$" refers to phenylboronic acid.
"Ph$_3$P" or "PPh$_3$" refers to triphenylphospine.
"PyBOP" refers to benzotriazole-ly-oxy-tris-pyrrolidino-phosphonium hexafluorophosphate.
"RP-HPLC" refers to reverse phase high pressure liquid chromatography.
"TFA" refers to trifluoroacetic acid.
"THF" refers to tetrahydrofuran.
"TLC" refers to thin layer chromatography.

BRIEF DESCRIPTION OF THE DRAWINGS

Figure 10E:
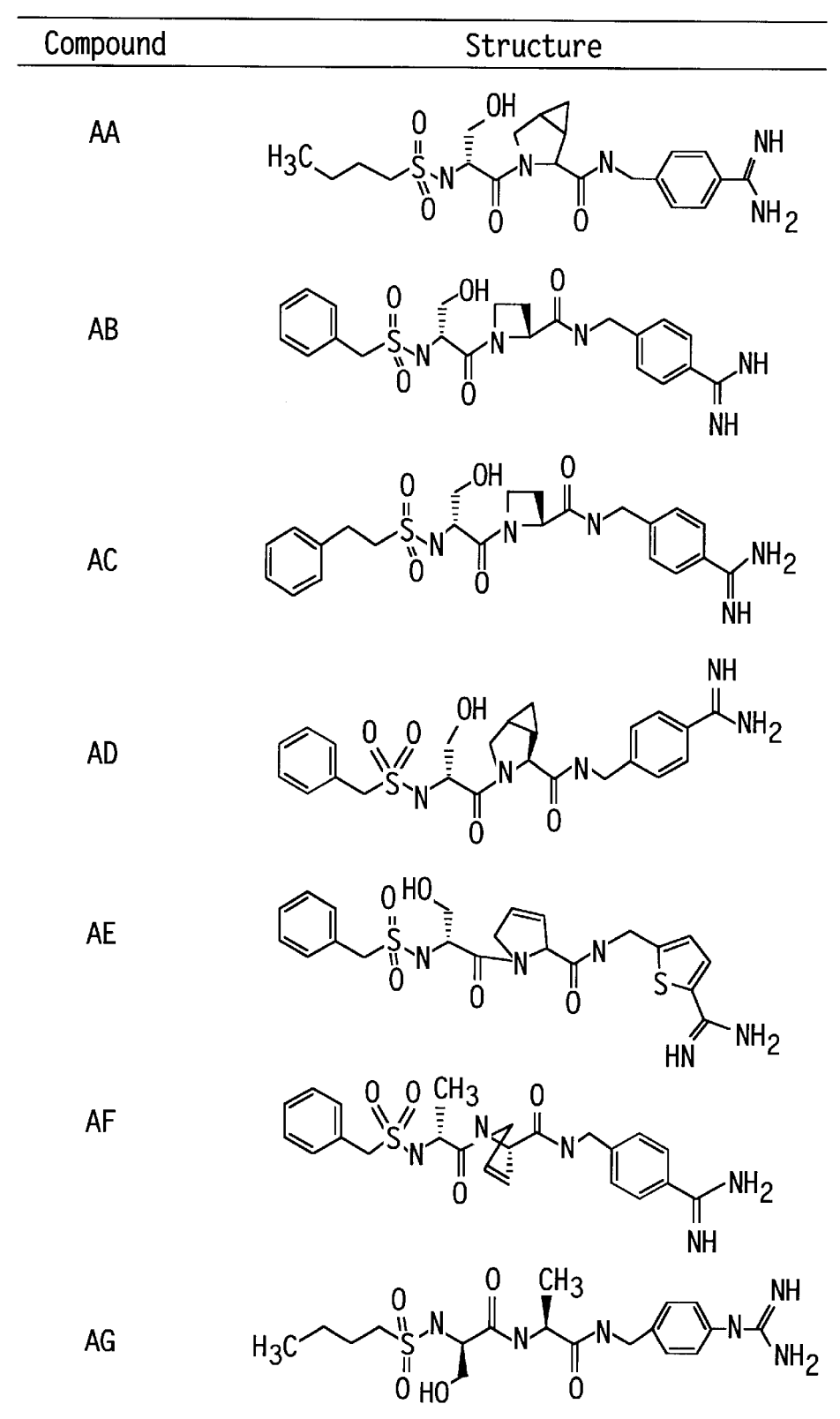
Figure 10F:
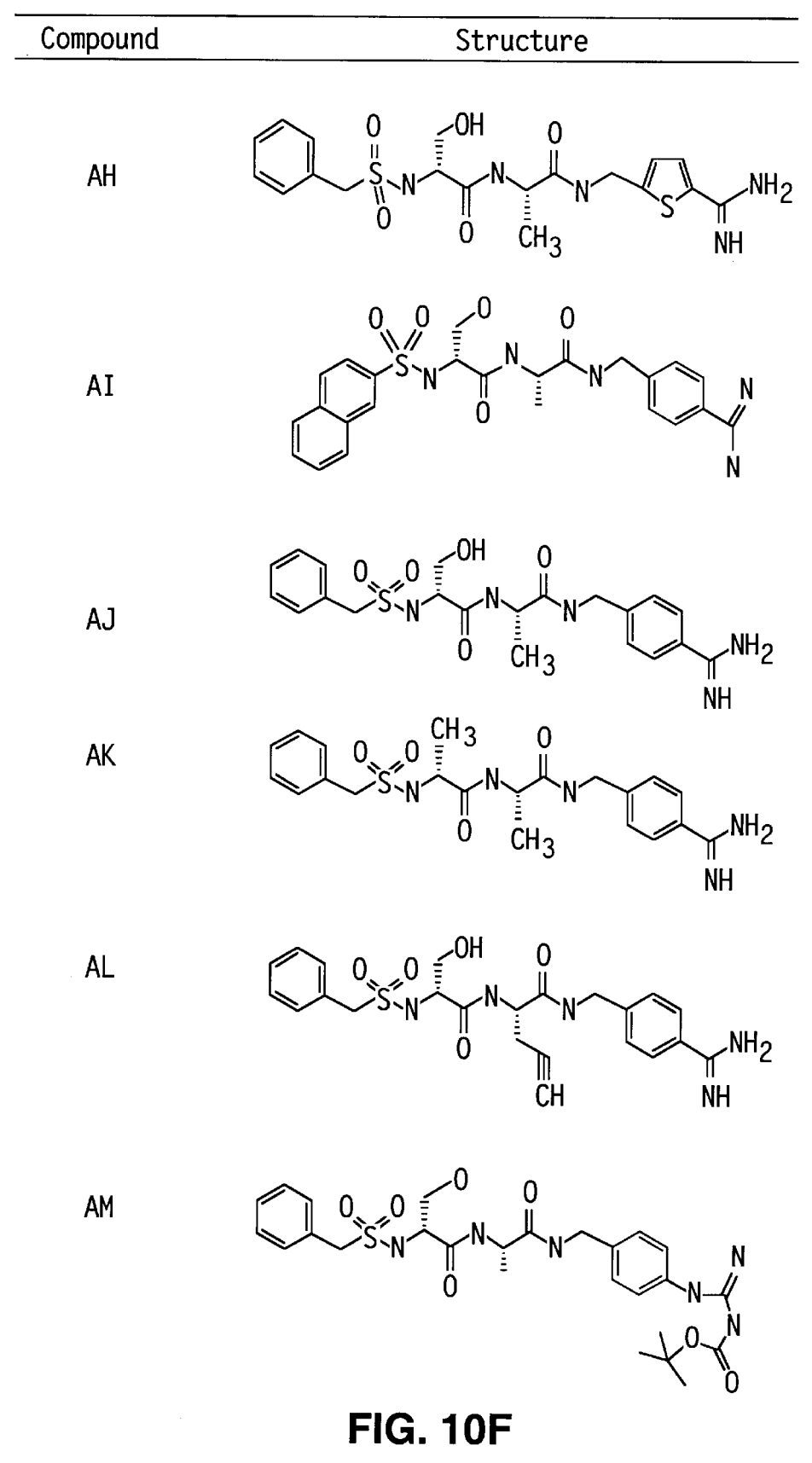
Figure 10G:
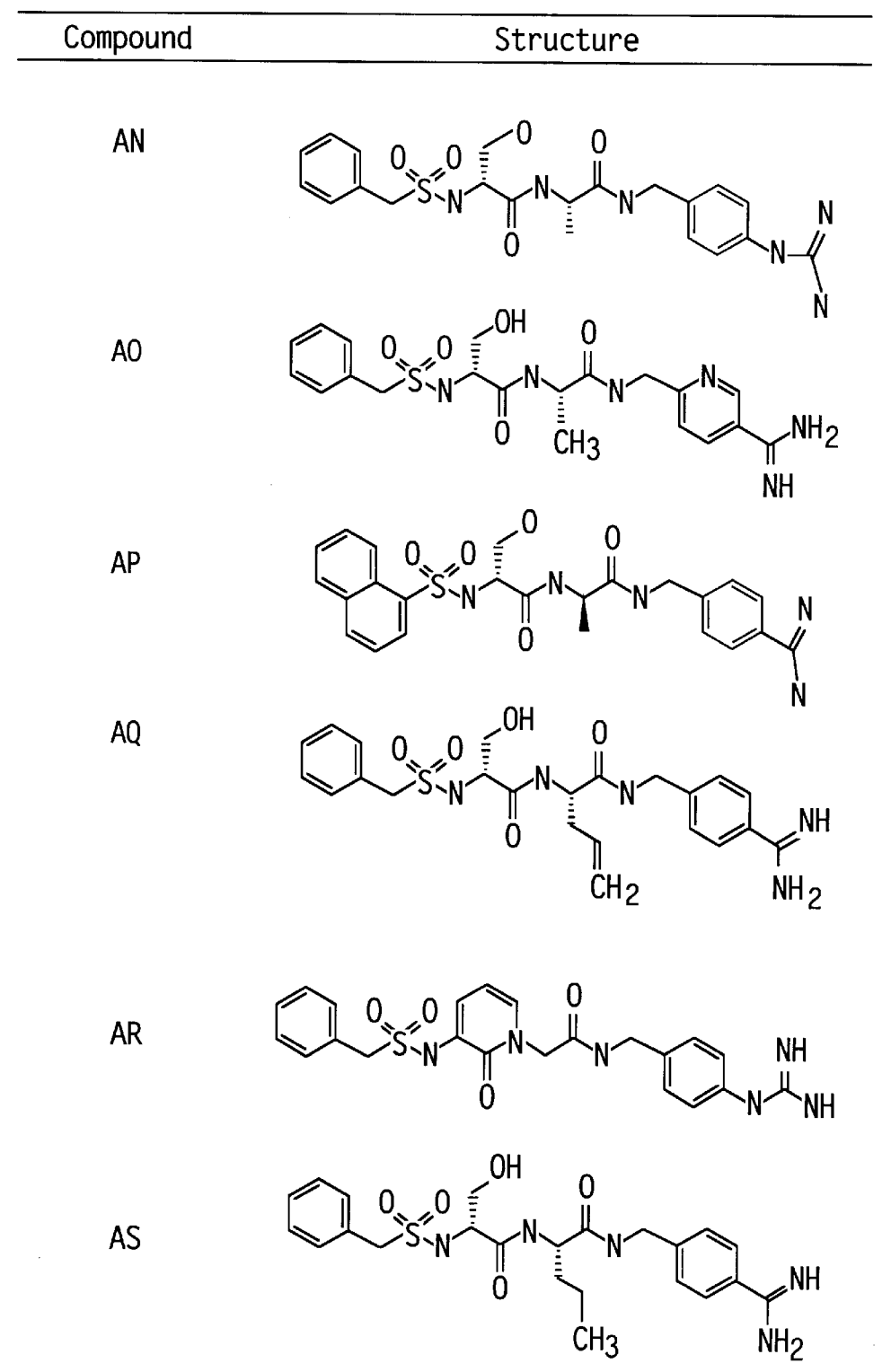
Figure 10H:
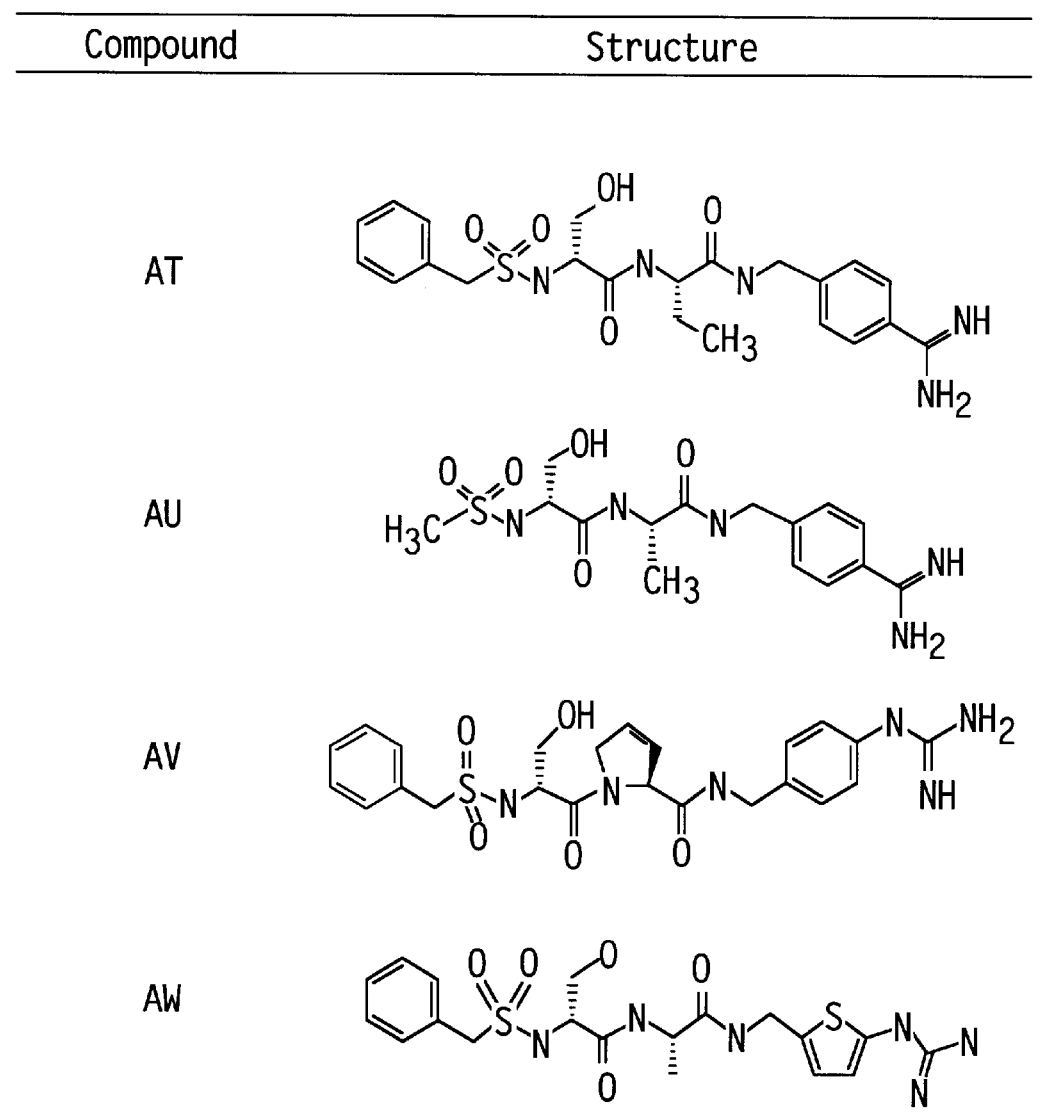

FIGS. 10A to 10H depict certain preferred compounds of the present invention.

DETAILED DESCRIPTION OF THE INVENTION

1. Preferred Compounds

Figure 1:
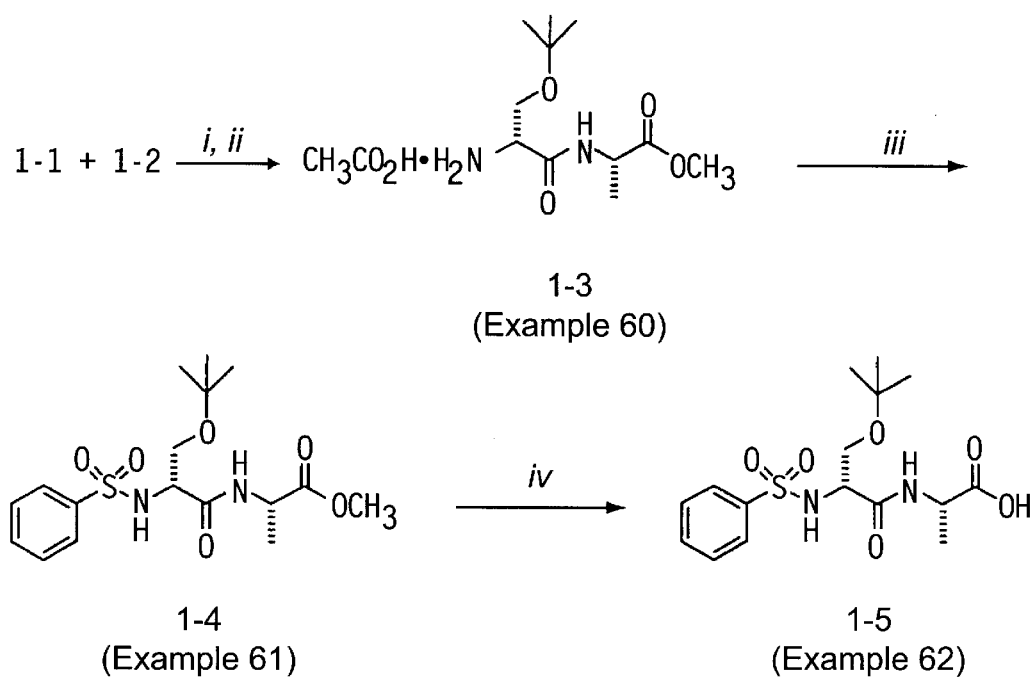
FIG. 1 depicts a reaction scheme for solution phase synthesis of an intermediate useful in synthesizing a compound of the present invention. Compound 1-1 is N-α-Cbz-D-serine (O-t-butyl), compound 1-2 is alanine methyl ester, hydrochloride salt. In this figure, "i" through "iv" are defined as i) EDC, 1-hydroxybenzotriazole and acetonitrile, diisopropylethylamine to give Cbz-D-Ser (O-t-butyl)-Ala-OMe; (ii) ethanol/acetic acid/water (4:1:1), 10% Pd on carbon, 45 psi H$_2$ for 2 hours, 95% yield after work-up; iii) acetonitrile, benzenesulfonyl chloride, diisopropyl-ethylamine, 43% yield after work-up; and iv) methanol, 1.0 M lithium hydroxide, acidification on DOWEX ion exchange resin, eluting with methanol/water, 95% yield after work-up. See also Examples 60 to 62.

Compounds of the present invention have the formula:

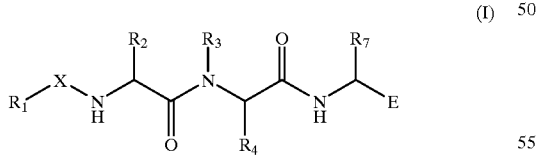

(I)

wherein:
(a) X is selected from the group consisting of —S(O)$_2$—, —N(R')—S(O)$_2$—, —(C=O)—, —OC(=O)—, —NH—C(=O)—, —P(O)(R')—, and a direct link, wherein R' is independently hydrogen, alkyl of 1 to about 4 carbon atoms, aryl of about 6 to about 14 carbon atoms or aralkyl of about 7 to about 16 carbon atoms, with the proviso that when X is —P(O)(R')—, then R' is not hydrogen;
(b) R$_1$ is selected from the group consisting of:

(1) alkyl of 1 to about 12 carbon atoms which is optionally substituted with Y$_1$, and/or Y$_2$,
(2) alkyl of 1 to about 3 carbon atoms substituted with cycloalkyl of about 3 to about 8 carbon atoms which is optionally mono-, di- or tri-substituted with Y$_1$, Y$_2$, and/or Y$_3$,
(3) cycloalkyl of 3 to about 15 carbon atoms, which is optionally mono-, di-, or tri-substituted on the ring with Y$_1$, Y$_2$, and/or Y$_3$,
(4) heterocycloalkyl of 4 to about 10 ring atoms with the ring atoms selected from carbon and heteroatoms, wherein the heteroatoms are selected from the group consisting of oxygen, nitrogen, and S(O)$_i$, wherein i is 0, 1 or 2, which is optionally mono-, di-, or tri-substituted on the ring with Y$_1$, Y$_2$, and/or Y$_3$,
(5) heterocyclo of 4 to about 10 ring atoms with the ring atoms selected from carbon and heteroatoms, wherein the heteroatoms are selected from the group consisting of oxygen, nitrogen, and S(O)$_i$, wherein i is 0, 1, or 2, including,

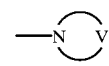

wherein

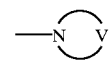

is a 5 to 7 member heterocycle having 3 to 6 ring carbon atoms, where V is —CH$_2$—, —O—, —S(=O)—, —S(O)$_2$— or —S—, which is optionally mono-, di-, or tri-substituted on the ring carbons with Y$_1$, Y$_2$, and/or Y$_3$,
(6) alkenyl of 2 to about 6 carbon atoms which is optionally substituted with cycloalkyl of 3 to about 8 carbon atoms, which is optionally mono-, di-, or tri-substituted on the ring with Y$_1$, Y$_2$, and/or Y$_3$,
(7) aryl of about 6 to about 14 carbon atoms which is optionally mono-, di- or tri-substituted with Y$_1$, Y$_2$, and/or Y$_3$,
(8) heteroaryl of about 5 to about 14 ring atoms with the ring atoms selected from carbon and heteroatoms, wherein the heteroatoms are selected from oxygen, nitrogen, and sulfur, and which is optionally mono-, di- or tri-substituted with Y$_1$, Y$_2$, and/or Y$_3$,
(9) aralkyl of about 7 to about 15 carbon atoms which is optionally substituted in the alkyl chain with hydroxy or halogen and which is optionally mono-, di-, or tri-substituted on the aryl ring with Y$_1$, Y$_2$, and/or Y$_3$,
(10) heteroaralkyl of about 5 to 14 ring atoms with the ring atoms selected from carbon and heteroatoms, wherein the heteroatoms are selected from oxygen, nitrogen, and sulfur, which is optionally substituted on the alkyl chain with hydroxy or halogen and which is optionally mono-, di- or tri-substituted on the ring with Y$_1$, Y$_2$, and/or Y$_3$,
(11) aralkenyl of about 8 to about 16 carbon atoms which is optionally mono-, di-, or tri-substituted on the aryl ring with Y$_1$, Y$_2$, and/or Y$_3$,
(12) heteroaralkenyl of about 5 to 14 ring atoms with the ring atoms selected from carbon and heteroatoms, wherein the heteroatoms are selected from oxygen, nitrogen, and sulfur, and which is optionally mono-, di- or tri-substituted on the ring carbons with $Y_1$, $Y_2$, and/or $Y_3$,

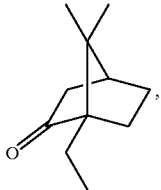 (13)

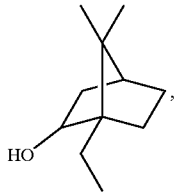 (14)

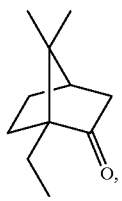 (15)

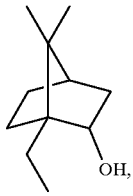 (16)

(17) fused carbocyclic alkyl of about 9 to about 15 carbon atoms;
(18) difluoromethyl or perfluoroalkyl of 1 to about 12 carbon atoms,
(19) perfluoroaryl of about 6 to about 14 carbon atoms,
(20) perfluoroaralkyl of about 7 to about 15 carbon atoms, and
(21) hydrogen when X is a direct link; wherein each $Y_1$, $Y_2$, and $Y_3$ is independently selected and is
  (i) selected from the group consisting of halogen, cyano, nitro, tetrazolyl, guanidino, amidino, methylguanidino, —$CF_3$, —$CF_2CF_3$, —$CH(CF_3)_2$, —$C(OH)(CF_3)_2$, —$OCF_3$, —$OCF_2H$, —$OCF_2CF_3$, —$OC(O)NH_2$, —$OC(O)NHZ_1$, —$OC(O)NZ_1Z_2$, —$NHC(O)Z_1$, —$NHC(O)NH_2$, —$NHC(O)NZ_1$, —$NHC(O)NZ_1Z_2$, —$C(O)OH$, —$C(O)OZ_1$, —$C(O)NH_2$, —$C(O)NHZ_1$, —$C(O)NZ_1Z_2$, —$P(O)_3H_2$, —$P(O)_3(Z_1)_2$, —$S(O)_3H$, —$S(O)_mZ_1$, —$Z_1$, —$OZ_1$, —$OH$, —$NH_2$, —$NHZ_1$, —$NZ_1Z_2$, —N-morpholino, and —$S(O)_m(CF_2)_qCF_3$, wherein m is 0, 1 or 2, q is an integer from 0 to 5, and $Z_1$ and $Z_2$ are independently selected from the group consisting of alkyl of 1 to about 12 carbon atoms, aryl of about 6 to about 14 carbon atoms, heteroaryl of about 5 to about 14 ring atoms, aralkyl of about 7 to about 15 carbon atoms, and heteroaralkyl of about 5 to about 14 ring atoms, or (ii) $Y_1$ and $Y_2$ are selected together to be —$O[C(Z_3)(Z_4)]_rO$— or —$O[C(Z_3)(Z_4)]_{r+1}$—, wherein r is an integer from 1 to 4 and $Z_3$ and $Z_4$ are independently selected from the group consisting of hydrogen, alkyl of 1 to about 12 carbon atoms, aryl of about 6 to about 14 carbon atoms, heteroaryl of about 5 to about 14 ring atoms, aralkyl of about 7 to about 15 carbon atoms, and heteroaralkyl of about 5 to about 14 ring atoms;

(c) $R_2$ is selected from the group consisting of —$CH_3$, —$C_2H_5$, —$(CH_2)_2OH$, —$(CH_2)_2OA_1$, —$CH(R_5)OH$, —$CH(R_5)OA_1$ and —$CH_2NH$—X'—$R_6$ wherein $A_1$ is —$C(=O)OR_6$, —$C(=O)R_6$ or —$C(=O)NR_5R_6$; X' is selected from the group consisting of —$S(O)_2$—, —$S(O)_2$—$N(R")$—, —$(C=O)$—, —$C(=O)$—$O$—, —$C(=O)$—$NH$—, —$P(O)(R")$—, and a direct link, wherein R" is hydrogen, alkyl of 1 to about 4 carbon atoms, aryl of about 6 to about 14 carbon atoms or aralkyl of about 7 to about 16 carbon atoms with the proviso that when X' is —$P(O)(R")$—, then R" is not hydrogen; $R_5$ is selected from the group consisting of:
  (1) alkyl of 1 to about 4 carbon atoms, optionally substituted with $Y_1$ and/or $Y_2$,
  (2) alkyl of 1 to about 3 carbon atoms substituted with cycloalkyl of 3 to about 6 carbon atoms, which is optionally mono-, di-, or tri-substituted on the ring with $Y_1$, $Y_2$, and/or $Y_3$,
  (3) cycloalkyl of 3 to about 6 carbon atoms, which is optionally mono-, di-, or trisubstituted on the ring with $Y_1$, $Y_2$, and/or $Y_3$,
  (4) heterocycloalkyl of 4 to about 6 ring atoms with the ring atoms selected from carbon and heteroatoms, wherein the heteroatoms are selected from the group consisting of oxygen, nitrogen, and $S(O)_i$, wherein i is 0, 1 or 2, which is optionally mono-, di-, or tri-substituted on the ring with $Y_1$, $Y_2$, and/or $Y_3$,
  (5) heterocyclo of 4 to about 6 ring atoms with the ring atoms selected from carbon and heteroatoms, wherein the heteroatoms are selected from the group consisting of oxygen, nitrogen, and $S(O)_i$, wherein i is 0, 1, or 2, including

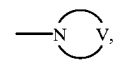

wherein

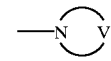

is a 5 to 6 member heterocycle having 3 to 5 ring carbon atoms, where V is —$CH_2$—, —$O$—, —$S(=O)$—, —$S(O)_2$— or —$S$—, which is optionally mono-, di-, or tri-substituted on the ring carbons with $Y_1$, $Y_2$, and/or $Y_3$,
  (6) alkenyl of 2 to about 6 carbon atoms which is optionally substituted with cycloalkyl of 3 to about 6 carbon atoms, which is optionally mono-, di-, or tri-substituted on the ring with $Y_1$, $Y_2$, and/or $Y_3$,
  (7) phenyl which is optionally mono-, di- or tri-substituted with $Y_1$, $Y_2$, and/or $Y_3$,
  (8) heteroaryl of about 5 to about 6 ring atoms with the ring atoms selected from carbon and heteroatoms, wherein the heteroatoms are selected from oxygen, nitrogen, and sulfur, and which is optionally mono-, di- or tri-substituted with $Y_1$, $Y_2$, and/or $Y_3$, (9) alkyl of 1 to about 4 carbon atoms substituted with phenyl and which is optionally mono-, di-, or tri-substituted on the phenyl ring with $Y_1$, $Y_2$, and/or $Y_3$,

(10) heteroaralkyl of about 5 to about 6 ring atoms with the ring atoms selected from carbon and heteroatoms, wherein the heteroatoms are selected from oxygen, nitrogen, and sulfur, and which is optionally substituted on the alkyl chain with hydroxy or halogen and optionally mono-, di- or tri-substituted on the ring with $Y_1$, $Y_2$, and/or $Y_3$,

(11) aralkenyl of about 8 to about 12 carbon atoms which is optionally mono-, di-, or tri-substituted on the aryl ring with $Y_1$, $Y_2$, and/or $Y_3$,

(12) heteroaralkenyl of about 5 to about 6 ring atoms with the ring atoms selected from carbon and heteroatoms, wherein the heteroatoms are selected from oxygen, nitrogen, and sulfur, and which is optionally mono-, di- or tri-substituted on the ring carbons with $Y_1$, $Y_2$, and/or $Y_3$, and

(13) hydrogen; and $R_6$ is selected from the group consisting of:
(1) alkyl of 1 to about 12 carbon atoms, optionally substituted with $Y_1$ and/or $Y_2$,
(2) alkyl of 1 to about 3 carbon atoms substituted with cycloalkyl of 3 to about 8 carbon atoms, which is optionally mono-, di-, or tri-substituted on the ring with $Y_1$, $Y_2$, and/or $Y_3$,
(3) cycloalkyl of 3 to about 15 carbon atoms, which is optionally mono-, di-, or trisubstituted on the ring with $Y_1$, $Y_2$, and/or $Y_3$,
(4) heterocycloalkyl of 4 to about 10 ring atoms with the ring atoms selected from carbon and heteroatoms, wherein the heteroatoms are selected from the group consisting of oxygen, nitrogen, and $S(O)_i$, wherein i is 0, 1 or 2, which is optionally mono-, di-, or tri-substituted on the ring with $Y_1$, $Y_2$, and/or $Y_3$,
(5) heterocyclo of 4 to about 10 ring atoms with the ring atoms selected from carbon and heteroatoms, wherein the heteroatoms are selected from the group consisting of oxygen, nitrogen, and $S(O)_i$, wherein i is 0, 1, or 2, including

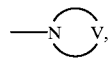

wherein

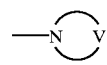

is a 5 to 7 member heterocycle having 3 to 6 ring carbon atoms, where V is $-CH_2-$, $-O-$, $-S(=O)-$, $-S(O)_2-$ or $-S-$, which is optionally mono-, di-, or tri-substituted on the ring carbons with $Y_1$, $Y_2$, and/or $Y_3$,
(6) aryl of about 6 to about 14 carbon atoms which is optionally mono-, di- or tri-substituted with $Y_1$, $Y_2$, and/or $Y_3$,
(7) heteroaryl of about 5 to about 14 ring atoms with the ring atoms selected from carbon and heteroatoms, wherein the heteroatoms are selected from oxygen, nitrogen, and sulfur, and which is optionally mono-, di- or tri-substituted with $Y_1$, $Y_2$, and/or $Y_3$, (8) aralkyl of about 7 to about 15 carbon atoms which is optionally mono-, di-, or tri-substituted on the aryl ring with $Y_1$, $Y_2$, and/or $Y_3$,
(9) heteroaralkyl of about 5 to about 14 ring atoms with the ring atoms selected from carbon and heteroatoms, wherein the heteroatoms are selected from oxygen, nitrogen, and sulfur, and which is optionally substituted on the alkyl chain with hydroxy or halogen and optionally mono-, di- or tri-substituted on the ring with $Y_1$, $Y_2$, and/or $Y_3$, and
(10) hydrogen with the proviso that $R_6$ is not hydrogen when $A_1$ is $-C(=O)OR_6$;

(d) $R_3$ is selected from H or methyl, or $R_3$ and $R_4$ are selected together as set forth in (f);

(e) $R_4$ is in the S configuration and is selected from the group consisting of H, $-CH_2-S-CH_3$, $-CH_2OH$, $-CH_2CN$, lower alkyl of 1 to about 3 carbon atoms, $-CH_2C\equiv CH$, $-CH_2CH=CH_2$ and $-CH=CH_2$ or $R_3$ and $R_4$ are selected together as set forth in (f);

(f) alternatively, $R_3$ and $R_4$ are selected together to be in the S configuration to give a group at P2 selected from the group consisting of prolyl, pipecolyl, azetidine-2-carbonyl, 4-hydroxyprolyl, 3-hydroxyprolyl, 3,4-methanoprolyl, and 3,4-dehydroprolyl;

(g) $R_7$ is hydrogen or alkyl of 1 to about 4 carbon atoms; and (h) E is selected from

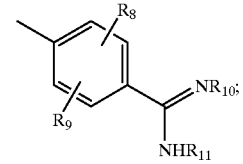

(1)

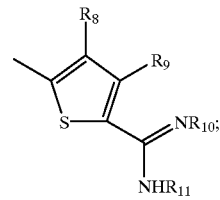

(2)

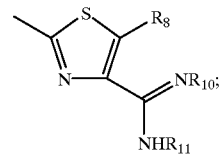

(3)

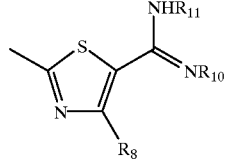

(4)

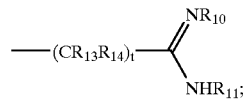

(5)

(6) 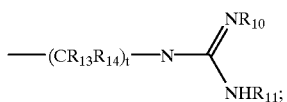

(7) 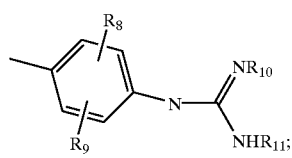

(8) 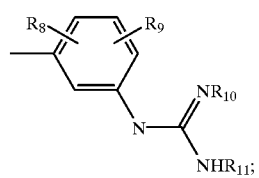

(9) 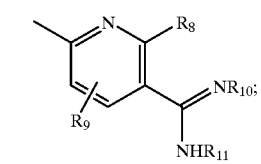

(10) 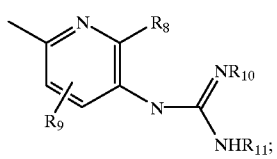

(11) 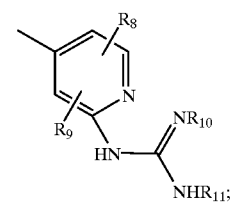

(12) 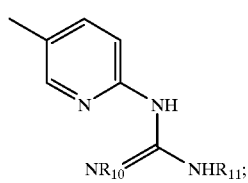

(13) 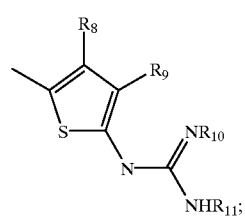

(14) 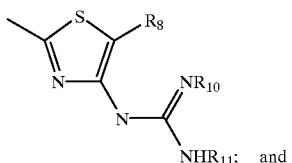

(15) 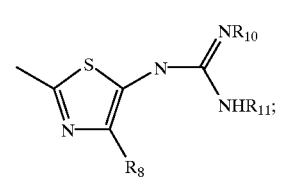

wherein $R_8$ and $R_9$ are independently selected from hydrogen, hydroxy, halogen, alkyl of 1 to about 4 carbon atoms, alkyl of 1 to about 4 carbon atoms substituted with alkoxy of 1 to about 4 carbon atoms, alkoxy of 1 to about 6 carbon atoms, and trifluoromethyl; $R_{10}$ and $R_{11}$ are independently hydrogen, hydroxy, alkoxy of 1 to about 3 carbon atoms, trihydrocarbylsilyl of 3 to about 16 carbon atoms, alkyl of 1 to about 3 carbon atoms or —C(=O)$R_{12}$; $R_{12}$ is hydrogen, alkyl of 1 to about 6 carbon atoms, alkoxy of 1 to about 6 carbon atoms or $(CF_2)_jCF_3$ wherein j is 0, 1, 2 or 3 with the proviso that $R_{10}$ and $R_{11}$ are not both hydroxy or alkoxy; each of $R_{13}$ and $R_{14}$ is independently selected from hydrogen or lower alkyl of 1 to about 3 carbon atoms; and t is an integer from 0 to 6; and pharmaceutically acceptable salts thereof.

Preferred X groups include —S(O)$_2$—, —OC(=O)—, —NH—C(=O)—, and a direct link. Especially preferred are —S(O)$_2$— and —OC(=O)—.

Preferred $R_1$ groups include alkyls, especially isobutyl, 2-ethylhexyl, methyl, n-butyl, isopropyl, cyclohexylmethyl, and cyclohexylpropyl; cycloalkyl, especially (−)menthyl, (+)menthyl, and cyclohexyl; aryls, especially naphthyl and phenyl; aralkyls, especially benzyl, 3-phenylpropyl, and 2-phenylethyl; and fused carbocyclic alkyls, especially fluorenylmethyl. Especially preferred $R_1$ groups include phenyl, benzyl, 2-phenylethyl, isobutyl, n-butyl and 3-phenylpropyl.

Preferred combinations of $R_1$—X— include phenyl-S(O)$_2$—, benzyl-S(O)$_2$—, 2-phenylethyl-S(O)$_2$—, 3-phenylpropyl-S(O)$_2$—, n-butyl-S(O)$_2$—, benzyl-OC(=O)—, and isobutyl-OC(=O)—.

Preferred $R_2$ groups include —CH$_3$, —C$_2$H$_5$, —CH$_2$NH—X'—R$_5$ and —CH(R$_5$)OH, wherein $R_5$ is hydrogen, alkyl, especially methyl, or aralkyl. Preferred chirality at the alpha carbon is R. When chiral, preferred chirality at the beta carbon is R. Preferred $R_2$ groups are those that define the $P_3$ position as d-seryl (—CH(R$_5$)OH where $R_5$ is H), (R,R)d-allothreonyl (—CH(R$_5$)OH where $R_5$ is methyl), d-2-aminobutyryl, N-β-methyloxycarbonyl-d-2,3-diaminopropionyl (—CH$_2$NH—X'—R$_5$ where $R_5$ is CH$_3$ and X' is (—C=O)O—), N-β-(2-phenylethylcarbonyl)-d-2,3-diaminopropionyl (—CH$_2$NH—X—R$_5$ where $R_5$ is 2-phenylethyl and X' is —(C=O)—), N-β-benzyloxycarbonyl-d-2,3-diaminopropionyl (—CH$_2$NH—X'—R$_5$ where $R_5$ is benzyl and X' is —(C=O)O—) and d-alanyl(—CH$_2$). Especially preferred $R_2$ groups are those which define $P_3$ as d-seryl ($R_5$ is H) or (R,R)d-allothreonyl ($R_5$ is methyl).

Alternate preferred $R_2$ groups include —$(CH_2)_2OA_1$ and —$CH(R_5)OA_1$, more preferably —$CH(R_5)OA_1$; preferably $R_5$ is H. More preferably $R_2$ is selected so that $P_3$ is defined as an acyl or carbonate ester of d-seryl. Compounds wherein $R_2$ is —$(CH_2)_2OA_1$ or —$CH(R_5)OA_1$ may act as prodrugs.

A preferred $R_3$ group, when $R_3$ and $R_4$ are not selected together, is hydrogen. A preferred $R_4$ group, when $R_3$ and $R_4$ are not selected together, is methyl, vinyl, allyl or propargyl. When $R_3$ and $R_4$ are selected together, prolyl, 3-hydroxyprolyl, 4-hydroxyprolyl, 3,4-dehydroprolyl, 3,4-methanoprolyl, and azetidine-2-carbonyl- are preferred selections to define a group at P2.

Preferred $R_7$ groups include hydrogen.

Preferred E groups include 4-amidinophenyl, 4-guanidinophenyl, 3-amidinopropyl, and 5-(2-amidinothienyl).

Among the compounds of the present invention, preferred compounds include those having an $R_2$ element that defines d-serine or d-allothreonine or an acyl or carbonate ester thereof at the P3 position of the compound and an amidinophenyl, guanidinophenyl or amidinothienyl group at P1. Especially preferred are such compounds also having either i) a hydrogen at $R_3$ and methyl at $R_4$ (P2 is alanine), or ii) having $R_3$ and $R_4$ selected together so that P2 is prolyl, azetidine-2-carbonyl, 3,4-methanoprolyl or 3,4-dehydroprolyl.

Preferred compounds of the present invention include those depicted in FIGS. 10A to 10F. Especially preferred are Compounds D, F, I, J, K, L, O, R, T, U, V, AE, AH, AJ, AN and AV of FIGS. 10A to 10F.

Also especially preferred are the followng compounds of formula (I): compounds AX (X=S(O)$_2$, $R_1$=4-chlorobenzyl, $R_2$=—$CH_2OH$, $R_3$=H, $R_4$=$CH_3$, $R_7$=H and E=4-amidinophenyl), AY (X=SO$_2$, $R_1$=3-chlorobenzyl, $R_2$=—$CH_2OH$, $R_3$=H, $R_4$=$CH_3$, $R_7$=H and E=4-amidinophenyl) and AZ (X=SO$_2$, $R_1$=2-fluorobenzyl, $R_2$=—$CH_2OH$, $R_3$=H, $R_4$=$CH_3$, $R_7$=H and E=4-amidinophenyl).

2. Preparation of Preferred Compounds

FIGS. 1 to 5 depict synthetic schemes for synthesis of intermediates which may be used in preparation of certain compounds of the present invention.

FIG. 1 depicts solution phase synthesis of intermediates useful in the preparation of compounds of the present invention. See Examples 60 to 62. See also Examples 95 to 97.

Examples 63 to 66, 67 to 70 and 71 to 73 describe solution phase syntheses of intermediates useful in the synthesis of compounds of the present invention.

Figure 2:
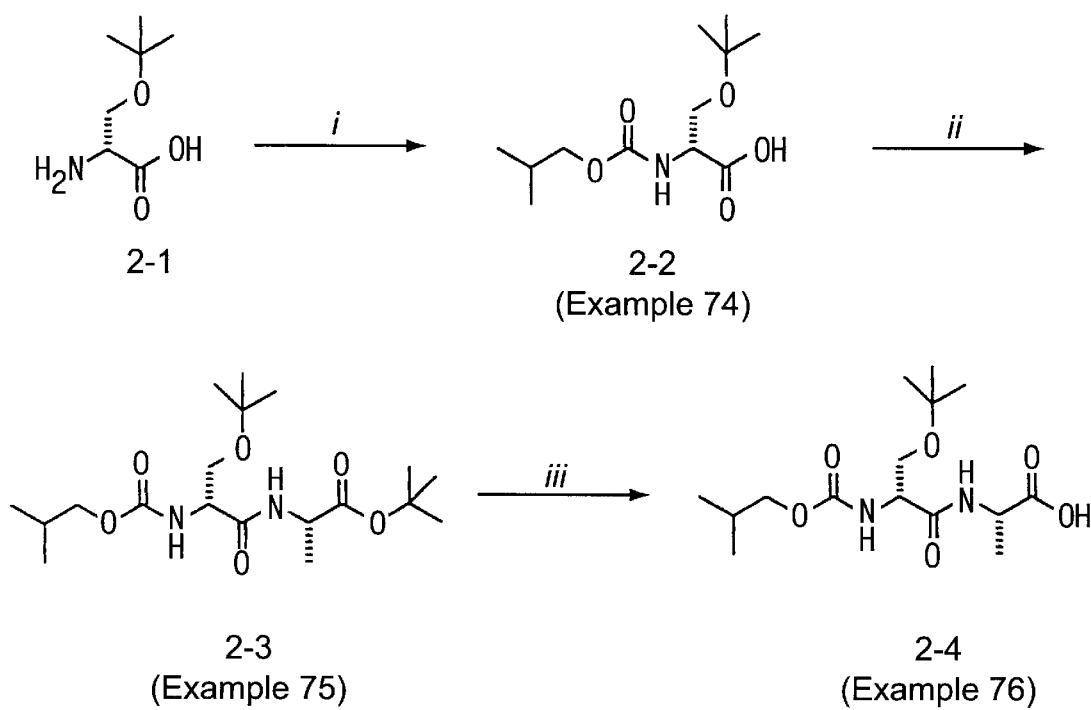
FIG. 2 depicts a reaction scheme for a solution phase synthetic route which may be used to prepare an intermediate useful in the preparation of a compound of the present invention. In this figure, "i" through "iii" are defined as: i) isobutyl chloroformate, sodium carbonate, water, 99.5% yield after workup; ii) alanine t-butyl ester, hydrochloride salt, EDC, and hydroxybenzotriazole in acetonitrile; diisopropylethylamine, quantitative yield after workup; and iii) TFA, DCM, quantitative yield after workup. See also Examples 74 to 76.
Figure 3:
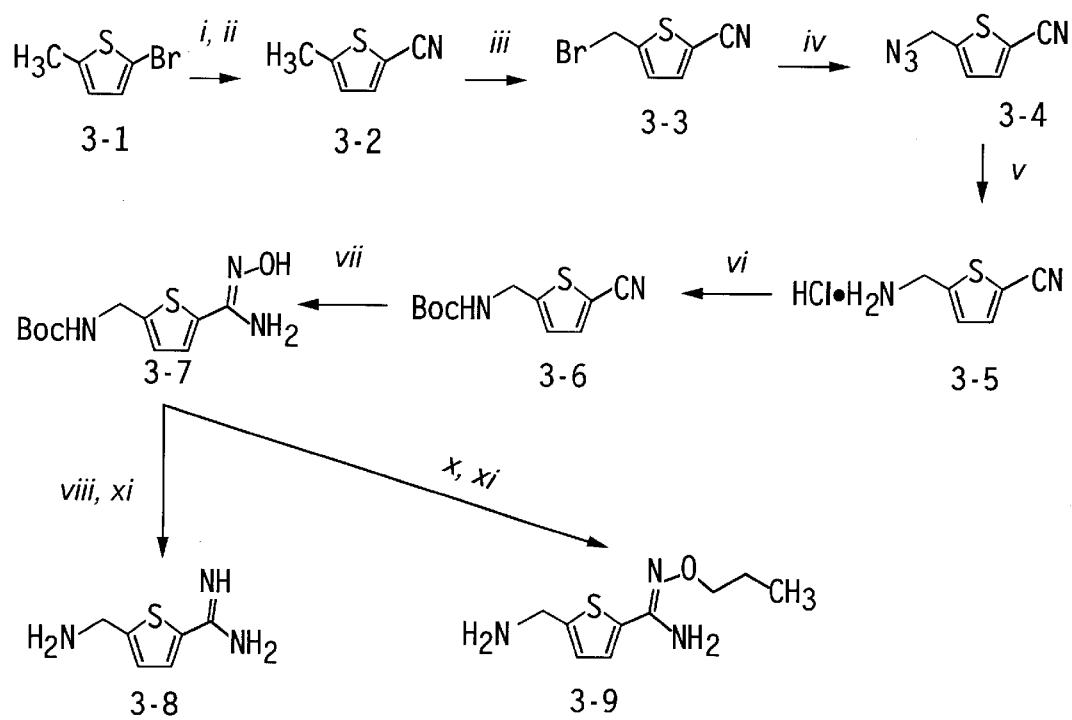
FIG. 3 depicts a reaction scheme for the synthesis of intermediates which may be used in the preparation of compounds of the present invention. In this figure, "i" through "xi" are defined as follows: i) CuCN, DMF, reflux (4 hours); ii) EtOAc, 10% aqueous NaCN; iii) N-bromosuccinimide, 2,2'-azo-bisisobutyronitrile, CCl$_4$, reflux (5 hours); iv) NaN$_3$, DMF; v) triphenylphosphine, THF, water, O C, stirring (10 hours); vi) K$_2$CO$_3$, Boc$_2$O, water, dioxane; vii) hydroxylamine HCl, NMM, MeOH; viii) 10% Pd/C, MeOH, 45 psi H$_2$ (10 hours); ix) 4M HCl in dioxane; x) CsCO$_3$, iodopropane in DMF; and xi) 4M HCl, dioxane, 3 hours, room temperature.
Figure 4:
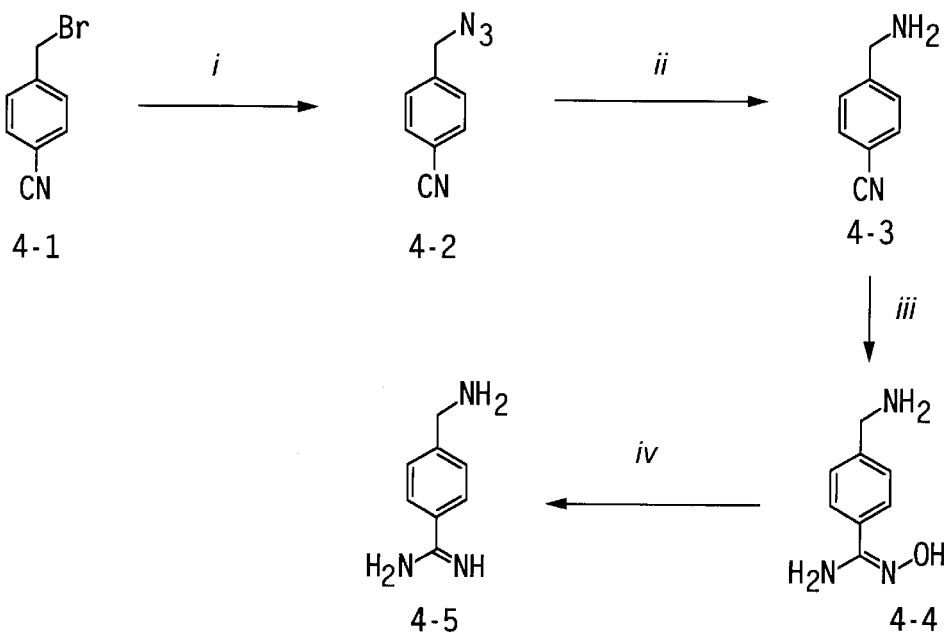
FIG. 4 depicts a reaction scheme for the synthesis of intermediates which may be used in the preparation of compounds of the present invention. In this figure, "i" through "iv" are defined as follows: i) NaN$_3$, DMF; ii) 10% Pd/C, EtOAc, 45 psi H$_2$ (11 hours); iii) hydroxylamine HCl, NMM, MeOH; and iv) 10% Pd/C, MeOH, 45 psi H$_2$ (48 hours).
Figure 5:
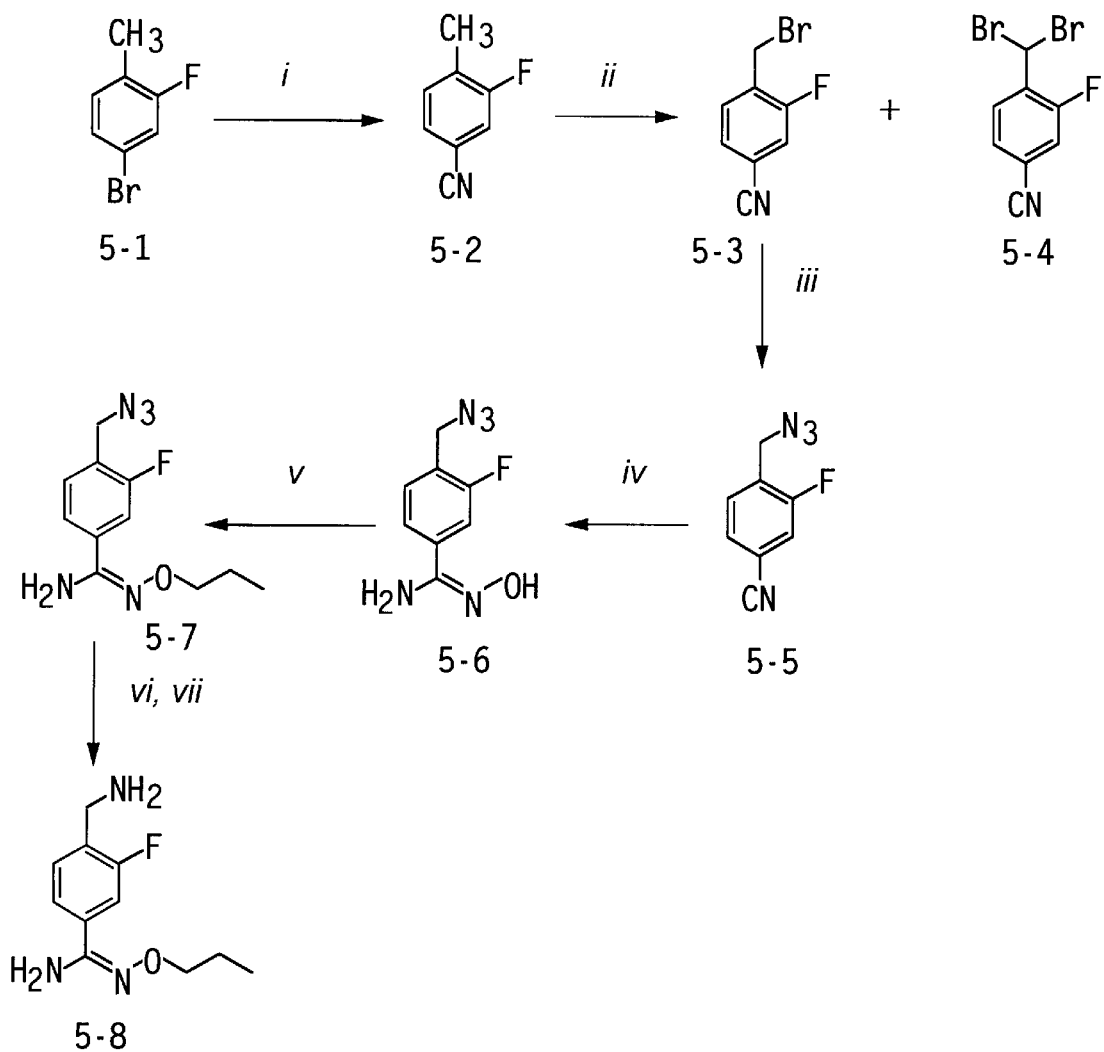
FIG. 5 depicts a reaction scheme for the synthesis of intermediates which may be used in the preparation of compounds of the present invention. In this figure, "i" through "vii" are defined as follows: i) Cu(I)CN, DMF; ii) NBS, benzoylperoxide, CCl$_4$, 80° C. (14 hours); iii) NaN$_3$, DMF, stirring (20 hours); iv) hydroxylamine HCl, NMM, MeOH, stirring (3 days); v) CsCO$_3$, iodopropane, DMF, 50° C. (20 hours); vi) triphenylphosphine, THF, stirring (20 hours); and vii) 3M NaOH to pH 14.

FIG. 2 depicts an alternate synthetic route to prepare an intermediate useful in the preparation of compounds of the present invention using solution phase synthesis. See also Examples 74 to 76.

Figure 6:
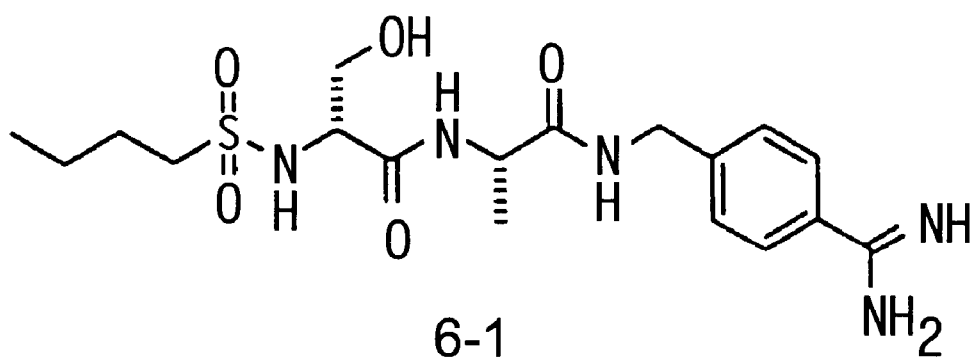
FIG. 6 depicts a reaction scheme for the synthesis of a compound of the present invention where R$_2$ is —CH$_2$OA$_1$ and A$_1$ is —C(=O)R$_6$, using as an intermediate, compound of Example 9. In this figure, "i" is defined as: i) pyridine, R$_6$COCl.
Figure 6:
Figure 6:
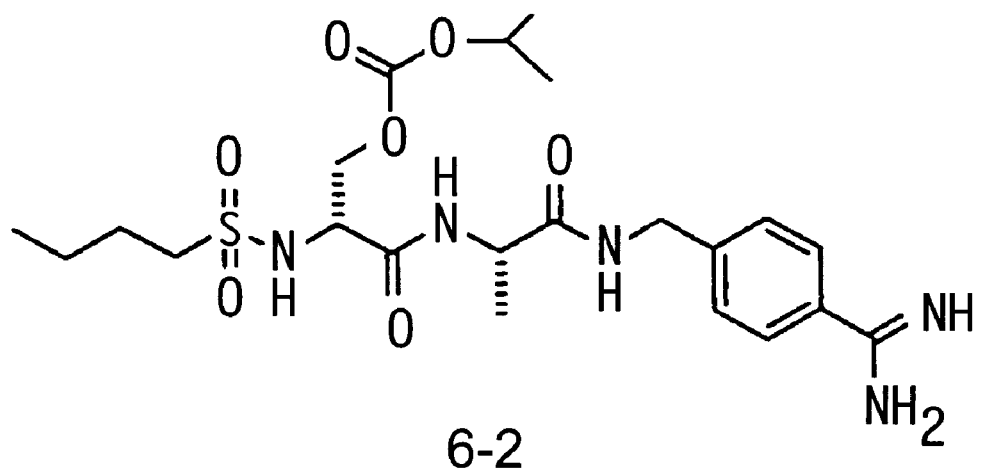

FIG. 6 depicts a reaction scheme for the preparation of a compound of the present invention having an esterified hydroxyl at P3.

Figure 7:
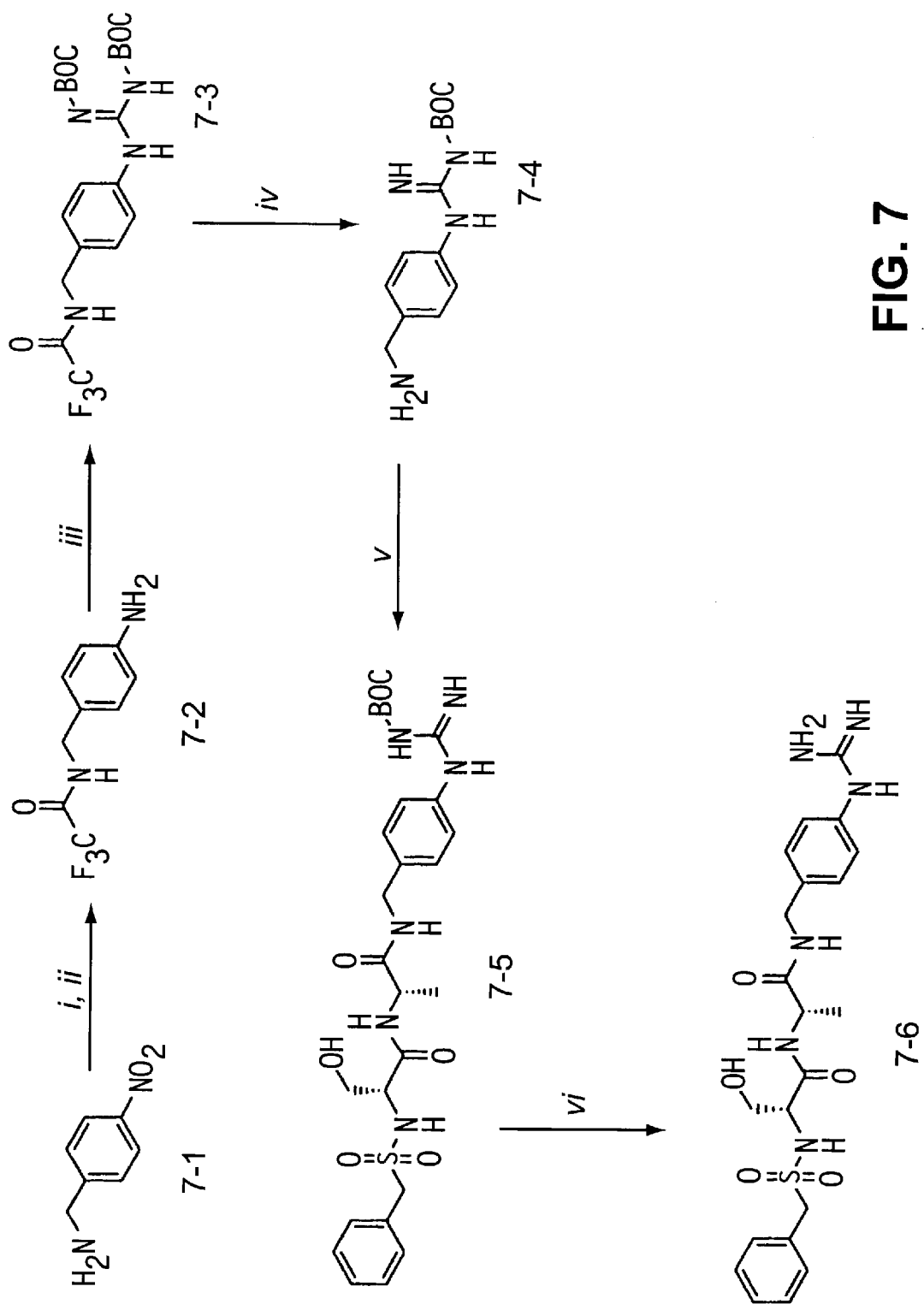
FIG. 7 depicts a reaction scheme for the synthesis of certain compounds of the present invention. In this figure, "i" through "vi" are defined as follows: i) trifluoracetic anhydride, 0° C., stir overnight; ice, CH$_2$Cl$_2$, Na$_2$SO$_4$; ii) Pd/C (10%) in MeOH (overnight); iii) N-N'-di-Boc-N"-trifluoromethanesulfonyl-guanidine, TEA, CH$_2$Cl$_2$, 6 hours; HCl, brine, Na$_2$SO$_2$; column chromatography (CH$_2$Cl$_2$/MeOH 99:1); iv) potassium carbonate, H$_2$O/MeOH (2:15), overnight; CH$_2$Cl$_2$/MeOH (9:1), Na$_2$SO$_4$; v) benzylsulfonyl-D-serine-L-alanine carboxylate, HATU, HOAT, DIEA, Acetonitrile, overnight; EtOAc, HCl, NaHCO$_3$, brine; HPLC (CH$_3$CN, H$_2$O, 0.1% TFA); vi) CH$_2$Cl$_2$/TFA (1:1), 90 minutes; HPLC (CH$_3$CN, H$_2$O, 0.1% TFA).

FIG. 7 depicts a reaction scheme for the preparation of a compound of the present invention having a 4-guanidinophenyl at P1.

Figure 8:
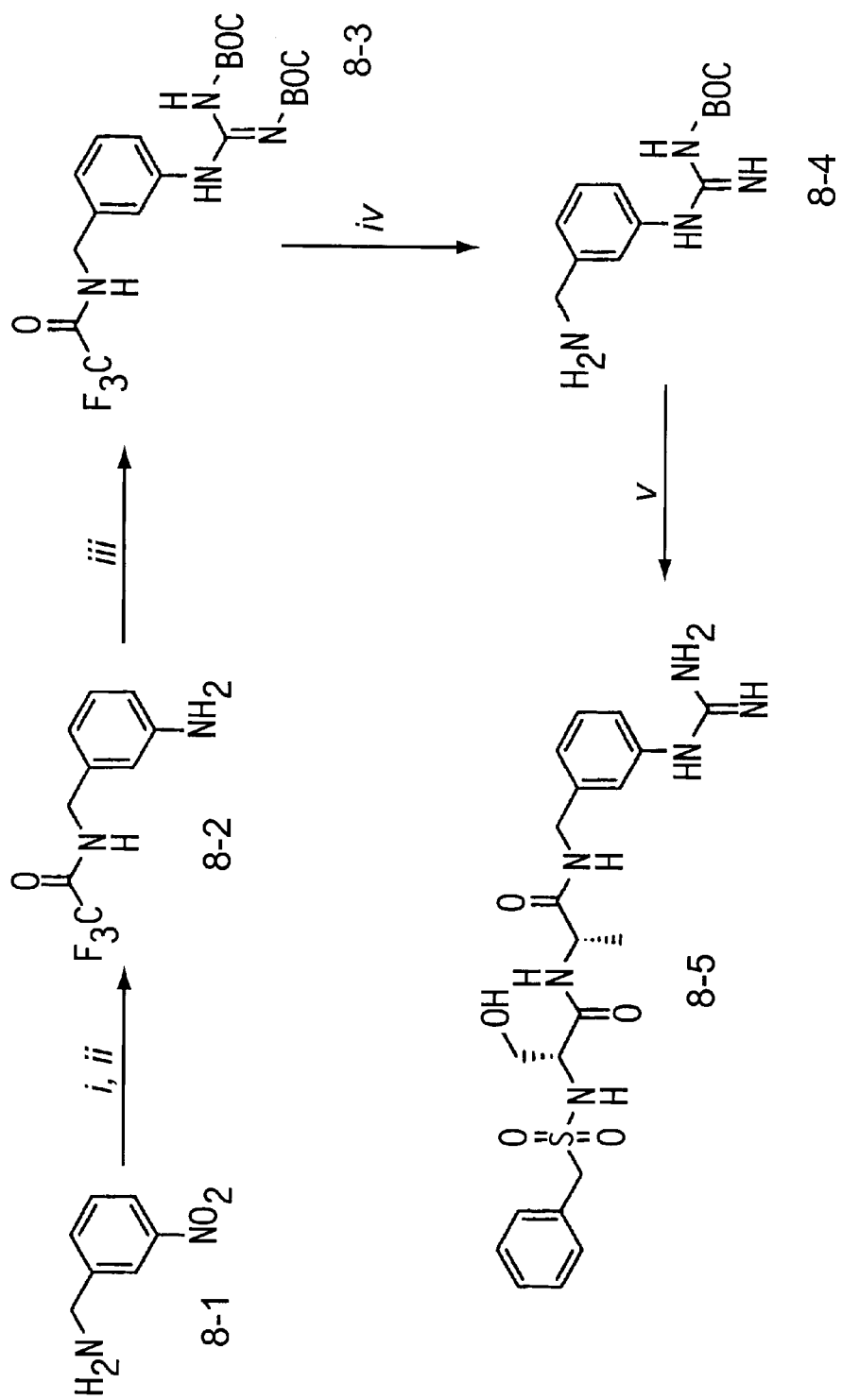
FIG. 8 depicts the reaction scheme for the synthesis of certain compounds of the present invention. In this figure "i" throught "vi" are defined as: i) trifluoroacetic anyhydride, stir overnight; ice, CH$_2$Cl$_2$, Na$_2$SO$_4$; ii) Pd/C (10%) in MeOH (overnight); iii) N-N'-Boc-N"-trifluoromethane-sulfonyl-guanidine, TEA, CH$_2$Cl$_2$, 24 hours; HCl, brine, Na$_2$SO$_4$; column chromatography (CH$_2$Cl$_2$/MeOH 98:2); iv) potassium carbonate, H$_2$O/MeOH (1:1), overnight; H$_2$O, CH$_2$Cl$_2$/MeOH (9:1), Na$_2$SO$_4$; and v) benzylsulfonyl-D-serine-L-alanine carboxylate, HATU, HOAT, DIEA, in acetonitrile, room temperature overnight; EtOAc, HCl, NaHCO$_3$, brine; CH$_2$Cl$_2$/TFA (1:1), room temperature, 2 hours, HPLC (CH$_3$CN, H$_2$O, 0.1% TFA).

FIG. 8 depicts a reaction scheme for the preparation of a compound of the present invention having a 3-guanidinophenyl at P1.

Figure 9:
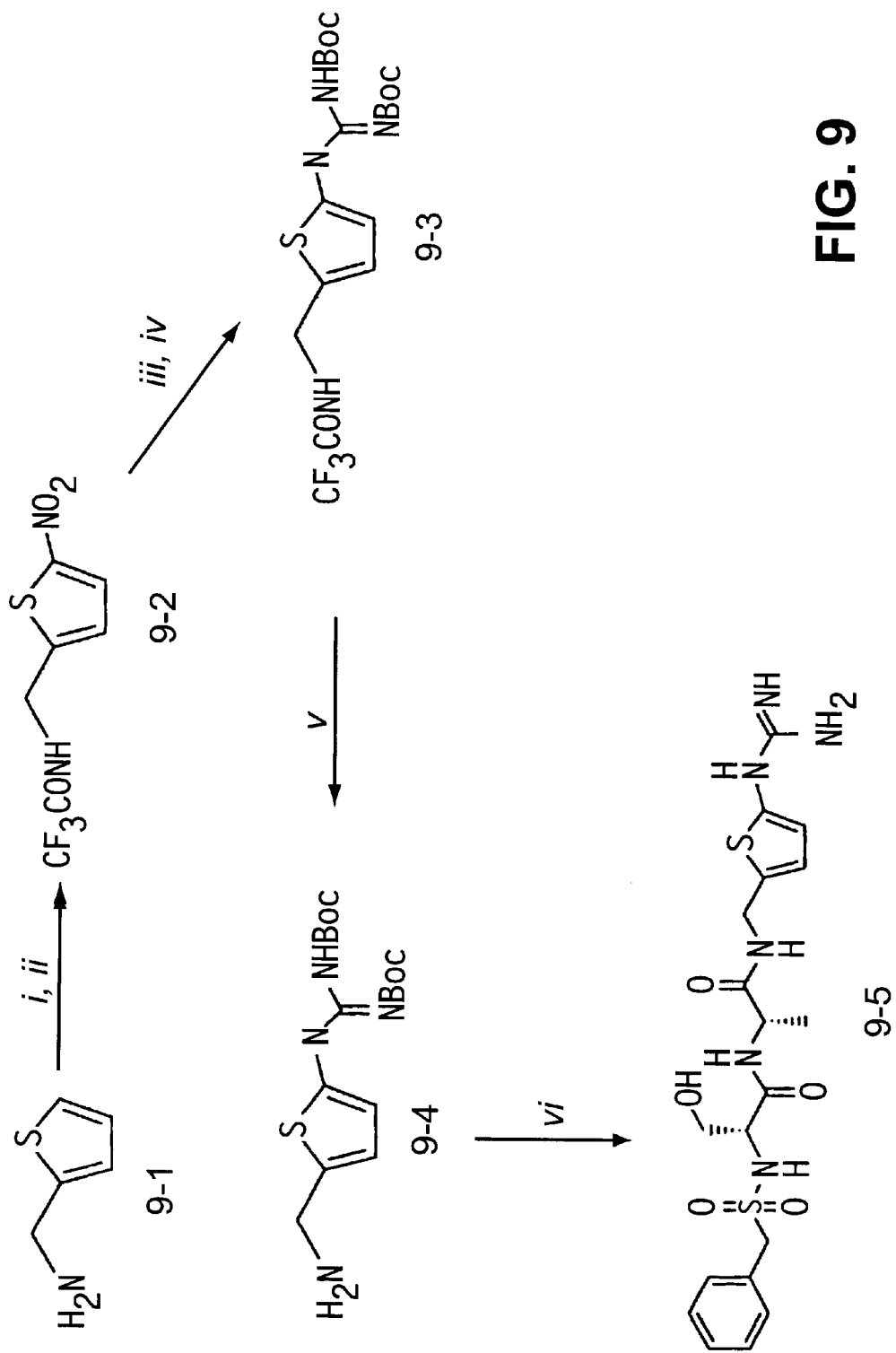
FIG. 9 depicts a reaction scheme for the synthesis of a compound of the present invention. In this figure, "i" through "vi" are defined as follows: i) trifluoroacetic anhydride, 0° C., one hour; ii) KNO$_3$, -20° C., stir overnight; CH$_2$Cl$_2$, Na$_2$SO$_4$, column chromatography; iii) HCl in MeOH, 0° C., SnCl$_2$, stir 30 minutes, NaHCO$_3$, CH$_2$Cl$_2$, Na$_2$SO$_4$; iv) N$_1$N'-di-Boc-N"-trifluoromethanesulfonyl-guanidine, TEA, CH$_2$Cl$_3$, stirring 24 hours; HCl (1M), brine, Na$_2$SO$_4$, column chromatography; v) K$_2$CO$_3$, H$_2$O/MeOH (1:1), stir overnight; H$_2$O, CH$_2$Cl$_2$/MeOH (95:5), Na$_2$SO$_4$; and vi) benzylsulfonyl-D-serine-L-alanine carboxylate, HATU, HOAT, DIEA, AcN, stir overnight; EtOAc, HCl (1M), aqueous NaHCO$_3$, brine, Na$_2$SO$_4$; HPLC.
Figure 10A:
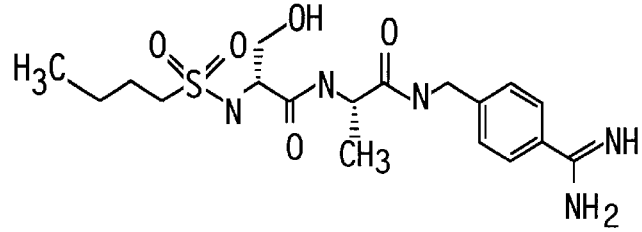
Figure 10A:
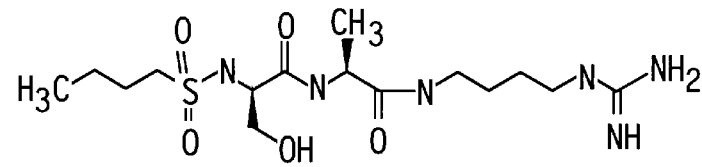
Figure 10A:
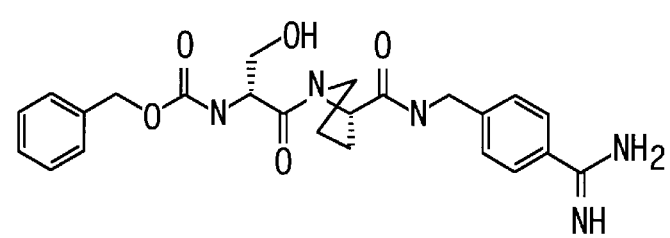
Figure 10A:
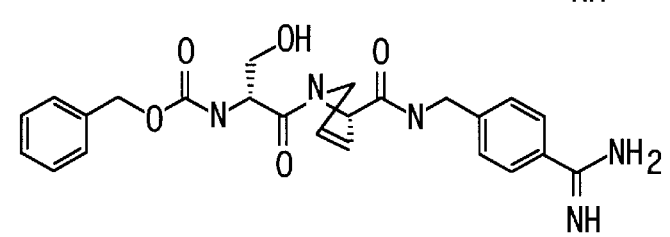
Figure 10A:
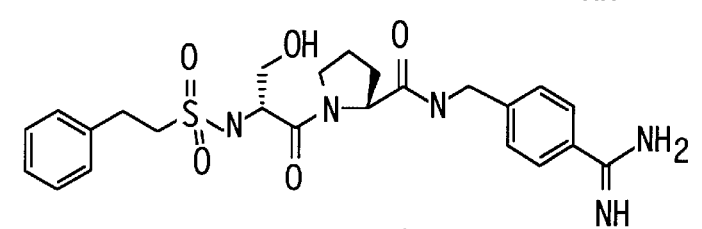
Figure 10A:
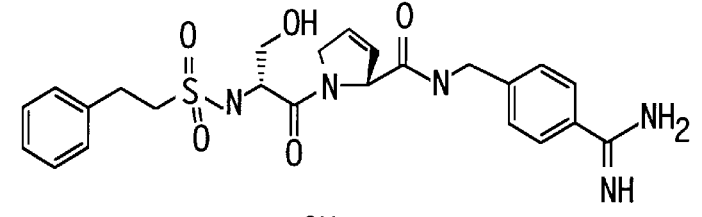
Figure 10A:
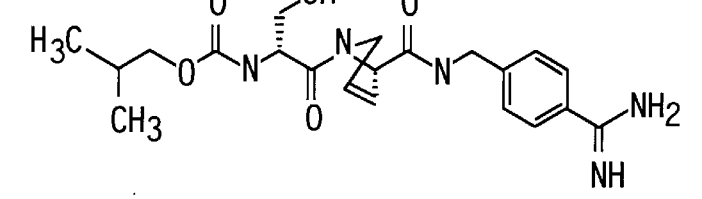
Figure 10B:
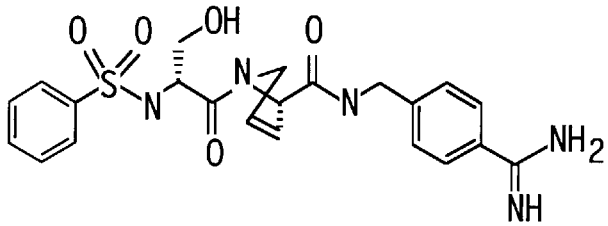
Figure 10B:
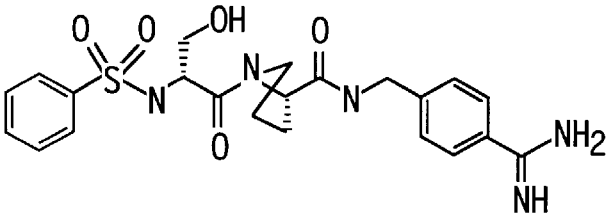
Figure 10B:
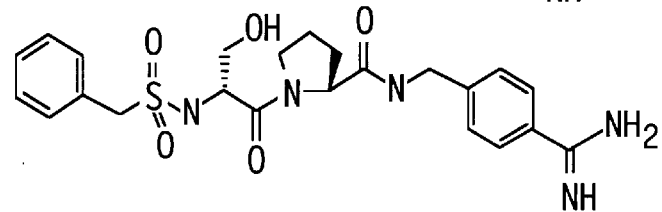
Figure 10B:
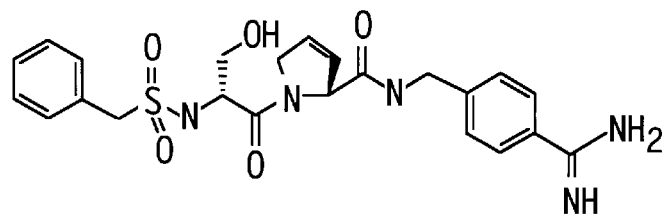
Figure 10B:
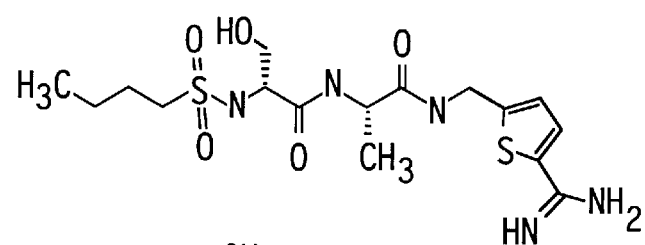
Figure 10B:
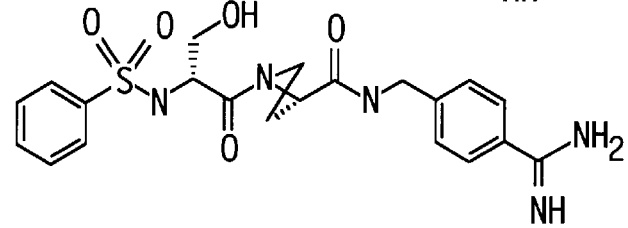
Figure 10C:
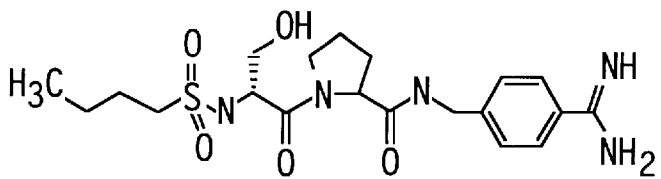
Figure 10C:
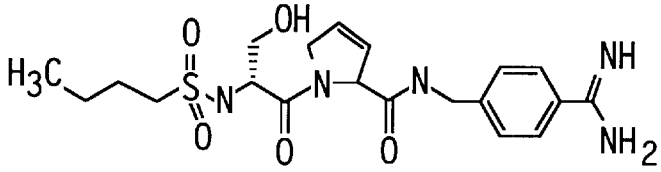
Figure 10C:
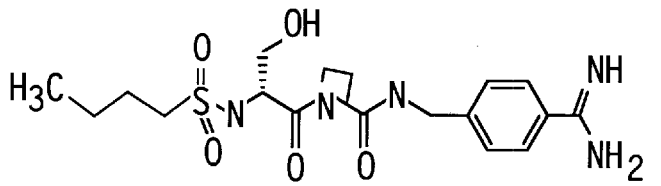
Figure 10C:
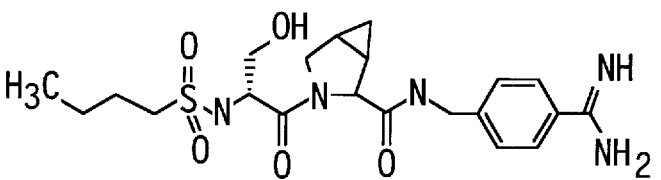
Figure 10C:
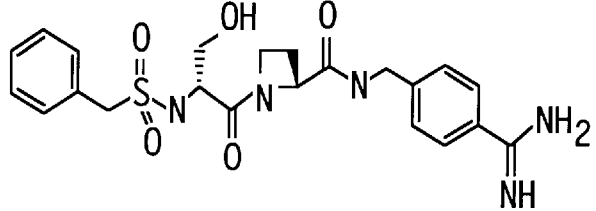
Figure 10C:
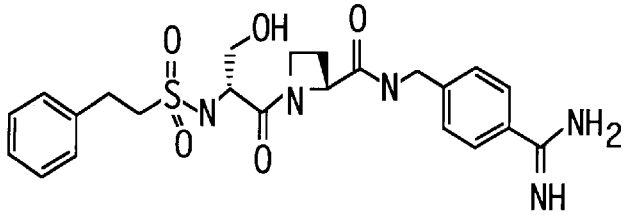
Figure 10D:
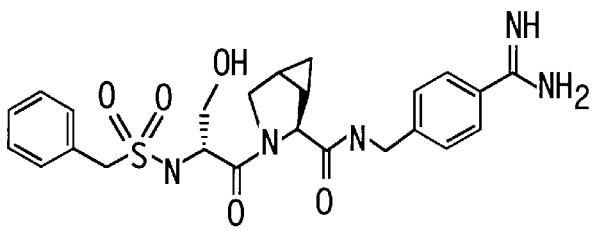
Figure 10D:
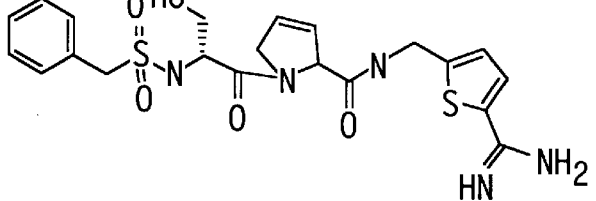
Figure 10D:
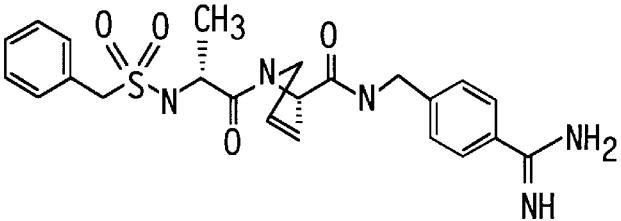
Figure 10D:
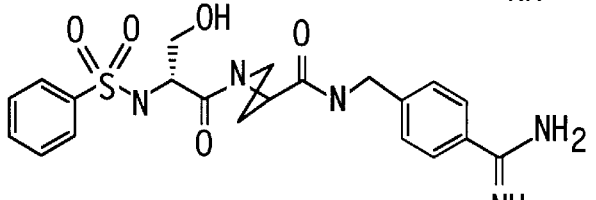
Figure 10D:
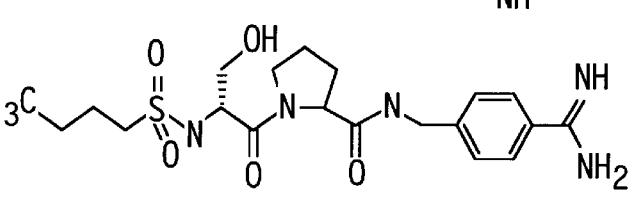
Figure 10D:
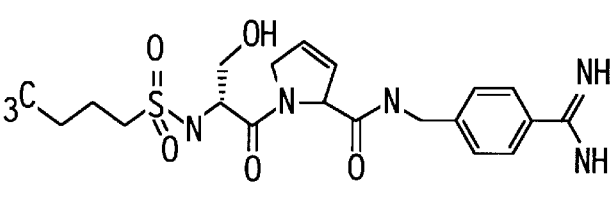
Figure 10D:
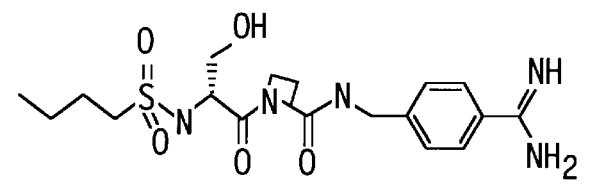

FIG. 9 depicts a reaction scheme for the preparation of a compound of the present invention having 2-guanidinothiophenyl at P1.

Figure 11:
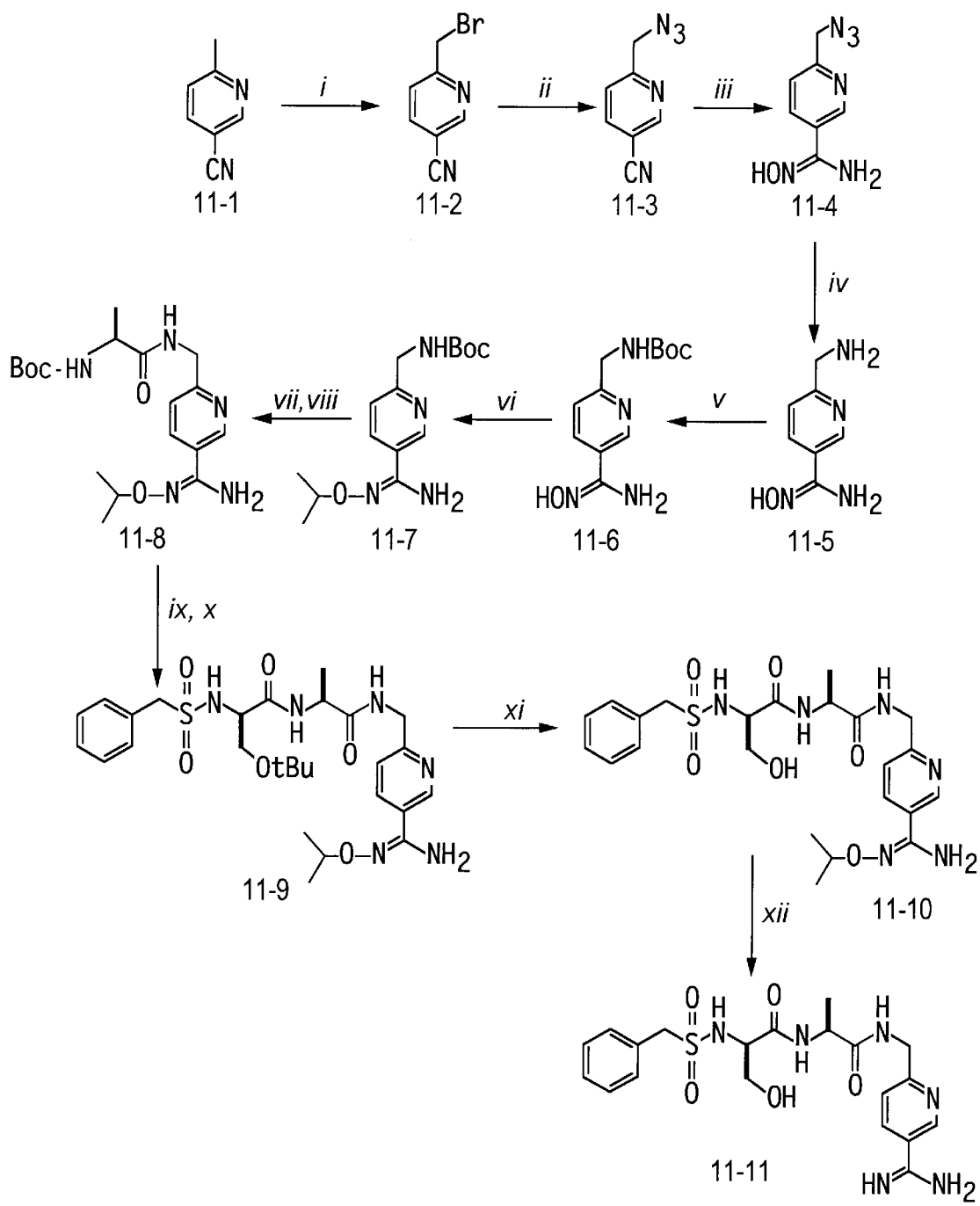
FIG. 11 depits a reaction scheme for the synthesis of a compound of the present invention. In this figure, "i" through "xii" are defined as follows: i) CCl$_4$, N-bromosuccinimide; N$_2$, AIBN, stirring, flash chromatography; ii) DMF, NaN$_3$, stir overnight, diethylether, water, brine, MgSO$_4$, filter; (iii) MeOH, TEA, 65° C., 4 hours; EtOAc, H$_2$O, brine, MgSO$_4$; iv) THF/water, Ph$_3$P, stir overnight; 1N HCl, H$_2$O, DCM, ph~9; v) dioxane/water, K$_2$CO$_3$, Boc$_2$O, stir overnight; EtOAc, aqueous NAHCO$_3$, brine, Na$_2$SO$_4$, flash column chromatography; vi) DMF, 2-iodopropane, CsCO$_3$; EtOAc, aqueous NaHCO$_3$, Na$_2$SO$_4$, flash column chromatography; vii) dioxane, 4N HCl in dioxane, solvent removal; viii) AcN, DIEA; Boc-alanine, EDC, HOBt, stir overnight; EtOAc, aqueous NAHCO$_3$, brine, Na$_2$SO$_4$, flash column chromatography; ix) dioxane, 4N HCl in dioxane, remove solvent, x) AcN, DIEA, BnSO$_2$-dSer(tBu)-OH, EDC, HOBt, stir overnight; EtOAc, aqueous NaHCO$_3$, brine, Na$_2$SO$_4$, RP-HPLC; xc) DCM, TFA; RP-HPLC; and xii) H$_2$O, HOAc, Zn dust; RP-HPLC.

FIG. 11 depicts a reaction scheme for the preparation of a compound of the present invention having a 3-amidinopyridyl at P1.

Preferred means of chemically coupling (as for example, amide bond function) include formation of a peptide bond by using conventional coupling reagents known in the art. See Bodanszky, N. *Peptide Chemistry*, pp. 55–73, Springer-Verlag, New York (1988) and references cited therein. The chemical coupling may be either by means of one-step or two-step coupling. In one-step coupling, the two coupling partners are coupled directly. Preferred coupling reagents for one-step coupling of the coupling partners include DCC with HOBt, EDC with HOBt, EDC with HOAt, HBTU or TBTU. In two-step coupling, an activated ester or anhydride of the C-terminal carboxy group of one coupling partner is formed prior to its coupling to the other coupling partner.

For preparation of certain compounds having hydrogenation-sensitive substituent groups, it is preferred to avoid the use of hydrogen gas with palladium on carbon. Another preferred method for preparing compounds of the present invention containing hydrogenation sensitive groups such as alkenyl or aryl moieties substituted with halogen, cyano, nitro, or —S—$Z_1$, is to use boron tris (trifluoroacetate), B(OCOCF$_3$)$_3$, to cleave the $N^g$-nitro of the arginine group. The reagent is prepared by the reaction of BBr$_3$ and CF$_3$COOH in dichloromethane at 0° C. The reagent is also commercially available. Generally, the $N^g$-nitro compound is treated with boron tris (trifluoroacetate) in trifluoroacetic acid at 0° C. See, e.g., Fieser, M. and Fieser, L. F., *Reagents for Organic Synthesis*, p. 46, John Wiley & Sons, New York (1974); Pless, J., and Bauer, W. *Angew. Chem., Internat. Ed.*, 12, 147 (1973).

In addition, another preferred reagent for selective nitro group cleavage is titanium trichloride. This reagent is commercially available. The $N^g$ nitro compound is treated with titanium trichloride in aqueous methanol containing an ammonium acetate buffer followed by exposure of the reaction mixture to air or dimethyl sulfoxide. See, e.g., Freidinger, R. M., Hirschmann, R., and Veber, D. F., *J. Org. Chem.*, 43, 4800 (1978).

FIG. 6 depicts a reaction scheme for the synthesis of a compound of the present invention where $R_2$ is —$CH_2OA_1$ and $A_1$ is —$C(=O)R_6$:

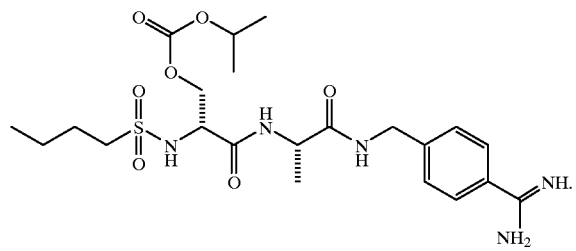

An intermediate such as 6-1 (the compound of Example 9) is reacted with an acid chloride $R_6COCl$ in the presence of a base such as pyridine. Compounds where $R_2$ is —$(CH_2)_2$ $OA_1$ or —$CH(R_5)OA_1$ where Al is —$C(=O)R_6$ may conveniently be prepared by reacting an appropriate intermediate corresponding to 6-1 with the appropriate acid chloride derivative, $R_6COCl$, preferably in the presence of a base such as pyridine.

Compounds where $R_2$ is —$(CH_2)_2OA_1$ or —$CH(R_5)OA_1$ wherein $A_1$ is —$C(=O)OR_6$ may be conveniently prepared by treating a corresponding compound where $R_2$ is —$(CH_2)_2OH$ or —$CH(R_5)OH$ with the appropriate chloroformate derivative. In the preparation of compounds having an amidino or guanidino group at $P_1$, it may be preferred to cap the P3 hydroxyl with the carbonate group prior to deprotecting the amidino or guanidino group. Accordingly, it is preferred to treat the corresponding intermediate with the chloroformate derivative. (See, e.g., Example 8). The product is then hydrogenated and optionally treated under hydrolysis conditions to yield the product. (See, e.g., Examples 16, 21, 28, 35 and 40.)

3. Selection of Preferred Compounds

According to one aspect of the present invention, preferred compounds of the present invention are selected for their potency and selectivity toward inhibition of serine proteases, especially urokinase. Such evaluations are routinely performed in vitro, following procedures such as those set forth in Example A. As described therein, and as generally known, a target serine protease and its substrate are combined under assay conditions permitting reaction of the protease with its substrate. The assay is performed in the absence of test compound, and in the presence of increasing concentrations of the test compound. The concentration of test compound at which 50% of the serine protease activity is inhibited by the test compound is the $IC_{50}$ value (Inhibitory Concentration) or $EC_{50}$ (Effective Concentration) value for that compound. Within a series or group of test compounds, those having lower $IC_{50}$ or $EC_{50}$ values are considered more potent inhibitors of the serine protease than those compounds having higher $IC_{50}$ or $EC_{50}$ values. The $IC_{50}$ measurement is often used for more simplistic assays, whereas the $EC_{50}$ is often used for more complicated assays, such as those employing cells. $K_i$ is calculated from the $IC_{50}$.

Preferred compounds according to this aspect of the present invention have a $K_i$ value of 100 nM or less as measured in an in vitro assay for inhibition of urokinase activity. Especially preferred compounds have a $K_i$ value of less than 30 nM.

The test compounds also are evaluated for selectivity toward a serine protease. As described in the Examples, and as generally known, a test compound is assayed for its potency toward a panel of serine proteases and other enzymes and an $IC_{50}$ value or $EC_{50}$ value is determined for each test compound in each assay system. A compound that demonstrates a low $IC_{50}$ value or $EC_{50}$ value or corresponding low $K_i$ value for the target enzyme, e.g., urokinase, and a higher $IC_{50}$ value or $EC_{50}$ value for other enzymes within the test panel (e.g., tissue plasminogen activator, thrombin, Factor Xa), is considered to be selective toward the target enzyme. Generally, a compound is deemed selective if its $IC_{50}$ value or $EC_{50}$ value (or $K_i$ value) in the target enzyme assay is at least one order of magnitude less than the next smallest $IC_{50}$ value or $EC_{50}$ value measured in the selectivity panel of enzymes.

Preferred compounds of the present invention have a $K_i$ value of 100 nM or less as measured in an in vitro assay for inhibition of urokinase activity. Especially preferred compounds have a $K_i$ value in the in vitro urokinase inhibition assay that is at least one order of magnitude smaller than the $IC_{50}$ value measured in the in vitro tPA inhibition assay. Compounds having a selectivity ratio of $IC_{50}$ tPA assay: $K_i$ urokinase assay of greater than 100 are especially preferred.

Compounds of the present invention also are evaluated for their activity in vivo. The type of assay chosen for evaluation of test compounds will depend on the pathological condition to be treated or prevented by use of the compound, as well as the route of administration to be evaluated for the test compound.

For instance, to evaluate the activity of a compound of the present invention to reduce tumor growth through inhibition of urokinase, the procedures described by Jankun et al. [Canc. Res. 57:559–563, 1997] to evaluate PAI-1 can be employed. Briefly, the ATCC cell lines DU145, which expresses a high level of uPA, and LnCaP, which does not express uPA, are injected into SCID mice. After tumors are established, the mice are given test compound according to a dosing regime determined from the compound's in vitro characteristics. The Jankun et al. compound was administered in water. Tumor volume measurements are taken twice a week for about five weeks. A compound is deemed active if an animal to which the compound was administered exhibited decreased tumor volume, as compared to animals receiving appropriate control compounds. Furthermore, a comparison of a compound's effect in animals injected with DU145 cells versus LnCaP cells can indicate whether the compound's effect was due to inhibition of urokinase or otherwise.

Another in vivo experimental model designed to evaluate the effect of p-aminobenzamidine, a purported urokinase inhibitory compound, on reducing tumor volume is described by Billström et al. [Int. J. Cancer 61:542–547, 1995].

To evaluate the ability of a compound of the present invention to reduce the occurrence of, or inhibit, metastasis, the procedures described by Kobayashi et al. [Int. J. Canc. 57:727–733 d, 1994] can be employed. Briefly, a murine xenograft selected for high lung colonization potential is injected into C57B1/6 mice i.v. (experimental metastasis) or s.c. into the abdominal wall (spontaneous metastasis). Various concentrations of the compound to be tested can be admixed with the tumor cells in Matrigel prior to injection. Daily i.p. injections of the test compound are made either on days 1–6 or days 7–13 after tumor inoculation. The animals are killed about three or four weeks after tumor inoculation, and the lung tumor colonies are counted. Evaluation of the resulting data permits a determination as to efficacy of the test compound, optimal dosing and route of administration.

The activity of the compounds of the present invention toward decreasing tumor volume and metastasis can be evaluated in the model described by Rabbani et al. [Int. J. Cancer 63:840–845, 1995] to evaluate their inhibitor. There, Mat LyLu tumor cells over-expressing uPA were injected into the flank of Copenhagen rats. The animals were implanted with osmotic minipumps to continuously administer various doses of test compound for up to three weeks. The tumor mass and volume of experimental and control animals were evaluated during the experiment, as were metastatic growths. Evaluation of the resulting data permits a determination as to efficacy of the test compound, optimal dosing, and route of administration. Some of these authors described a related protocol in Xing et al. [Canc. Res. 57:3585–3593, 1997].

To evaluate the inhibitory activity of a compound of the present invention toward neovascularization, a rabbit cornea neovascularization model can be employed. Avery et al. [Arch. Ophthalmol. 108:1474–1475, 1990] describe anesthetizing New Zealand albino rabbits and then making a central corneal incision and forming a radial corneal pocket. A slow release prostaglandin pellet was placed in the pocket to induce neovascularization. Test compound was administered i.p. for five days, at which time the animals were killed. The effect of the test compound is evaluated by review of periodic photographs taken of the limbus, which can be used to calculate the area of neovascular response and, therefore, limbal neovascularization. A decreased area of neovascularization as compared with appropriate controls indicates the test compound was effective at decreasing or inhibiting neovascularatization.

An angiogenesis model used to evaluate the effect of a test compound in preventing angiogenesis is described by Min et al. [Canc. Res. 56:2428–2433, 1996]. C57BL6 mice receive subcutaneous injections of a Matrigel mixture containing bFGF, as the angiogenesis-inducing agent, with and without test compound. After five days, the animals are killed and the Matrigel plugs, in which neovascularization can be visualized, are photographed. An experimental animal receiving Matrigel and an effective dose of test compound will exhibit less vascularization than a control animal or an experimental animal receiving a less- or non-effective dose of compound.

An in vivo system designed to test compounds for their ability to limit the spread of primary tumors is described by Crowley et al. [Proc. Natl. Acad. Sci. 90:5021–5025, 1993]. Nude mice are injected with tumor cells (PC3) engineered to express CAT (chloramphenicol acetyltransferase). The cells secrete large amounts of uPA and exhibit saturating amounts of uPA activity bound to uPAR on the cell surface. Compounds to be tested for their ability to decrease tumor size and/or metastases are administered to the animals, and subsequent measurements of tumor size and/or metastatic growths are made. In addition, the level of CAT detected in various organs provides an indication of the ability of the test compound to inhibit metastasis; detection of less CAT in tissues of a treated animal versus a control animal indicates less CAT-expressing cells migrated to that tissue.

In vivo experimental models designed to evaluate the urokinase inhibitory potential of a test compound, using a tumor cell line F3II, said to be highly invasive, are described by Alonso et al. [Breast Canc. Res. Treat. 40:209–223, 1996]. This group describes in vivo studies for toxicity determination, tumor growth, invasiveness, spontaneous metastasis, experimental lung metastasis, and an angiogenesis assay.

The CAM model (chick embryo chorioallantoic membrane model), first described by L. Ossowski in 1998 [J. Cell Biol. 107:2437–2445, 1988], provides another method for evaluating the urokinase inhibitory activity of a test compound. In the CAM model, invasion of tumor cells through the chorioallantoic membrane is dependent upon the presence of catalytically active uPA. Contacting CAM with tumor cells in the presence of a urokinase inhibitory agent results in less or no invasion of the tumor cells through the membrane. Thus, the CAM assay is performed with CAM and tumor cells in the presence and absence of various concentrations of test compound. The invasiveness of tumor cells is measured under such conditions to provide an indication of the compound's urokinase inhibitory activity. A compound having urokinase inhibitory activity correlates with less tumor invasion.

The CAM model is also used in a standard assay of angiogenesis (i.e., effect on formation of new blood vessels (Brooks, P. C.; Montgomery, A. M. P.; and Cheresh, D. A., Methods in Molecular Biology 129: 257–269 (1999)). According to this model, a filter disc containing an angiogenesis inducer, such as basic fibroblast growth factor (bFGF) is placed onto the CAM. Diffusion of the cytokine into the CAM induces local angiogenesis, which may be measured in several ways such as by counting the number of blood vessel branch points within the CAM directly below the filter disc. The ability of compounds of the present invention to inhibit cytokine-induced angiogenesis can be tested using this model. A test compound can either be added to the filter disc that contains the angiogenesis inducer, be placed directly on the membrane or be administered systemically. The extent of new blood vessel formation in the presence and/or absence of test compound can be compared using this model. The formation of fewer new blood vessels in the presence of a test compound would be indicative of anti-angiogenesis activity. Since certain of the compounds of the present invention are active as inhibitors of urokinase, anti-angiogenesis activity for such compounds may suggest that urokinase plays a significant role in angiogenesis.

4. Pharmaceutical Compositions

In another aspect, the present invention encompasses pharmaceutical compositions prepared for storage or administration which comprise a therapeutically effective amount of a compound of the present invention in a pharmaceutically acceptable carrier.

The therapeutically effective amount of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy but will depend on such factors as weight, diet, concurrent medication and other factors which those skilled in the medical arts will recognize.

The therapeutically effective amount of the compound of the present invention can range broadly depending upon the desired affects and the therapeutic indication. Typically, dosages will be between about 0.01 mg/kg and 100 mg/kg body weight, preferably between about 0.01 and 10 mg/kg, body weight.

Pharmaceutically acceptable carriers for therapeutic use are well known in the pharmaceutical art, and are described, for example, in *Remington's Pharmaceutical Sciences,* Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

The pharmaceutical compositions of the present invention may be formulated and used as tablets, capsules or elixirs for oral administration; suppositories for rectal administration; sterile solutions and suspensions for injectable administration; and the like. The dose and method of administration can be tailored to achieve optimal efficacy but will depend on such factors as weight, diet, concurrent medication and other factors which those skilled in the medical arts will recognize.

When administration is to be parenteral, such as intravenous on a daily basis, injectable pharmaceutical compositions can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, or the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes) may be utilized.

5. Utility

The compounds of the present invention having urokinase inhibitory activity and/or activity in reducing or inhibiting blood vessel formation, including angiogenesis and neovascularization, may be used both in vitro and in vivo for a number of applications, some of which are described herein below.

The compounds of the present invention are active as inhibitors of urokinase and specifically bind urokinase. Accordingly those compounds that contain sites suitable for linking to a solid/gel support may be used in vitro for affinity chromatography to purify urokinase from a sample or to remove urokinase from a sample using conventional affinity chromatography procedures. These compounds are attached or coupled to an affinity chromatography either directly or through a suitable linker support using conventional methods. See, e.g. Current Protocols in Protein Science, John Wiley & Sons (J. E. Coligan et al., eds, 1997) and Protein Purification Protocols, Humana Press (S. Doonan, ed., 1966) and references therein.

The compounds of the present invention having urokinase inhibitory activity are useful in in vitro assays to measure tPA activity in a sample. In assays which measure the total plasminogen activation activity in a blood sample, a compound of the present invention having urokinase inhibiting activity will knock out that portion of plasminogen activation attributable to uPA, which will allow for calculation of the portion of the total plasminogen activation due to tPA activity as well as that due to uPA activity. Use of such assays to monitor tPA activity would allow better dosage control in patients receiving tPA. These assays could also be used to monitor uPA activity levels in tissue samples, such as from biopsy or to monitor uPA/tPA activities for any clinical situation where measurement of plasminogen activation activity is of assistance. These assays may also be used to monitor plasminogen activator activity where a patient has been treated with a non-endogenous compound having plasminogen activator activity, such as streptokinase and staphlyokinase.

The compounds of the present invention are useful in vivo for treatment of pathologic conditions which would be ameliorated by decreased urokinase activity. For example these compounds will inhibit the activation of metalloproteases by the uPA-plasmin cascade in synovial fluid and thus, may be used in treatment of arthritis.

It is believed these compounds will be useful in decreasing or inhibiting metastasis, neovascularization, and degradation of the extracellular matrix in tumors and other neoplasms. These compounds will be useful as therapeutic agents in treating conditions characterized by pathological neovascularation such as retinal disease, retinopathies and other conditions, including those described hereinabove in the Background and Introduction to the Invention.

Another use for the compounds of the present invention having urokinase inhibitory activity is as an antidote if too much exogenous urokinase has been given to a patient for therewith purposes, such as for dissolving a blood clot.

The compounds of the present invention may be used in treating conditions characterized by inflammation due to their anti-inflammatory effects from inhibition of urokinase, thereby interfering with mediators of cell adhesion or migration. Such anti-inflammatory applications include treatment of stroke and complications of organ transplants.

The present invention includes methods for preventing or treating a condition in a mammal suspected of having a condition which will be attenuated by inhibition of urokinase activity comprising administering to said mammal a therapeutically effective amount of a compound or a pharmaceutical composition of the present invention.

The compounds or pharmaceutical compositions of the present invention are administered in vivo, ordinarily in a mammal, preferably in a human. In employing them in vivo, the compounds or pharmaceutical compositions can be administered to a mammal in a variety of ways, including orally, parenterally, intravenously, subcutaneously, intramuscularly, colonically, rectally, nasally or intraperitoneally, employing a variety of dosage forms. Administration is preferably oral, such as by tablets capsules or elixirs taken on a daily basis.

In practicing the methods of the present invention, the compounds or pharmaceutical compositions of the present invention are administered alone or in combination with one another, or in combination with other therapeutic or in vivo diagnostic agents.

As is apparent to one skilled in the medical art, a "therapeutically effective amount" of the compounds or pharmaceutical compositions of the present invention will vary depending upon the age, weight and mammalian species treated, the particular compounds employed, the particular mode of administration and the desired affects and the therapeutic indication. Because these factors and their relationship to determining this amount are well known in the medical arts, the determination of therapeutically effective dosage levels, the amount necessary to achieve the desired result of inhibiting uPA activity, will be within the ambit of one skilled in these arts. Typically, administration of the compounds or pharmaceutical composition of the present invention is commenced at lower dosage levels, with dosage levels being increased until the desired effect of inhibiting uPA activity to the desired extent is achieved, which would define a therapeutically effective amount. For the compounds of the present invention, alone or as part of a pharmaceutical composition, such doses are between about 0.01 mg/kg and 100 mg/kg body weight, preferably between about 0.01 mg/kg and 10 mg/kg, body weight.

To assist in understanding, the present invention will now be further illustrated by the following examples. These examples as they relate to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

A. Synthesis of Certain Compounds of the Present Invention

Example 1

Preparation of n-butylsulfonyl-D-serine(tert-butylether)-methyl Ester (1)

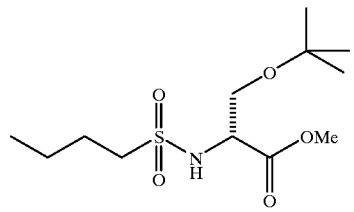

A solution of HCl.H-dSer(tBu)-OMe (2 g, 9.44 mmol) and n-butylsulfonyl chloride (1.1 ml, 8.50 mmol) in tetrahydrofuran (38 ml) was stirred for ten minutes at room temperature. Diisopropylethylamine (5.75 ml, 33.07 mmol) was then added and the cloudy yellow solution was stirred over night at ambient temperature. The reaction mixture was then diluted with ethylacetate (200 ml) and washed with 1N HCl, followed by brine (20 ml each). After drying over anhydrous sodium sulfate, the solvents were removed under vacuum. The flaky yellow solid (1.56 g, 62%) was judged pure by tlc (5% ethylacetate in hexanes).

Example 2

Preparation of n-butylsulfonyl-D-serine(tert-butylether) (2)

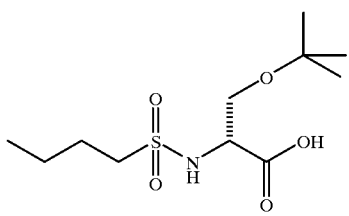

To a solution of compound 1 (1.46 g, 4.94 mmol) in dioxane (32.95 ml), was added dropwise 2.0 N LiOH (5.44 ml, 10.87 mmol). The cloudy yellow solution was allowed to stir at ambient temperature overnight. When no starting material was observed by tlc (5% ethylacetate/hexanes), the excess dioxane was removed in vacuo. The reaction mixture was diluted with a 1:1 mixture of water and methanol and passed through a pre-washed DOWEX (50×8–400) ion exchange resin (30 ml). The resin was rinsed thoroughly with methanol and water. The combined filtrates were concentrated under reduced pressure to afford 1.44 g of the title compound in quantitative yield as a cream solid.

Example 3

Preparation of n-butylsulfonyl-D-serine(tert-butylether)-alanine Tert-butylester (3)

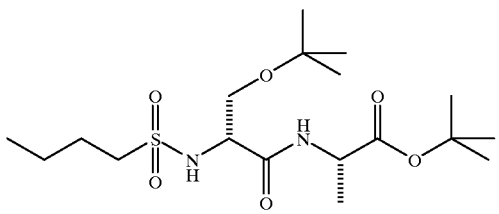

A solution of the compound of Example 2 (0.50 g, 1.79 mmol), alanine tert-butylester hydrochloride salt (0.65 g, 3.58 mmol), EDC (0.68 g, 3.57 mmol), N-hydroxybenzotriazole (0.27 g, 1.79 mmol) and diisopropylethylamine (1.56 ml, 8.94 mmol) was stirred in acetonitrile (18 ml) at ambient temperature. After 18 hours, the solvent was removed under reduced pressure and the resulting residue was resuspended in ethylacetate (50 ml) and 1N HCl (10 ml). The ethylacetate layer was washed with 1N HCl (10 ml), saturated sodium bicarbonate (2×15 ml) and brine (15 ml), then dried with sodium sulfate. The solvent was removed under reduced pressure and the crude product was purified by flash column chromatography eluting with 50%1 ethyl acetate/hexanes, yielding 429 mg (59%) product. The product was a single peak by reverse phase (C18) HPLC ($t_R$=9 minutes at 0.1% trifluoroacetic acid in 5–90% aqueous acetonitrile over 20 minutes).

Example 4

Preparation of n-butylsulfonyl-D-serine-alanine (4)

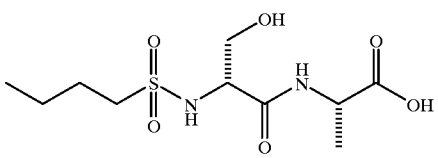

To a solution of the compound of Example 3 (0.42 g, 1.02 mmol) in dichloromethane (4.2 ml) was added trifluoroacetic acid (4.2 ml). The reaction mixture was stirred at ambient temperature for 1 hour. The reaction mixture was diluted with 50 ml n-heptane and concentrated in vacuo. The residue was resuspended in 10 ml acetonitrile and 50 ml n-heptane and concentrated in vacuo to yield 410 mg product.

Example 5

Preparation of α-azido-4-cyanotoluene (5)

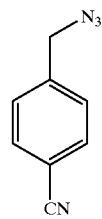

Sodium azide (Aldrich, 3.5 g, 54 mmol) was added to a solution of α-Bromotoluenitrile (Aldrich, 10 g, 51 mmol) in DMF (100 ml), and the resulting mixture was stirred at ambient temperature for 5 hours. The reaction mixture was then diluted with water (350 ml) and extracted with ether (2×100 ml). The combined organic layers were washed with brine and dried (MgSO$_4$). Removal of solvent led to the title compound (8 g, 96%). $^1$H NMR (CDCl$_3$): δ4.42 (s, 2H), 7.41 (d, 2H, J=8.1 Hz), 7.65 (d, 2H, J=8.1 Hz).

Example 6

Preparation of 4-(aminomethyl)benzylnitrile (6)

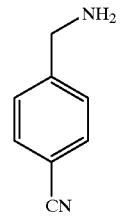

The catalyst of 10% Pd-on-C (Aldrich, 800 mg) was added to a solution of α-azido-4-cyanotoluene (compound 5, 8 g, 51 mmol) in EtOAc (150 ml). The reaction mixture was hydrogenated (H$_2$, 45 psi) in a Parr apparatus for 11 hours. Catalyst was filtered and the solvent was removed under vacuum to give the title compound (6.3 g, 93%). $^1$H NMR (CDCl$_3$): δ3.85 (s, 2H) 7.45 (d, 2H, J=8.1), 7.60 (d, 2H, J=8.1 Hz), 7.78 (s, 2H, NH$_2$).

Example 7

Preparation of n-butylsulfonyl-D-serine-alanine-4-cyanobenzylamide (7)

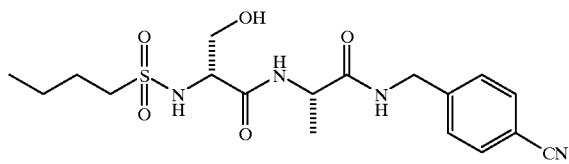

A solution of compound 4 (150 mg, 0.51 mmol), 4-(aminomethyl)benzylnitrile (compound 6, 171 mg, 1.02 mmol), EDC (195 mg, 1.02 mmol), and N-hydroxybenzotriazole (78 mg, 0.51 mmol) in acetonitrile (5.1 ml) was stirred at ambient temperature for 10 minutes. 2,4,6-Collidine (0.34 ml, 2.54 mmol) was then added and the reaction mixture was stirred overnight at ambient temperature. The solvent was removed under reduced pressure and the resulting residue was resuspended in ethylacetate (100 ml) and 0.5M HCl (10 ml). The ethylacetate layer was washed with water followed by 0.5M HCl (10 ml), saturated sodium bicarbonate (2×10 ml) and brine (15 ml), then dried with sodium sulfate. The solvent was removed under reduced pressure to yield 237 mg product. The product eluted at 9.5 minutes by reverse phase (C18) HPLC at 0.11 trifluoroacetic acid in 5–75% aqueous acetonitrile over 20 minutes.

Example 8

Preparation of n-butylsulfonyl-D-serine-alanine-4-hydroxyamidinobenzylamide (8)

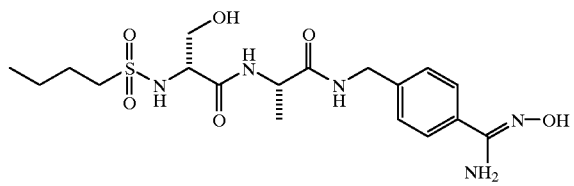

To a solution of the product in Example 7 (117 mg, 0.285 mmol) in 1.14 ml methanol was added hydroxylamine hydrochloride (33.7 mg, 0.485 mmol), followed by N-methylmorpholine (53 µl, 0.485 mmol). The reaction mixture was stirred overnight at ambient temperature and then at 50° C. for six hours. The reaction mixture was concentrated in vacuo. The crude product was taken to the next step (Example 9) without further purification. The product eluted at 6.5 minutes by reverse phase (C18) HPLC at 0.1% trifluoroacetic acid in 5–50% aqueous acetonitrile over 20 minutes.

Example 9

Preparation of n-butylsulfonyl-D-serine-alanine-4-amidinobenzylamide (9)

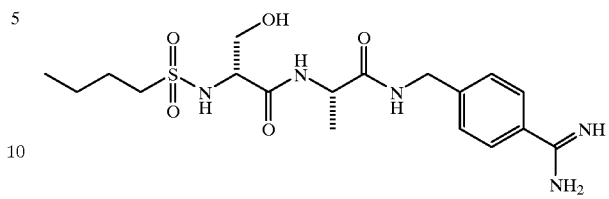

To the product of Example 8 (126 mg, 0.285 mmol) in acetic acid (2.85 ml) and water (0.28 ml) was added 185 mg activated zinc dust. The reaction mixture was stirred overnight at room temperature. The zinc dust was filtered using a glass funnel and the filtrate was purified by preparative HPLC. The fractions containing the product eluted in a 5–20% aqueous acetonitrile containing 0.1% TFA and were pooled and lyophilized yielding 35 mg of the title compound as a white powder. The product eluted at 6.0 minutes by reverse phase (C18) HPLC at 0.1% trifluoroacetic acid in 5–50% aqueous acetonitrile over 20 minutes.

Example 10

Preparation of Benzylsulfonyl-D-serine(tert-butylether)-methyl Ester (10)

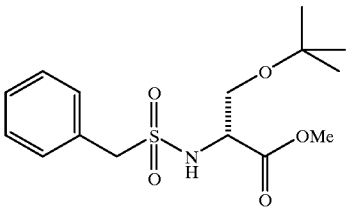

A solution of HCl.H-dSer(tBu)-OMe (1 g, 4.72 mmol) and phenethylsulfonyl chloride (1.45 g, 7.08 mmol) in acetonitrile (19 ml) was stirred for ten minutes at room temperature. Diisopropylethylamine (1.53 ml, 11.81 mmol) was then added and the clear yellow solution was stirred for 18 hours at ambient temperature. The reaction mixture was then diluted with ethylacetate (100 ml) and washed with 1N HCl, followed by brine (10 ml each). After drying over anhydrous sodium sulfate, the solvents were removed in vacuo. The crude product was purified by flash column chromatography eluting with dichloromethane, followed by a gradient consisting of 1 to 5% ethylacetate in dichloromethane, yielding 840 mg (52%) product. Tlc of the final product in 5% ethylacetate in dichloromethane gave one spot with an Rf of 0.52.

Example 11

Preparation of Benzylsulfonyl-D-serine(tert-butylether) (11)

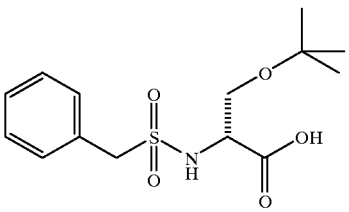

To a solution of the compound of Example 10 (1.0 g, 3.03 mmol) in dioxane (20 ml), was added dropwise 2.0N LiOH (3.33 ml, 6.67 mmol). The solution was allowed to stir at ambient temperature overnight. The excess dioxane was removed in vacuo. The reaction mixture was diluted with a 1:1 mixture of water and methanol and passed through a pre-washed DOWEX (50×8–400) ion exchange resin (30 ml). The resin was rinsed thoroughly with methanol and water. The combined filtrates were concentrated under reduced pressure to afford 1.10 g of the title compound as a yellow glue.

Example 12

Preparation of Tert-butyloxycarbonyl-3,4-dehydroproline p-cyanobenzylamide (12)

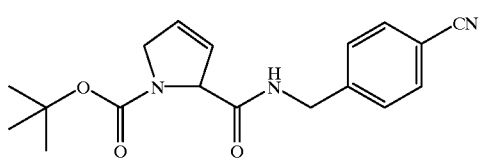

A solution of tert-butyloxycarbonyl-3,4-dehydroproline (0.4 g, 1.88 mmol), 4-(aminomethyl)benzylnitrile (compound 6, 0.47 g, 2.82 mmol), EDC (0.54 g, 2.82 mmol), N-hydroxybenzotriazole (0.29 g, 1.88 mmol), and diisopropylethylamine (1.64 ml, 9.39 mmol) in acetonitrile (7.5 ml) was stirred overnight at ambient temperature. The solvent was removed under reduced pressure and the resulting residue was resuspended in ethylacetate (25 ml) and 0.5M HCl (5 ml). The ethylacetate layer was washed with water followed by 0.5M HCl (5 ml), saturated sodium bicarbonate (2×5 ml) and brine (10 ml), then dried with sodium sulfate. The solvent was removed under reduced pressure and the crude was purified by flash column chromatography eluting with 4/1 ethylacetate/hexane to yield 561 mg pure product (91.3%). The product eluted at 10.5 minutes by reverse phase (C18) HPLC at 0.1% trifluoroacetic acid in 5–75% aqueous acetonitrile over 20 minutes.

Example 13

Preparation of 3,4-dehydroproline-4-cyano Benzylamide Hydrochloride Salt (13)

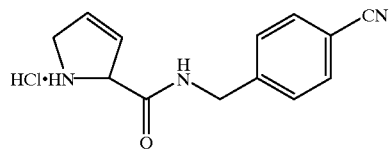

To a solution of the compound of Example 12 (0.47 g, 1.44 mmol) in ethylacetate (5.7 ml) was added 5M anhydrous HCl in ethylacetate (1.44 ml) and the reaction was stirred at ambient temperature overnight. The reaction mixture was concentrated in vacuo to yield 363 mg (95%) of a white solid.

Example 14

Preparation of Benzylsulfonyl-D-serine(tert-butylether)-proline(dehydro)-4-cyanobenzylamide (14)

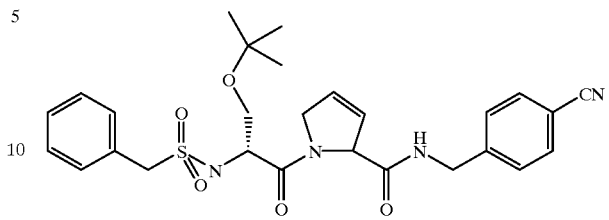

A solution of the compound of Example 11 (0.10 g, 0.32 mmol), the compound of example 13 (0.092 g, 0.34 mmol), EDC (0.091 g, 0.48 mmol), and N-hydroxybenzotriazole (0.053 g, 0.35 1 mmol) was stirred in acetonitrile (1.2 ml) for 10 minutes. 2,4,6-Collidine (0.209 ml, 1.58 mmol) was then added and the reaction mixture was stirred over night at ambient temperature. The solvent was removed under reduced pressure. The resulting residue was resuspended in ethylacetate (50 ml) and 1N HCl (10 ml). The ethylacetate layer was washed with 1N HCl (10 ml), saturated sodium bicarbonate (2×15 ml) and brine (15 ml), then dried with sodium sulfate to a yellow syrup (160 mg, 94%). The product was a single peak by reverse phase (C18) HPLC ($t_R$=11 minutes at 0.1% trifluoroacetic acid in 5–90% aqueous acetonitrile over 20 minutes).

Example 15

Preparation of Benzylsulfonyl-D-serine-3,4-dehydroproline-4-cyanobenzylamide (15)

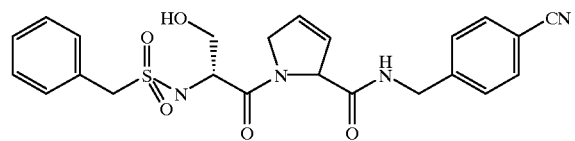

To a solution of the compound of Example 14 (0.16 g, 0.30 mmol) in dichloromethane (0.6 ml) was added trifluoroacetic acid (0.6 ml). The reaction mixture was stirred at ambient temperature for 1 hour. The reaction mixture was diluted with 10 ml n-heptane and concentrated in vacuo. The residue was resuspended in 5 ml acetonitrile and 10 ml n-heptane and concentrated in vacuo to yield 183 mg product.

Example 16

Preparation of Benzylsulfonyl-D-serine-3,4-dehydroproline-4-hydroxyamidinobenzylamide (16)

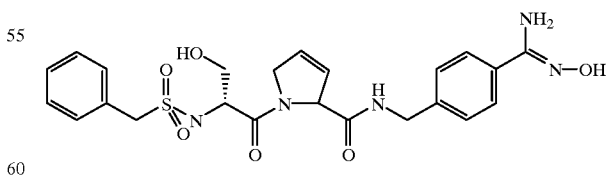

To a solution of the product in Example 15 (143 mg, 0.305 mmol) in 1.22 ml methanol was added hydroxylamine hydrochloride (0.036 mg, 0.519 mmol) followed by N-methylmorpholine (57 μl, 0.519 mmol). The reaction mixture was stirred over night at ambient temperature. Analytical HPLC suggested that the reaction was not complete. Additional hydroxylamine hydrochloride (0.036 mg, 0.519 mmol) and N-methylmorpholine (57 µl, 0.519 mmol) were added and stirring continued at ambient temperature over night. The reaction mixture was concentrated in vacuo and the crude was purified by preparative HPLC. The fractions containing the product eluting in 5–20% aqueous acetonitrile containing 0.1% TFA solution were pooled and lyophilized yielding 16 mg of the title compound as a white powder.

Example 17
Preparation of Benzylsulfonyl-D-serine-3,4-dehydroproline-p-amidinobenzylamide (17)

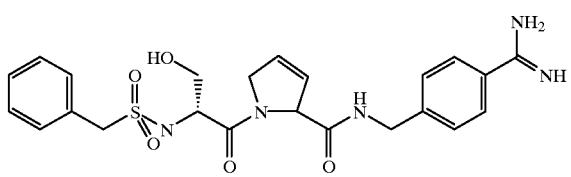

To the product of Example 16 (15 mg, 0.030 mmol) in acetic acid (0.30 ml) and water (0.03 ml) was added 19 mg activated zinc dust. The reaction mixture was stirred over night at room temperature. The zinc dust was filtered using a glass funnel and the filtrate was purified by preparative HPLC. The fractions containing the product eluted in a 5–20% aqueous acetonitrile containing 0.1% TFA, and were pooled and lyophilized yielding 7 mg of the title compound as a white powder. The product eluted at minutes by reverse phase (C18) HPLC at 0.1% trifluoroacetic acid in 5–50% aqueous acetonitrile over 20 minutes.

Example 18
Preparation of Bis(benzyloxycarbonyl)guanidine (18)

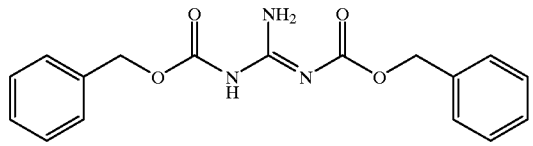

The synthesis of the title product was carried out as cited in the literature (tetrahedron Letters, vol. 35, No. 7, pp. 977–980, 1994) and is described below:

A solution of N,N'-bis(benzyloxycarbonyl)—S-methylisothiourea (1 g, 2.79 mmol) in 7N anhydrous ammonia in methanol (5.5 ml) was stirred overnight at ambient temperature. The reaction mixture was concentrated and the remaining residue was diluted with ethylacetate (10 ml). The organic layer was washed twice with saturated sodium bicarbonate and once with brine (10 ml each). After drying over sodium sulfate, the crude product was subjected to flash column chromatography eluting with 3/2 ethylacetate/hexanes to yield 0.87 g of a white solid. The product was then recrystallized in 1:1 ethylacetate: hexane solvent system to yield 337 mg (37%) pure product (mp=151° C.).

Example 19

Preparation of Tert-butyloxycarbonyl-4-amino-1-butanol (19)

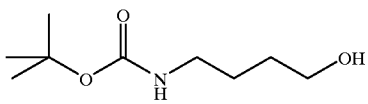

To a solution of 4-amino-1-butanol (1 g, 11.22 mmol) in tetrahydrofuran (45 ml) was added Boc-anhydride (2.20 g, 10.10 mmol) and triethylamine (2.84 g, 28.04 mmol). The reaction mixture was stirred overnight at room temperature. The reaction mixture was concentrated and the remaining residue was diluted with ethylacetate (250 ml) and 1M HCl (50 ml). The layers were separated and the organic layer was washed with 1N HCl, water and brine (50 ml each). After drying over sodium sulfate 1.9 g (99%) product was obtained as a clear oil.

Example 20

Synthesis of g-N,N'-bis(benzyloxycarbonyl)agmatine Trifluoroacetate Salt (20)

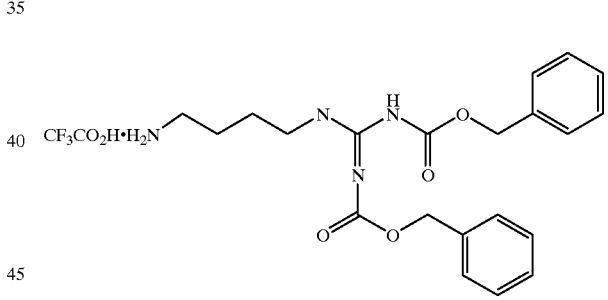

To a solution of compound 18 (the product of Example 18) (0.2 g, 0.61 mmol) and triphenylphosphine (0.12 g, 0.46 mmol) in dry toluene (6.6 ml) under nitrogen was added via syringe compound 19 (the product of Example 19). The mixture was cooled to 0° C., and diethylazodicarboxylate (0.080 g, 0.46 mmol) was added dropwise over 15 minutes. The reaction mixture was stirred at room temperature over night at which time tlc in 3/2 ethylacetate/hexane confirmed the completion of the reaction. Five drops of water were added and the solvent was evaporated in vacuo. The crude was purified by flash column chromatography eluting with 9/1 hexanes/ethylacetate, followed by 3/2 hexanes/ethylacetate to yield 83 mg (74%) pure product. The product was then treated with dichloromethane and trifluoroacetic acid (1 ml each) for one hour at ambient temperature. Removal of the solvents in vacuo afforded 80 mg product 20.

Example 21
Preparation of n-butylsulfonyl-D-serine-alanine-agmatine-g-N,N-bis(benzyloxycarbonyl) (21)

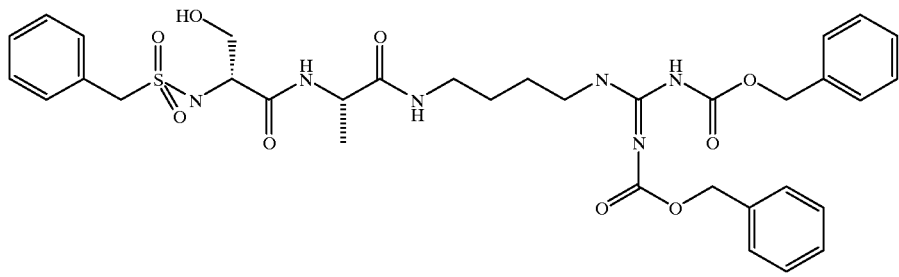

A solution of the compound of Example 4 (0.05 g, 0.17 mmol), and the compound of Example 20 (0.065 g, 0.17 mmol), EDC (0.065 g, 0.34 mmol), and hydroxybenzotriazole (0.026 g, 0.17 mmol) was stirred in acetonitrile (0.67 ml) for 10 minutes. 2,4,6-Collidine (0.11 ml, 0.84 mmol) was then added and the reaction mixture was stirred overnight at ambient temperature. The solvent was removed under reduced pressure and the resulting residue was resuspended in ethylacetate and 1N HCl (5 ml each). The ethylacetate layer was washed with 1N HCl (5 ml), saturated sodium bicarbonate (2×5 ml) and brine (5 ml), then dried with sodium sulfate to a solid (114 mg, 94%).

Example 22
Preparation of n-butylsulfonyl-D-serine-alanine-agmatine (22)

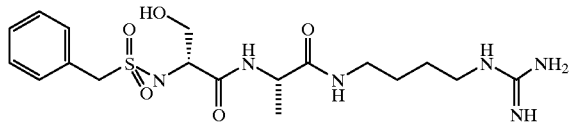

The compound of Example 21 (114 mg, 0.17 mmol) was dissolved in methanol (15 ml) and was hydrogenated on a Parr shaker overnight at 40 psi in the presence of 15 mg palladium on charcoal. The catalyst was filtered off. The reaction mixture was diluted to 35 ml with water and purified by preparative HPLC. The fractions containing the product eluted in 0–25% aqueous acetonitrile containing 0.1% TFA and were pooled and lyophilized yielding 16 mg of the title compound as a white powder.

Example 23
Preparation of 2-cyano-5-methylthiophene (23)

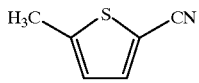

A solution of 2-bromo-5-methylthiophene (TCI chemicals, 5 g, 28 mmol) and copper(I) cyanide (Aldrich, 2.53 g, 28 mmol) in DMF (10 ml) was heated at its reflux temperature for 4 hours. After cooling to ambient temperature, ethyl acetate (500 ml) and 10% NaCN aqueous solution (500 ml) was added. After separation, the aqueous layer was extracted with ethyl acetate (300 ml), and the combined organic layers were concentrated to an oil. The oil was further purified by a flash column chromatography (ethyl acetate) to give the title compound (3.03 g, 87%). TLC: Rf 0.30 (1:1 of hexane/ethyl acetate); $^1$H NMR (CDCl$_3$): δ 2.55 (m, 3H), 6.76 (d, 1H, J=3.6 Hz), 7.42 (d, 1H, J=3.6 Hz).

Example 24
Preparation of 2-cyano-5-(bromomethyl)thiophene (24)

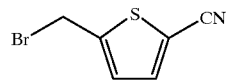

A solution of 2-cyano-5-methylthiophene (compound 23, 3.0 g, 24 mmol), N-bromosuccinimide (Aldrich, 4.8 g, 27 mmol), and 2,2'-azobisisobutyronitrile (Aldrich, 0.4 g, 2.4 mmol) in CCl$_4$ (Aldrich, 60 ml) was heated at its reflux temperature for 5 hours. After cooling to ambient temperature, the solvent was removed under vacuum to give a yellow oil. The oil was purified by a flash column chromatography (1:1 of hexane/ethyl acetate) to give the title compound (4.5 g, 91%). TLC: Rf 0.91 (1:1 of hexane/ethyl acetate); $^1$H NMR (CDCl$_3$): δ 4.66 (s, 2H), 7.10 (d, 1H, J=3.8 Hz), 7.48 (d, 1H, J=3.8 Hz).

Example 25
Preparation of 2-cyano-5-(azidomethyl)thiophene (25)

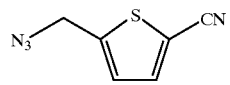

A solution of 2-cyano-5-(bromomethyl)thiophene (compound 24, 3.5 g, 17.3 mmol) and sodium azide (Aldrich, 1.7 g, 26 mmol) in DMF (Aldrich, 60 ml) was stirred at ambient temperature for 10 hours. Flash column chromatography (20% ethyl acetate in hexane) resulted the title compound (2.35 g, 83%). TLC: Rf 0.48 (20% of ethyl acetate in hexane); $^1$H NMR (CDCl$_3$): δ 4.56 (s, 2H), 7.01 (d, 1H, J=3.7 Hz), 7.55 (d, 1H, J=3.7 Hz).

Example 26
Preparation of 2-cyano-5-(aminomethyl)thiophene (26)

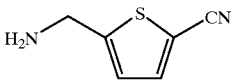

Triphenylphosphine (Aldrich, 5.7 g) was added to a solution of 2-cyano-5-(azidomethyl)thiophene (compound 25, 2.5 g, 10 mmol) in THF (Aldrich, 40 ml) and water (10 ml) at 0° C. The resulting solution was allowed to warm to room temperature and stirred at ambient temperature for 10 hours. RP HPLC purification led to the title compound (2.3 g, 94%). MS (electrospray): 139 (M+1); $^1$HNMR (CDCl$_3$): δ 4.01 (s, 2H), 4.75 (br s, 2H, NH$_2$), 6.82 (d, 1H, J=3.5 Hz), 7.08 (d, 1H, J=3.5 Hz).

Example 27
Preparation of n-butylsulfonyl-D-serine-alanine-2-cyano-5-(methylamide)thiophene (27)

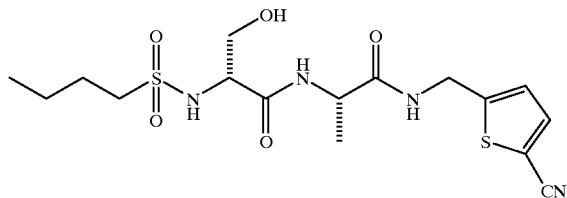

A solution of the compound of example 4 (4, 860 mg, 2.9 mmol), and the compound of Example 26 (26, 400 mg, 2.9 mmol), EDC (556 mg, 2.9 mmol), N-hydroxybenzotriazole (488 mg, 3.19 mmol) and diisopropylethylamine (1.5 ml, 8.7 mmol) was stirred overnight at ambient temperature. The solvent was removed under reduced pressure and the resulting residue was resuspended in ethylacetate (50 ml) and 1N sodium bisulfate (10 ml). The ethylacetate layer was washed with 1N sodium bisulfate (10 ml), saturated sodium bicarbonate (2×15 ml) and brine (15 ml), then dried with sodium sulfate to give a yellow oil. The crude product was subjected to flash column chromatography eluting with a 4/5/1 ratio of ethylacetate/hexanes/methanol. The product was a 3:1 mixture of diastereomers by reverse phase (C18) HPLC (t$_R$=8.5 minutes at 0.1% trifluoroacetic acid in 5–75% aqueous acetonitrile over 30 minutes). Low resolution mass spectroscopy confirmed the desired mass (MH$^+$ 417).

Example 28
Synthesis of n-butylsulfonyl-D-serine-alanine-2-hydroxyamidino-5-(methylamide)thiophene (28)

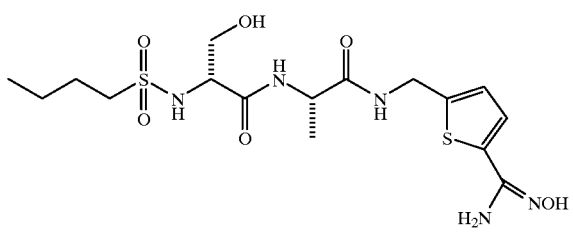

To a solution of the product in Example 27 (220 mg, 0.53 mmol) in 5 ml methanol was added hydroxylamine hydrochloride (184 mg, 2.64 mmol) followed by N-methylmorpholine (290 μl, 2.64 mmol). The reaction mixture was stirred overnight at ambient temperature. The methanol mixture was concentrated in vacuo and the remaining residue was diluted with ethylacetate and washed with saturated sodium bicarbonate and brine (10 ml each). The organic layers were dried over anhydrous sodium sulfate and concentrated in vacuo to give a yellow oil (120 mg, 50%). The product was a 3:1 mixture of diastereomers by reverse phase (C18) HPLC (t$_R$=5 minutes at 0.1% trifluoroacetic acid in 5–75% aqueous acetonitrile over 20 minutes). Low resolution mass spectrum confirmed the desired mass (MH$^+$ 450.5).

Example 29

Synthesis of n-butylsulfonyl-D-serine-alanine-2-amidino-5-(methylamide)thiophene (29)

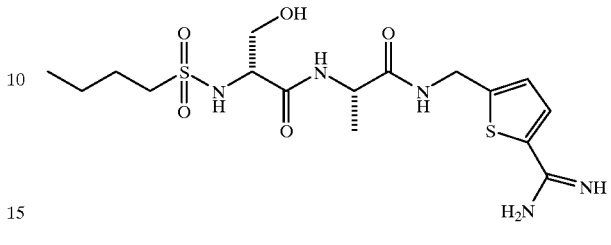

To the product of Example 28 (60 mg, 0.13 mmol) in acetic acid (1.3 ml) and water (0.13 ml) was added 87 mg activated zinc dust. The reaction mixture was stirred overnight at ambient temperature. The zinc dust was filtered using a glass funnel and the filtrate was purified by preparative HPLC. The fractions containing the product eluted in 0–20% aqueous acetonitrile containing 0.1% TFA. They were pooled and lyophilized yielding 7 mg of the title compound as a white powder. The 3:2 diastereomeric mixture of products eluted at 13 minutes by reverse phase (C18) HPLC at 0.1 trifluoroacetic acid in 5–50% aqueous acetonitrile over 20 minutes. Low resolution mass spectroscopy confirmed the desired mass (MH$^+$ 434).

Example 30

Synthesis of Tert-butyloxycarbonyl-3,4-methanoproline (30) (Steps A to E Below)

Step A. Synthesis of N-benzyl-3,4-methanoprolinol (b)

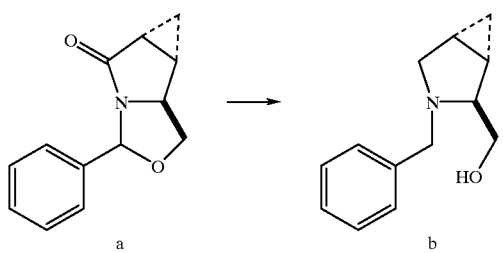

A mixture of the benzylidene starting material (a) (J. Org. Chem. 1999, 64(2), 547) (4.6 grams, 21.4 mmol) and lithium aluminum hydride (1.0M in THF, 64 ml, 64 mmol) was heated at reflux for 5 hours. After cooling to 0° C., the remaining aluminum hydride was carefully quenched by the dropwise addition of saturated aqueous sodium sulfate (5 ml) over 15 minutes. The mixture was diluted with ethylacetate (200 ml) and then filtered through celite. The filtrate was dried with sodium sulfate, filtered and concentrated to give crude N-benzyl aminoalcohol (3.45 grams), which was carried on to the next step without further purification.

Step B. Synthesis of N-benzyloxycarbonyl-3,4-methanoprolinol

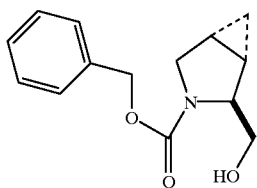

A solution of crude N-benzyl-3,4-methanoprolinol (step A, (b))(3 grams, 14.76 mmol) in methanol (120 ml) and concentrated HCl (1.5 ml) with 10% Pd/C (300 mg) was hydrogenated at 50 psi for 16 hours. The reaction mixture was filtered to remove the carbon-based catalyst and the filtrate was concentrated. The residue was dissolved in water/dioxane (100 ml) and diisopropylethylamine (3.2 ml) was added. Benzyl chloroformate (2.76 ml, 16.2 mmol) was added and the reaction mixture was stirred overnight. The reaction mixture was concentrated, dissolved in 1M HCl (100 ml) and extracted with ethylacetate (3×200 ml). The combined organic layers were dried with magnesium sulfate, filtered and concentrated. The residue was purified by flash chromatography using 1:3 ethylacetate/hexanes to give the N-Cbz-3,4-methanoprolinol (2.4 g).

Step C. Synthesis of N-benzyloxycarbonyl-3,4-methanoproline

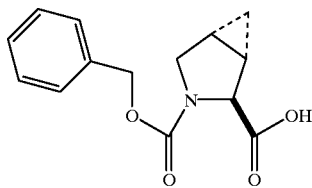

To a solution of N-benzyloxycarbonyl-3,4-methanoprolinol (2.2 g, 8.90 mmol) in acetone (68 ml), stirring at 0° C., was added Jones reagent (6.6 ml) dropwise over 5 minutes. [Jones Reagent: Prepared from chromium trioxide (13.4 g) and concentrated sulfuric acid (11.5 ml) diluted with water to a total volume of 50 ml.] After stirring at 0° C. for 3 hours, isopropanol (11 ml) was added and stirring was continued for an additional 10 minutes. The reaction mixture was diluted with water (400 ml) and extracted with ethylacetate (3×500 ml). The combined organic layers were dried over magnesium sulfate, filtered and concentrated to give N—Cbz-3,4-methanoproline (2.25 g, 96%).

Step D. Synthesis of 3,4-methanoproline hydrochloride salt

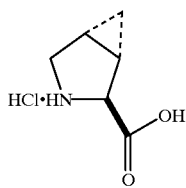

To a solution of N-benzyloxycarbonyl-3,4-methanoproline (obtained in step C, above) (1.23 g, 4.71 mmol) in ethanol (47 ml) and 0.5M HCl (9.42 ml) was added 10% palladium on carbon catalyst. The reaction mixture was hydrogenated at atmospheric pressure overnight. The catalyst was filtered off and the filtrate was concentrated in vacuo to yield 767 mg pure product. The product eluted at 14 minutes by reverse phase (C18) HPLC at 0.1% trifluoroacetic acid in 5–75% aqueous acetonitrile over 20 minutes.

Step E. Preparation of tert-butyloxycarbonyl-3,4-methanoproline

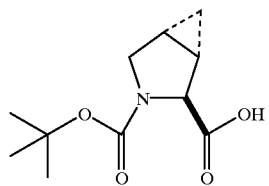

To a solution of 3,4-methanoproline hydrochloride salt (from step D above) (1.04 g, 6.38 mmol) in dioxane and water (25 ml each) was added potassium carbonate (1.76 g, 12.76 mmol) and Boc-anhydride (2.78 g, 12.76 mmol). The reaction mixture was stirred overnight at ambient temperature. The dioxane was removed in vacuo and the remaining residue was diluted with diethylether. The layers were separated and the aqueous layer was extracted with diethyl ether (1×25 ml). The aqueous layer was acidified to pH<3 with 1N hydrochloric acid and extracted with ethylacetate (3×25 ml). The organic layer was dried over sodium sulfate, decanted and concentrated under reduced pressure to afford 745 mg (50%) product. The product eluted at 12.5 minutes by reverse phase (C18) HPLC at 0.1% trifluoroacetic acid in 5–75% aqueous acetonitrile over 20 minutes.

Example 31

Preparation of Tert-butyloxycarbonyl-3,4-methanoproline-4-cyanobenzylamide (31)

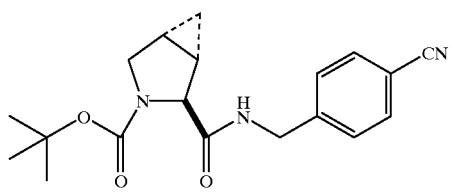

A solution of the compound of Example 30 (step E) (0.70 g, 3.082 mmol), p-cyanobenzylamine hydrochloride salt (0.784 g, 4.62 mmol), EDC (0.88 g, 4.62 mmol), N-hydroxybenzotriazole (0.47 g, 3.082 mmol) and diisopropylethylamine (2.68 ml, 15.41 mmol) was stirred in acetonitrile (12 ml) at ambient temperature. After 18 hours, the solvent was removed under reduced pressure and the resulting residue was resuspended in ethylacetate (150 ml) and washed consecutively with 0.5 M HCl (2×15 ml), brine (1×15 ml), saturated sodium bicarbonate (2×15 ml), and brine (1×15 ml). The organic layer was dried over sodium sulfate, decanted and concentrated in vacuo. The crude product was purified by flash column chromatography eluting with 4/1 ethyl acetate/hexanes, yielding 822 mg (70%) product.

Example 32
Preparation of 3,4-methanoproline-4-cyanobenzylamide Hydrochloride Salt (32)

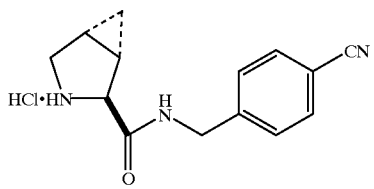

To a solution of the compound of Example 31 (1 g, 2.93 mmol) in ethylacetate (11.7 ml) was added 5M anhydrous HCl in ethylacetate (2.93 ml) and the reaction was stirred at ambient temperature overnight. The reaction mixture was concentrated in vacuo to yield 645 mg (79%) of a white solid.

Example 33
Preparation of benzylsulfonyl-D-serine(tert-butylether)-3,4-methanoproline-4-cyanobenzylamide (33)

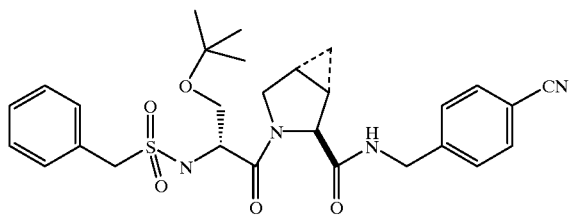

A solution of the compound of Example 11 (0.10 g, 0.32 mmol), the compound of Example 32 (0.105 g, 0.38 mmol), EDC (0.073 g, 0.38 mmol), N-hydroxybenzotriazole (0.049 g, 0.32 mmol), and diisopropylethylamine (0.28 ml, 1.59 mmol) was stirred overnight at ambient temperature. The solvent was removed under reduced pressure and the resulting residue was resuspended in ethylacetate (50 ml) and 1N HCl (10 ml). The ethylacetate layer was washed with 1N HCl (10 ml), saturated sodium bicarbonate (2×15 ml) and brine (15 ml), then dried with sodium sulfate. The organic layer was decanted and concentrated under reduced pressure to yield 171 mg product.

Example 34
Preparation of Benzylsulfonyl-D-serine-3,4-methanoproline-4-cyanobenzylamide (34)

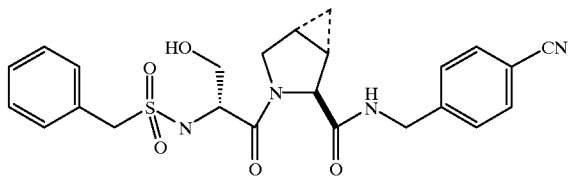

To a solution of the compound of Example 33 (0.17 g, 0.32 mmol) in dichloromethane (4 ml) was added trifluoroacetic acid (4 ml). The reaction mixture was stirred at ambient temperature for 1 hour. The reaction mixture was diluted with 10 ml n-heptane and concentrated in vacuo. The residue was resuspended in 5 ml acetonitrile and 10 ml n-heptane and concentrated in vacuo to yield 154 mg product.

Example 35
Preparation of Benzylsulfonyl-D-serine-3,4-methanoproline-4-hydroxyamidinobenzylamide (35)

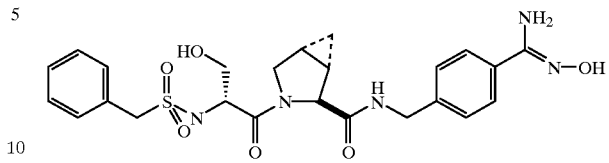

To a solution of the product in Example 34 (154 mg, 0.32 mmol) in 1.3 ml methanol was added hydroxylamine hydrochloride (0.11 g, 1.58 mmol) followed by N-methylmorpholine (209 μl, 1.902 mmol). The reaction mixture was stirred overnight at ambient temperature. The reaction mixture was concentrated in vacuo. The crude product was resuspended in 25% acetonitrile in water and purified by preparative HPLC. The fractions containing the product eluting in 0–20% aqueous acetonitrile containing 0.1% TFA solution were pooled and lyophilized yielding 19.5 mg of the title compound as a white powder. Low resolution mass spectroscopy confirmed the desired mass ($MH^+$ 516).

Example 36
Preparation of Benzylsulfonyl-D-serine-3,4-methanoproline-p-amidinobenzylamide (36)

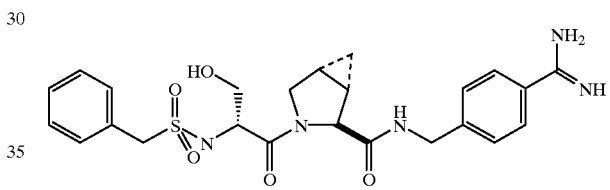

To the product of Example 35 (19.5 mg, 0.041 mmol) in acetic acid (0.41 ml) and water (0.041 ml) was added 27 mg activated zinc dust. The reaction mixture was stirred over night at room temperature. The zinc dust was filtered using a glass funnel and the filtrate was purified by preparative HPLC. The fractions containing the product eluting in 0–20% aqueous acetonitrile containing 0.1% TFA were pooled and lyophilized yielding 15 mg of the title compound as a white powder. The product eluted at 10.5 minutes by reverse phase (C18) HPLC at 0.1% trifluoroacetic acid in 5–50% aqueous acetonitrile over 20 minutes. Low resolution mass spectroscopy confirmed the desired mass ($MH^+$ 500).

Example 37
Preparation of 4-trifluoracetamidometylaniline (7-2)

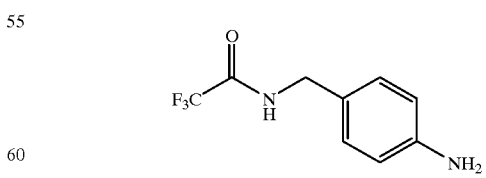

4-Nitrobenzylamine (7-1) (4.0 g, 21 mmol) was added in portions to trifluoroacetic anhydride (15 ml) while the mixture was being cooled on ice. The mixture was allowed to warm to room temperature and stirred overnight. The suspension was poured onto ice (approximately 200 g), and the cloudy suspension was extracted with CH₂Cl₂ (2×100 ml), dried over Na₂SO₄ and the solvent removed to give a transparent oil. This oil was shaken in a Parr flask with Pd/C (10%, 300 mg) in MeOH (50 ml) overnight. The solid was removed by filtration and the solvent removed in vacuo to give a white solid corresponding to the title compound (7-2) (4.5 g, quantitative yield).

Example 38

Preparation of N-[(4-Trifluoracetamidometyl)phenyl]-N'-N''-bis(tert-butoxycarbonyl) Guanidine (7-3)

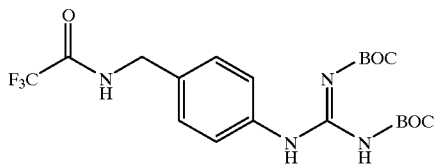

4-Trifluoracetamidometylaniline (7-2) (279 mg, 1.28 mmol) was added to a stirring mixture of N-N'-Di-Boc-N''-trifluoromethanesulfonyl-guanidine (prepared according to the procedure described in *J. Org. chem.* 1998, 63, 3804–3805)(500 mg, 1.28 mmol), TEA (108 μl, 1.28 mmol) in CH₂Cl₂ (10 ml). The reaction mixture was stirred for 6 hours. The mixture was diluted with CH₂Cl₂ (30 ml) and washed with HCl (1M, 20 ml), brine (20 ml), dried over Na₂SO₄ and the solvent removed in vacuo to give a solid. Column chromatography (CH₂Cl₂/MeOH, 99:1) gave a white solid corresponding to the title compound (350 mg, 52%).

Example 39

Preparation of N-[(4-aminometyl)phenyl]-N'-tert-butoxycarbonylguanidine (7-4)

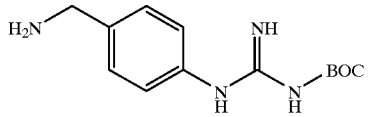

Potassium carbonate (500 mg) was added to a stirring solution of N-[(4-trifluoracetamidometyl)phenyl]-N'-N''-bis(tert-butoxycarbonyl) guanidine (7-3) (300 mg, 0.833 mmol) in H₂O/MeOH (2:15, 17 ml) and the mixture was stirred overnight. The solvent was removed in vacuo, and the remaining residue was dissolved in H₂O (10 ml) and extracted with CH₂Cl₂/MeOH (9:1, 3×10 ml). The organic layers were dried over Na₂SO₄ and removed in vacuo to give a white solid corresponding to the title compound (150 mg, 68%).

Example 40

Preparation of Benzylsulfonyl-D-serine-L-alanine-(4-(N-tert-butoxycarbonylguanidino)benzylamide (7-5)

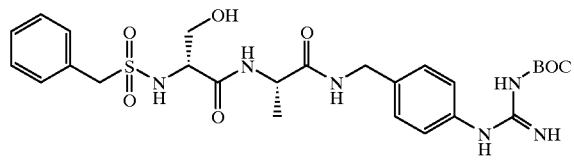

A solution of N-[(4-aminometyl)phenyl]-N'-tert-butoxycarbonylguanidine (7-4) (36 mg, 0.14 mmol), benzylsulfonyl-D-serine-L-alanine carboxylate (50 mg, 0.13 mmol), HATU (74 mg, 0.20 mmol), HOAT (27 mg, 0.20 mmol), and DIEA (68 μl, 0.39 mmol) in acetonitrile (2.0 ml) was stirred at room temperature overnight. The solution was diluted with EtOAc (20 ml) washed with HCl (1M, 10 ml), NaHCO₃ (saturated, 10 ml), brine (10 ml), and removed in vacuo to give an oil. HPLC purification (CH₃CN, H₂O, 0.1% TFA) gave a fluffy white solid as the title compound (35 mg, 45%), MS (electrospray) 577 (M+1).

Example 41

Preparation of Benzylsulfonyl-D-serine-L-alanine-4-guanidinobenzylamide (7-6)

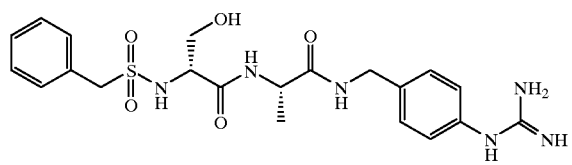

A solution benzylsulfonyl-D-serine-L-alanine-(4-(N-tert-butoxycarbonylguanidino) benzylamide (7-5) (9.0 mg, 0.016 mmol), in a mixture of CH₂Cl₂/TFA (1:1, 600 μl) was stirred at room temperature for 90 minutes. The solvent was removed in vacuo to give a transparent oil. HPLC purification (CH₃CN, H₂O, 0.1% TFA) gave a fluffy white solid as the title compound (5.0 mg, 66%), MS (electrospray) 477 (M+1).

Example 42

Preparation of 3-Trifluoracetamidometylaniline (8-2)

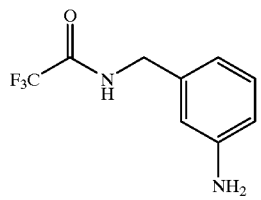

3-Nitrobenzylamine (8-1) (3.0 g, 16 mmol) was added in portions to stirring trifluoroacetic anhydride (30 ml) while the mixture was being cooled on ice, and the mixture stirred overnight. The suspension was poured onto ice (approximately 200 g) and the cloudy suspension was extracted with CH₂Cl₂ (2×100 ml) dried over Na₂SO₄ and the solvent removed to give a transparent oil. This oil was shaken in a Parr flask with Pd/C (10%, 300 mg) in MeOH (30 ml) overnight. The solid was removed by filtration and the solvent removed in vacuo to give a white solid corresponding to the title compound (3.3 g, 95%).

Example 43
Preparation of N-[(3-Trifluoracetamidometyl)phenyl]-N'-N''-bis(tert-butoxycarbonyl) Guanidine (8-3)

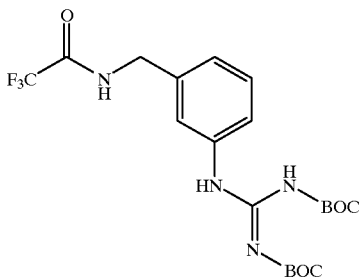

3-Trifluoracetamidometylaniline (8-2) (the product of Example 42) (500 mg, 2.29 mmol) was added to a stirring mixture of N-N'-Di-Boc-N''-trifluoromethanesulfonyl-guanidine (prepared according to the procedure described in *J. Org. chem.* 1998, 63, 3804–3805) (986 mg, 2.52 mmol), TEA (642 μl, 4.58 mmol) in $CH_2Cl_2$ (10 ml), and the mixture was stirred for 24 hours. The mixture was washed with HCl (1M, 10 ml), brine (10 ml) dried over $Na_2SO_4$ and the solvent removed in vacuo to give a solid. Column chromatography ($CH_2Cl_2$/MeOH, 98:2) gave a white solid corresponding to the title compound (479 mg, 55%). MS (electrospray) 461 (M+1).

Example 44
Preparation of N-[(3-aminometyl)phenyl]-N'-tert-butoxycarbonylguanidine (8-4)

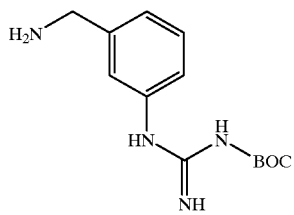

Potassium carbonate (1.0 g) was added to a stirring solution of N-[(3-trifluoracetamidometyl)phenyl]-N'-N''-bis(tert-butoxycarbonyl) guanidine (8-3) (the product of Example 43) (450 mg, 0.978 mmol) in $H_2O$/MeOH (1:1, 4 ml) and the mixture was stirred overnight. The solvent was removed in vacuo, and the remaining residue was dissolved in $H_2O$ (10 ml) and extracted with $CH_2Cl_2$/MeOH (9:1, 3×10 ml). The organic layers were dried over $Na_2SO_4$ and removed in vacuo to give a white solid corresponding to the title compound (232 mg, 90%).

Example 45
Preparation of Benzylsulfonyl-D-serine-L-alanine-3-guanidinobenzylamide (8-5)

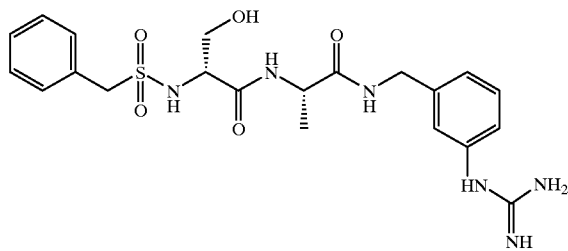

A solution of N-[(3-aminometyl)phenyl]-N'-tert-butoxycarbonylguanidine (8-4) (the product of Example 44) (130 mg, 0.492 mmol), benzylsulfonyl-D-serine-L-alanine carboxylate (190 mg, 0.492 mmol), HATU (380 mg, 0.739 mmol), HOAT (136 mg, 0.739 mmol), and DIEA (258 μL, 1.48 mmol) in acetonitrile (2.0 ml) was stirred at room temperature overnight. The solution was diluted with EtOAc (20 ml), washed with HCl (1M, 10 ml), $NaHCO_3$ (saturated, 10 ml), brine (10 ml), and removed in vacuo to give an oil. The oil was treated with a mixture of $CH_2Cl_2$/TFA (1:1, 3 ml) was stirred at room temperature for 2 hours. The solvent was removed in vacuo to give a transparent oil. HPLC purification ($CH_3CN$, $H_2O$, 0.1% TFA) gave a fluffy white solid as the title compound (80 mg, 34%), MS (electrospray) 477 (M+1).

Example 46

Preparation of 2-Nitro-5-(4-trifluoracetamidometyl)-thiophene (9-2)

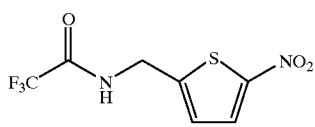

2-Aminomethylthiophene (9-1) (5.0 g, 44 mmol) was added in portions to stirring trifluoroacetic anhydride (20 ml) while the mixture was being cooled on ice, and the mixture stirred for one hour. To this solution was added $KNO_3$ (8.9 g, 88 mmol) in portions at −20° C. The homogeneous solution was warmed up to ambient temperature and stirred overnight. The resulting suspension was poured onto ice (approximately 200 g), and extracted with $CH_2Cl_2$ (2×100 ml), dried over $Na_2SO_4$, and the solvent removed to give a solid. Column chromatography ($CH_2Cl_2$) gave a white solid corresponding to the title compound (3.3 g, 29%), MS (electrospray): 255 (M+1).

Example 47

Preparation of N-[2-(5-Trifluoracetamidometyl)thiophenyl]-N'-N''-(bis-tert-butoxycarbonyl) Guanidine (9-3)

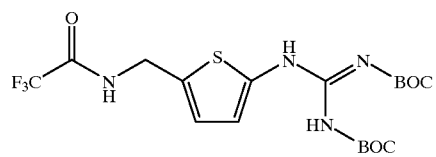

2-Nitro-5-(4-trifluoracetamidometyl)-thiophene (9-2) (1.0 g, 3.9 mmol) was added to a saturated solution of HCl in MeOH at 0° C. $SnCl_2$ (4.4 g) was added in portions over 15 minutes and the mixture was stirred for 30 minutes. The solution was concentrated and then diluted with NaHCO₃ (10 ml) This solution was extracted with CH₂Cl₂ (2×20 ml), dried over Na₂SO₄ and the solvent removed in vacuo to give 2-amino-5-(4-trifluoracetamidometyl)-thiophene as a yellow oil (>95% purity by NMR, 0.80 g, 95%). This compound was used immediately in the next step without further purification.

2-Amino-5-(4-trifluoracetamidometyl)-thiophene (0.80 g, 3.6 mmol) was added to a stirring solution of N-N'-Di-Boc-N"-trifluoromethanesulfonyl-guanidine (1.5 g, 3.8 mmol) and TEA (1.1 ml, 7.8 mmol) in CH₂Cl₂ (20 ml). The mixture was stirred for 24 hours. The mixture was diluted with CH₂Cl₂ (20 ml) and washed with HCl (1M, 20 ml), brine (20 ml), dried over Na₂SO₄. The solvent was removed in vacuo to give an oil. Column chromatography (CH₂Cl₂/MeOH, 98:2) gave an oil corresponding to the title compound (9-3) (150 mg, 9%), MS (electrospray): 467 (M+1).

Example 48
Preparation of N-[5-(4-aminometyl)thiophen1]-N'-(tert-butoxycarbonyl) Guanidine (9-4)

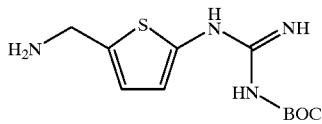

Potassium carbonate (500 mg) was added to a stirring solution of N-[2-(5-trifluoracetamidometyl)thiophenyl]-N'-N"-(bis-tert-butoxycarbonyl) guanidine (9-3) (150 mg, 0.322 mmol) in H₂O/MeOH (1:1, 4 ml) and the mixture was stirred overnight. The solvent was removed in vacuo. The remaining residue was dissolved in H₂O (10 ml) and extracted with CH₂Cl₂/MeOH (95:5, 3×10 ml). The organic layers were dried over Na₂SO₄. Solvent was removed in vacuo to give a yellow solid corresponding to the title compound (150 mg, 68%).

Example 49
Preparation of Benzylsulfonyl-D-Serine-L-Alanine-[5-(2-guanidino)thiophene](9-5)

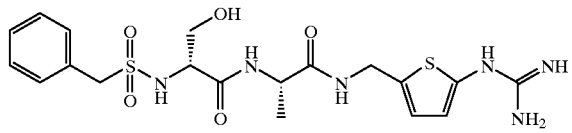

A solution of N-[5-(4-aminometyl)thiophanyl]-N'-(tert-butoxycarbonyl) guanidine (9-4) (77 mg, 0.29 mmol), benzylsulfonyl-D-Serine-L-alanine carboxylate (110 mg, 0.285 mmol), HATU (162 mg, 0.427 mmol), HOAT (58 mg, 0.42 mmol), and DIEA (199 μL, 1.13 mmol) in acetonitrile (3.0 ml) was stirred at ambient temperature overnight. The solution was diluted with EtOAc (20 ml) washed with HCl (1M, 10 ml), NaHCO₃ (saturated, 10 ml), and brine (10 ml). The organic layer was dried over Na₂SO₄ and solvent was removed in vacuo to give an oil. To this oil was added TFA/CH₂Cl₂ (1:1, 2 ml); the mixture was stirred for 3 hours. HPLC purification (CH₃CN, H₂O, 0.1% THF) gave a fluffy white solid corresponding to the title compound (3 mg), MS (electrospray): 483 (M+1).

Example 50
Preparation of 6-Bromomethylnicotinonitrile (11-2)

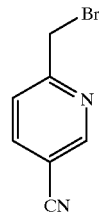

To a solution of 6-Methylnicotinonitrile (11-1) (Lancaster) (15 g, 127 mmol) in carbon tetrachloride (300 ml) was added N-bromosuccinimide (27.12 g, 152.4 mmol). The resulting solution was degassed and purged with nitrogen and AIBN (2,2'-azobisisobutyronitrile) (2.08 g, 12.6 mmol) was added. After 7 hours at 85° C., another batch of AIBN (1.04 g) was added and stirring was continued for another hour. After removal of the solvent the crude product was subjected to flash column chromatography in ethylacetate/hexanes to yield 10 g pure material (40%).

Example 51
Preparation of 6-azidomethylnicotinonitrile (11-3)

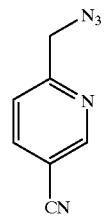

To a solution of 6-Bromomethylnicotinonirile (11-2) (8.0 g, 40.6 mmol) in DMF (100 ml) was added sodium azide (3.17 g, 48.8 mmol). The reaction mixture was stirred overnight at room temperature. The reaction mixture was diluted with 400 ml diethylether and 100 ml water and the layers were separated. The aqueous layer was re-extracted with diethylether (2×100 ml). The combined ether extracts were washed with brine (2×100 ml) and then dried over MgSO4 and filtered to yield 6.53 g product as a white solid.

Example 52
Preparation of 3-hydroxyamidino-6-azidomethylpyridine (11-4)

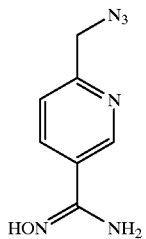

To a solution of the azide of Example 51 (11-3) (6.46 g, 40.6 mmol) in methanol (100 ml) was added hydroxylamine hydrochloride (3.95 g, 56.84 mmol), followed by triethylamine (9.6 ml). The solution was heated to 65° C. for four hours. The solvent was removed under reduced pressure and the remaining residue was extracted with ethylacetate (300 ml) and water (100 ml). The water layer was re-extracted with ethylacetate (2×200 ml). The combined organic extracts were washed with brine (2×100 ml), dried over MgSO$_4$ and evaporated to yield the title product (11-4) (7.8 g).

Example 53

Preparation of 3-hydroxyamidino-6-aminomethylpyridine (11-5)

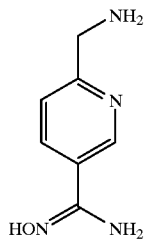

To a solution of the azide (11-4) of Example 52 in THF/water (80 ml/5 ml) (7.8 g, 40.6 mmol) was added triphenylphosphine (12.8 g, 48.72 mmol). The reaction mixture was stirred overnight at room temperature. The solvent was removed to dryness and the remaining residue was diluted with 100 ml 1N HCl and 100 ml water. The aqueous layer was extracted several times with dichloromethane. The aqueous layer was made basic (pH~9) with an alkaline resin (Bio Rad AG 1-X8). The resin was filtered and washed thoroughly with water. The combined washings were dried under reduced pressure to give a white solid (6.60 g).

Example 54

Preparation of 3-Hydroxyamidino-6-aminomethyl(Boc)pyridine (11-6)

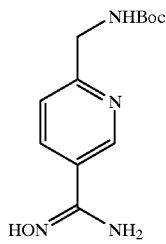

To a solution of the product of Example 53 (11-5) (0.5 g, 3.01 mmol) in dioxane and water (6 ml each) was added potassium carbonate (832 mg, 6.02 mmol), followed by Boc-anhydride (0.66 g, 3.01 mmol). The reaction mixture was stirred overnight at room temperature. The reaction mixture was concentrated and the remaining residue was dissolved in ethylacetate and washed with sodium bicarbonate (saturated) and brine. The organic layer was dried over sodium sulfate, filtered and concentrated. Flash column chromatography in 8/2 ethylacetate/hexanes followed by ethylacetate and 9/1 dichloromethane/methanol afforded 0.43 g product as a white solid. NMR δ (ppm) CDCl$_3$: 8.8 (d, 1H), 7.9 (dd, 1H), 7.3 (d, 1H), 6.6 (bs, 1H), 5.5 (bs, 1H), 4.8 (bs, 1H), 4.4 (d, 2H), 1.4 (s, 9H)

Example 55

Preparation of 3-isopropyloxyamidino-6-aminomethyl(Boc)pyridine (11-7)

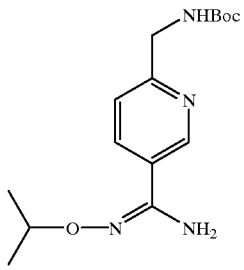

To a solution of the product of Example 54 (11-6) (0.43 g, 1.39 mmol) in dimethylformamide (5 ml) was added 2-iodopropane (210 μl, 2.1 mmol), followed by cesium carbonate (0.68 g, 2.1 mmol). The reaction mixture was stirred overnight at room temperature. The reaction mixture was diluted with ethylacetate and washed with sodium bicarbonate (saturated). The organic layer was dried over sodium sulfate, filtered and concentrated to give an orangish oil. Flash column chromatography performed in 1/1 ethylacetate/hexane followed by ethylacetate yielded 229 mg (53%) product as a crystalline solid. NMR δ (ppm) CDCl$_3$: 8.8 (d, 1H), 7.9 (dd, 1H), 7.3 (d, 1H), 5.5 (bs, 1H), 4.7 (bs, 2H), 4.4 (d, 1H), 1.4 (s, 9H), 1.3 (d, 6H).

Example 56

Preparation of Boc-Ala-3-isopropyloxyamidino-6-aminomethylpyridine (11-8)

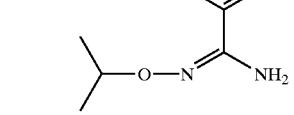

The compound of Example 55 (11-7) (229 mg, 0.74 mmol) was dissolved in dioxane (1 ml) and treated with a solution of 4N HCl in dioxane (1 ml) for one hour at room temperature. Removal of the solvent under reduced pressure afforded 290 mg of a white solid. That product was then dissolved in acetonitrile (4.12 ml), neutralized with diisopropylethylamine (538 μl, 3.09 mmol) and coupled to Boc-alanine (195 mg, 1.03 mmol) using EDC (197 mg, 1.03 mmol) and HOBt (157.6 mg, 1.03 mmol) as coupling reagents. After stirring overnight at room temperature, the solvent was removed under reduced pressure, and the remaining residue was diluted in ethylacetate. The organic layer was washed several times with sodium bicarbonate (saturated) and brine, dried over sodium sulfate, filtered and concentrated to a yellowish oil. Flash column chromatography in 9/1 ethylacetate/hexane, followed by ethylacetate afforded 181 mg of a white oil (46%). NMR δ (ppm) CDC$_{13}$: 8.7 (d, 1H) 7.9 (dd, 1H), 7.3 (d, 1H), 7.1 (bs, 1H), 5.0 (bs, 1H), 4.7 (bs, 2H), 4.6 (d, 2H), 4.3 (m, 1H), 4.1 (m, 1H), 1.4 (s, 9H), 1.39 (d, 3H), 1.3 (d, 6H).

Example 57

Preparation of Benzysulfonyl-dSer(tBu)-Ala-3-isopropyloxyamidino-6-aminomethylpyridine (11-9)

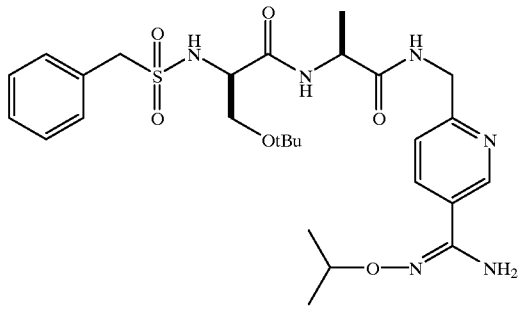

The compound of Example 56 (11-8) (181 mg, 0.48 mmol) was dissolved in dioxane (1 ml) and treated with 4N HCl in dioxane (1 ml) for 1.5 hour at room temperature. Removal of the solvent under reduced pressure afforded 200 mg of a white solid. That product was then dissolved in acetonitrile (5 ml), neutralized with diisopropylethylamine (298 µl, 1.71 mmol) and coupled to BnSO$_2$-dSer (tBu)-OH (180 mg, 0.57 mmol), using EDC (109 mg, 0.57 mmol) and HOBt (96 mg, 0.63 mmol) as coupling reagents. After stirring overnight at room temperature, the solvent was removed under reduced pressure, and the remaining residue was diluted in ethylacetate. The organic layer was washed several times with sodium bicarbonate (saturated) and brine, dried over sodium sulfate, filtered and concentrated to give a solid (250 mg, 76%). The product eluted at 11.5 minutes by reverse phase (C18) HPLC at 0.1% trifluoroacetic acid in 5–75% aqueous acetonitrile over 20 minutes. MS (electrospray): 577 (M+1).

Example 58

Preparation of Benzylsufonyl-dSer-Ala-3-isopropyloxyamidino-6-aminomethylpyridine (11-10)

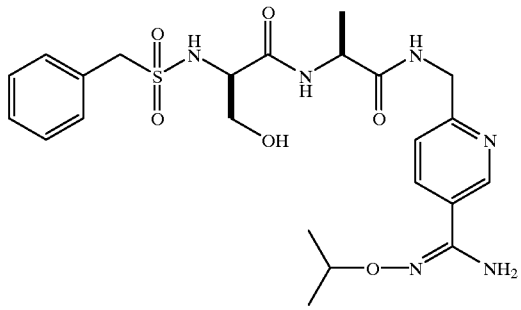

The compound of Example 57 (11-9) (137 mg, 0.24 mmol) was treated with 2 ml each dichloromethane and trifluoroacetic acid for one hour at room temperature. Removal of the solvent under reduced pressure afforded 169 mg of an orangish oil. The product eluted at 9 minutes by reverse phase (C18) HPLC at 0.1% trifluoroacetic acid in 5–90% aqueous acetonitrile over 20 minutes.

Example 59

Preparation of Benzylsulfonyl-dSer-Ala-3-amidino-6-aminomethylpyridine (11-11)

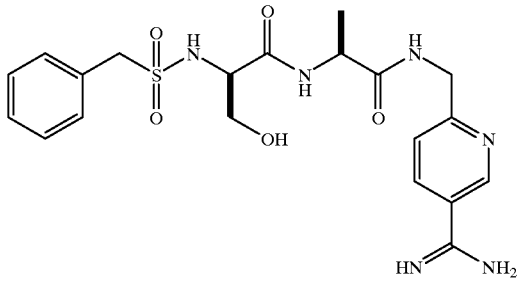

The product of Example 58 (11-10) (74 mg, 0.14 mmol) in water (8 ml) and acetic acid (0.8 ml) was treated with activated zinc dust (91 mg) for 45 minutes. The solution was filtered and the filtrate was subjected to purification by reverse phase HPLC (C18). The product eluted at 11 minutes by reverse phase HPLC at 0.10% trifluoroacetic acid in 5–25% aqueous acetonitrile over 20 minutes. MS (electrospray): 463 (M+1).

B. Synthetic Routes For Certain Intermediate Compounds (i) Examples 60 to 97 describe the synthesis of certain intermediates used in the preparation of compounds of the present invention. See also FIGS. 1 to 5.

Example 60

Preparation of Synthesis of D-Ser(O-t-Bu)-Ala-OMe, Acetate Salt (1-3)

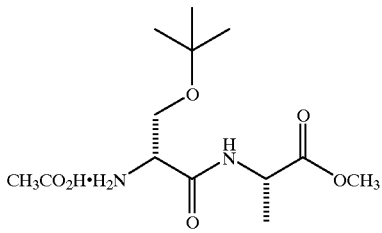

N-α-Cbz-D-serine (1-1) (Bachem, 4.97 g, 16.8 mmol), alanine methyl ester, hydrochloride salt (1-2) (Novabiochem, 4.7 g, 33.7 mmol), EDC (6.5 g, 33.7 mmol), and 1-hydroxybenzotriazole (2.6 g, 16.8 mmol) were combined, and acetonitrile (67 ml) was added. After stirring as a slurry for 10 minutes, diisopropylethylamine (14.4 ml, 84 mmol) was added, and the resulting clear mixture was stirred for an additional 18 hours. The solvent was removed under reduced pressure, and the residue was suspended in ethyl acetate (500 ml). The solution was washed with 0.5M HCl (2×100 ml), followed by saturated sodium bicarbonate (2×100 ml), and brine (100 ml). The organic layer was then dried with sodium sulfate, and the solvent was removed in vacuo to afford Cbz-D-Ser(O-t-Bu)-Ala-OMe in a quantitative yield as a single peak by reverse-phase (C18) HPLC $t_R$=16.9 at 0.1% trifluoroacetic acid in 5–75% aqueous acetonitrile over 20 minutes.

Cbz-D-Ser(O-t-Bu)-Ala-OMe was then dissolved in ethanol/acetic acid/water (150 ml of a 4:1:1 mixture). The flask was charged with nitrogen, and 10% palladium on carbon (1.5 g) was added. This mixture was hydrogenated at 45 psi for 2 hours. The palladium catalyst was filtered, and solvent removed under reduced pressure to give 4.58 g of the title compound in a 95% yield as a single peak by reverse-phase (C18) HPLC ($t_R$=8.0 minutes at 0.1% trifluoroacetic acid in 5–75% aqueous acetonitrile over 20 minutes), and MS (M+H=247.2).

Example 61

Preparation of Benzenesufonyl-D-Ser(O-t-Bu)-Ala-OMe (1-4)

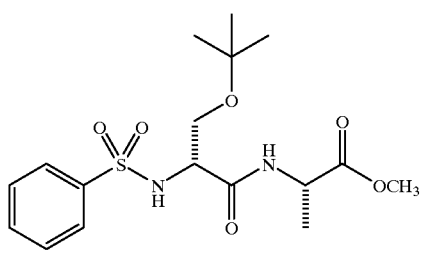

To a stirred slurry of the compound of Example 60 (1-3)(1.0 g, 3.3 mmol) in acetonitrile (13 ml) was added benzenesufonyl chloride (0.87 g, 4.9 mmol). To this mixture diisopropylethylamine(1.67 ml, 9.8 mmol) was added in five portions over a 1 hour period. The mixture was allowed to stir an additional hour. The solvent was removed under reduced pressure, and the residue was suspended in ethyl acetate (100 ml). The solution was washed with 0.5M HCl (2×10 ml), followed by saturated sodium bicarbonate (2×10 ml), and brine (1×10 ml). The organic layer was then dried with sodium sulfate, and solvent was removed under reduced pressure. The residue was purified by flash chromatography eluting with 50% hexanes/ethyl acetate, yielding 0.54 g, 1.4 mmol, of product in a 43% yield. The product was a single peak by reverse phase (C18) HPLC ($t_R$=20.2 minutes at 0.1% trifluoroacetic acid in 5–75% aqueous acetonitrile over 20 minutes). $^1$H NMR(CD$_3$OD) 7.5–7.9 ppm (m, 5H), 4.3 ppm (q, 1H), 3.9 ppm (t, 1H), 3.7(s, 3H), 3.4 ppm (m, 1H),3.5 ppm (m, 1H), 1.3 ppm (d, 3H), 1.05 ppm (s, 9H).

Example 62

Preparation of Benzenesufonyl-D-Ser(O-t-Bu)-Ala-OH (1-5)

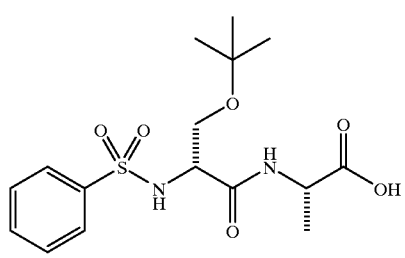

To the compound of Example 61 (1-4) (0.53 g, 1.4 mmol) in methanol (9 ml) was added 1.0M lithium hydroxide (3.0 ml, 3 mmol). After stirring for 18 hours, the reaction mixture was poured over a column of 10 ml of DOWEX (50×8–400) ion exchange resin, and eluted with methanol/water (60 ml of a 1:1 mixture). The methanol was pumped off under reduced pressure and the remaining water was lyophilized, yielding 0.49 g, 1.3 mmol (95%) of the title compound as a single peak by reverse-phase (C18) HPLC ($t_R$=13.5 minutes at 0.1% trifluoroacetic acid in 5–75% aqueous acetonitrile over 20 minutes). $^1$H NMR(CD$_3$OD): 7.9 ppm (d, 2H), 7.6 ppm (t, 1H), 7.5 ppm (t, 2H), 4.25 ppm (q, 1H), 3.9 ppm (t, 1H), 3.5 ppm (m, 1H), 3.4 ppm (m, 1H), 1.3 ppm (d, 3H), 1.075 ppm (s, 9H).

Example 63

Preparation of Benzylsulfonyl-D-Ser(O-t-Bu)-OMe

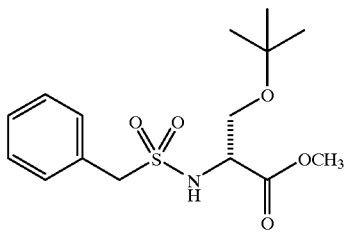

To a stirred solution of D-serine(O-t-Bu) methyl ester, hydrochloride salt (2.07 g, 9.8 mmol) in acetonitrile (39 ml) was added α-toluenesulfonyl chloride (1.86 g, 9.8 mmol). To this mixture of diisopropylethylamine (3.7 ml, 21.5 mmol) were added in five portions over a 1 hour period. The mixture was allowed to stir an additional hour. The solvent was removed under reduced pressure, and the residue was suspended in ethyl acetate (100 ml). The solution was washed with 0.5M HCl (2×10 ml), followed by saturated sodium bicarbonate (2×10 ml), and brine (1×10 ml). The organic layer was dried with sodium sulfate, and solvent was removed in vacuo to give 2.84 g of the title compound in 88% yield. $R_f$=0.4 (4:1 ethyl acetate:hexanes).

Example 64

Preparation of Benzylsulfonyl-D-Ser(O-t-Bu)-OH

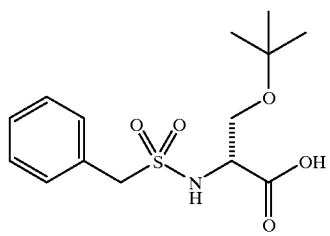

To a stirred solution of the compound of Example 63 (2.66 g, 8.1 mmol) in methanol (54 ml) was added 1.0M lithium hydroxide (17.8 ml, 17.8 mmol). The reaction mixture was allowed to stir for 18 hours, then poured over a column of 10 ml of DOWEX (50×8–400) ion exchange resin and eluted with methanol:water (60 ml of a 1:1 mixture). The methanol was removed under reduced pressure, and the remaining aqueous solution was lyophilized to afford 2.47 g of the title compound in 97% yield. $t_R$=14.8 minutes (0.1% trifluoroacetic acid in 5–75% aqueous acetonitrile over 20 minutes).

Example 65

Preparation of Benzylsulfonyl-D-Ser(O-t-Bu)-Ala-OMe

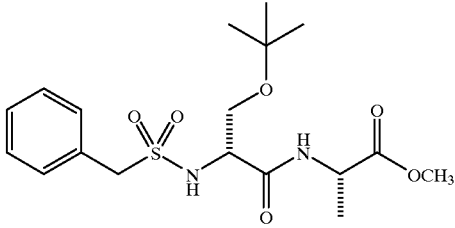

The compound of Example 64 (1.0 g, 3.2 mmol), alanine methyl ester, hydrochloride salt (Novabiochem, 0.89 g, 6.3 mmol), EDC (1.22 g, 6.3 mmol), and 1-hydroxybenzotriazole (0.49 g, 3.2 mmol) were combined and acetonitrile (13 ml) was added. After stirring the resulting slurry for 10 minutes, diisopropylethylamine (2.71 ml, 15.8 mmol) was added and the resulting clear mixture was stirred for an additional 18 hours. The solvent was removed under reduced pressure, and the residue was suspended in ethyl acetate (100 ml). The solution was washed with 0.5M HCl (2×10 ml), followed by saturated sodium bicarbonate (2×10 ml), and brine (1×10 ml). The organic layer was then dried with sodium sulfate, and solvent was removed in vacuo to afford 1.22 g of the title compound in 97% yield. $t_R$=16.$^2$ minutes (0.1% trifluoroacetic acid in 5–75% aqueous acetonitrile over 20 minutes).

Example 66

Preparation of Benzylsulfonyl-D-Ser(O-t-Bu)-Ala-OH

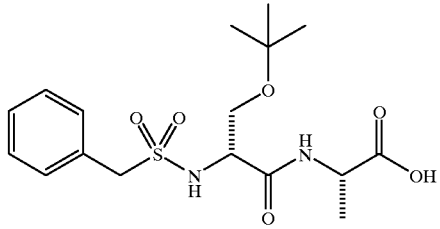

To the compound of Example 65 (1.22 g, 3.1 mmol) in methanol (22 ml), was added 1M lithium hydroxide (7.2 ml, 7.2 mmol). After stirring 18 hours, the reaction mixture was poured over a column of 10 ml of DOWEX (50×8–400) ion exchange resin and eluted with methanol:water (60 ml of a 1:1 mixture). The methanol was removed under reduced pressure, and the aqueous solution was lyophilized to afford 1.16 g of the title compound in 91% yield. $t_R$=13.2 minutes (0.1% trifluoroacetic acid in 5–75% aqueous acetonitrile over 20 minutes).

Example 67

Preparation of i-butoxycarbonyl-D-Ser(O-t-Bu)-OMe

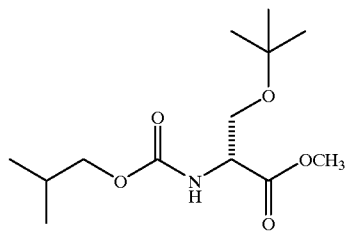

To a stirred homogeneous solution of HCl-D-Ser(O-t-Bu)-OMe (15 g, 71 mmol, Bachem) in tetrahydrofuran (200 ml), was added saturated sodium bicarbonate (80 ml), followed by isobutylchloroformate (19.45 g, 142 mmol). Layers were separated and the aqueous layer was washed with ethyl acetate (50 ml). The organic phases were combined and solvent was removed under reduced pressure. The residue was suspended in ethyl acetate (100 ml) and washed with 1M HCl (100 ml), saturated sodium bicarbonate (100 ml), and brine (100 ml). The organic layer was dried with magnesium sulfate, treated with decolorizing charcoal, (such as that sold under the trade name Darco), filtered, and solvent removed under reduced pressure, giving quantitative yield of the title compound. $R_f$=0.3 (20% ethyl acetate/hexanes).

Example 68

Preparation of i-butoxycarbonyl-D-Ser(O-t-Bu)-OH

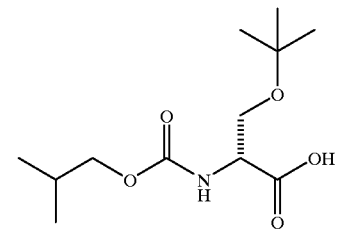

To a stirred solution of the compound of Example 67 (19.51 g, 70 mmol) in tetrahydrofuran (78 ml), was added lithium hydroxide (78 mmol, 3.28 g). The reaction mixture was stirred vigorously for 3 hours until no starting material was observed by TLC (20% ethyl acetate/hexanes). The solution was acidified with concentrated HCl to pH~2 and the solvent removed under reduced pressure. The crude product was suspended in ethyl acetate and extracted with saturated sodium bicarbonate (2X, 75 ml). The combined sodium bicarbonate washes were acidified with 6M HCl and the oil that separated was extracted with ethyl acetate (2×100 ml). The combined organic layers were dried with magnesium sulfate, treated with Darco, filtered, and solvent removed under reduced pressure, giving quantitative yield of the title compound. $R_f$=0.01 (20% ethyl acetate in hexanes).

Example 69
Preparation of i-butoxycarbonyl-D-Ser(O-t-Bu)-Ala-OMe

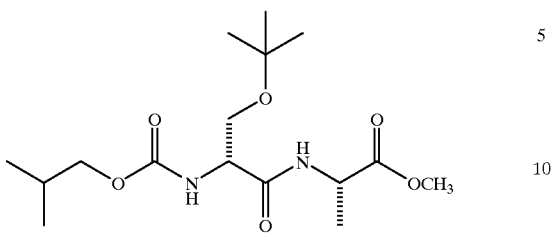

To a solution of the compound of Example 68 (16.5 g, 63 mmol), HCl-Ala-OMe (10.6 g, 76 mmol), 1-hydroxybenzotriazole (10.2 g, 76 mmol), and EDC (16.33 g, 85 mmol) in acetonitrile (280 ml) at 0° C., was added 4-methylmorpholine (35 ml, 315 mmol). This mixture was stirred for 1 hour at 0° C., then at ambient temperature for 72 hours. The solvent was removed under reduced pressure and the resulting residue was suspended in ethyl acetate (300 ml) and 1M HCl (350 ml). The aqueous layer was separated and washed with ethyl acetate (300 ml). The combined ethyl acetate layers were combined and washed with 1M HCl (300 ml), saturated sodium bicarbonate (400 ml), and brine (200 ml). The organic layer was dried with magnesium sulfate, treated with Darco decolorizing charcoal and filtered. The solvent was removed under reduced pressure, yielding 21.48 g of the title compound (98% yield).

Example 70
Preparation of i-butoxycarbonyl-D-Ser-Ala-OH

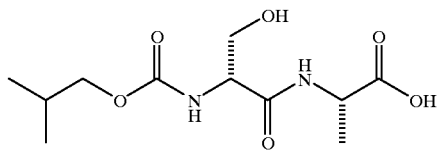

The compound of Example 69 (21 g, 58 mmol) was dissolved in trifluoroacetic acid (110 ml); the resulting mixture was stirred for 35 minutes. The solution was cooled in an ice bath, saturated sodium bicarbonate (630 ml) was added, followed by solid sodium bicarbonate (70 g) over 45 minutes to a resulting pH=7. The aqueous solution was extracted with ethyl acetate (3×250 ml). The combined organic extracts were combined, dried with magnesium sulfate, treated with Darco decolorizing charcoal and filtered. The solvent was removed in vacuo, giving a quantitative yield of i-butoxycarbonyl-D-Ser-Ala-OMe.

To a stirred solution of the crude residue in tetrahydrofuran (68 ml), was added lithium hydroxide (2.7 g, 64 mmol, 1.1 eq.) in water (17 ml). The reaction mixture was stirred vigorously for 0.5 hours until there was no more of the starting material observed by TLC (9:1 dichloromethane/isopropanol). The solution was acidified with 6M HCl (13 ml) to pH~2 and the solvent was removed under reduced pressure. The crude product was suspended in ethyl acetate (400 ml) and water (50 ml). The aqueous layer was extracted with ethyl acetate (200 ml). The combined organic layers were dried with magnesium sulfate, filtered, and the solvent removed in vacuo, yielding 13.94 g of the title compound (86% yield). $R_f$=0.3 (90:30:5 chloroform/methanol/acetic acid).

Example 71
Preparation of N-α-(3-phenylpropyl)-D-serine-t-butyl Ether Methyl Ester

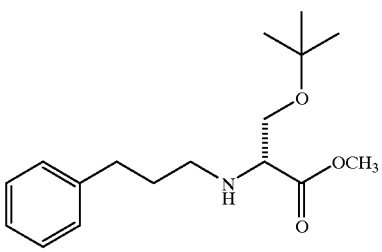

Serine O-t-butyl ether methyl ester (1.50 g, 7.1 mmol), hydrocinnamaldehyde (1.40 ml, 10.6 mmol), and triethylamine (1.18 ml, 8.5 mmol) were refluxed in tetrahydrofuran (70 ml) for 4 hours. After the solution was allowed to cool to room temperature, sodium borohydride (0.46 g, 12 mmol) was added in two portions to the stirred solution. The reaction mixture was stirred at ambient temperature for 30 minutes; the solution was concentrated under reduced pressure. The residue was partitioned between ethyl acetate 1.0M HCl. The organic layer was washed with 1.0N HCl. The aqueous layer was basified with 40%. NaOH to pH 10, then extracted with ethyl acetate (2X). The combined organic layers were dried over sodium sulfate; the solvent was removed in vacuo. The residue was purified by flash chromatography over silica gel (1×6 inch column) eluting with 10–30% ethyl acetate/hexanes to afford 150 mg (7% yield) of the title compound. $R_f$=0.60 (50% ethyl acetate/hexanes).

Example 72
Preparation of N-α-t-butoxycarbonyl-N-α-(3-phenylpropyl)-D-serine-t-butyl Ether Methyl Ester

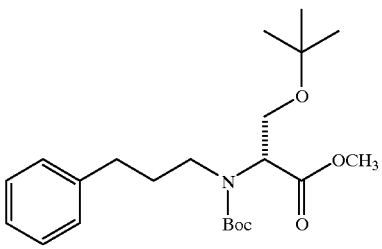

The compound of Example 71 (150 mg, 0.51 mmol), di-t-butyldicarbonate (167 mg, 0.77 mmol) and diisopropylethylamine (0.13 ml, 0.77 mmol) were stirred in tetrahydrofuran (2 ml) at ambient temperature overnight. The reaction mixture was concentrated under reduced pressure. The residue was diluted with ethyl acetate (20 ml), washed successively with 1.0N HCl (2X), saturated sodium bicarbonate (2X), and brine (1X). The solvent was removed in vacuo to afford 206 mg of the title compound in quantitative yield. $R_f$=0.74 (50% ethyl acetate/hexanes).

Example 73
Preparation of N-α-t-butoxycarbonyl-N-α-(3-phenylpropyl)-D-serine-t-butyl Ether

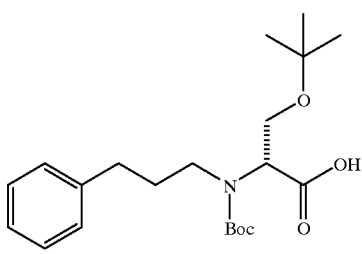

To a solution of the compound of Example 72 (206 mg, 0.52 mmol) in methanol (3.5 ml), was added dropwise 1.0N LiOH (0.63 ml, 0.63 mmol). The solution became cloudy, then became homogeneous in 5 minutes. The reaction mixture was allowed to stir at ambient temperature overnight. Additional 1.0N LiOH (1.47 ml) was added. After 2 hours, additional 1.0N LiOH (1.0 ml) was added. After no starting material was observed by TLC (50% ethyl acetate/hexanes), the reaction mixture was acidified to pH4 with DOWEX (50×8-400) ion exchange resin. The solution was filtered, rinsing with methanol, then water. The solution was concentrated under reduced pressure, then lyophilized to afford 189 mg of the title compound in 95% yield as a yellow oil. $R_f$=0.04 (50% ethyl acetate/hexanes).

Example 74
Preparation of i-butoxycarbonyl-D-Ser(O-t-butyl)-OH (2-2)

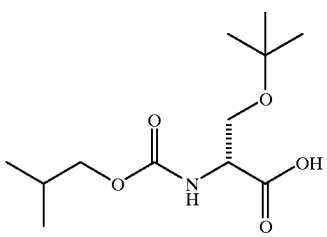

To a solution of D-serine-O-t-butyl ether (2-1) (10.5 g, 65.3 mmol) in water (51 ml) was added sodium carbonate (20.1 g, 196.2 mmol) followed by isobutyl chloroformate (9.8 ml, 75.2 mmol). After 3 hours this mixture became cloudy and was stirred for an additional 3 hours. After 6 hours the solution was acidified with 6M HCl (~50 ml). The reaction mixture was then extracted with ethyl acetate (3×200 ml). After the initial extraction, the aqueous layer was saturated with sodium chloride and extracted with ethyl acetate (2×200 ml). The ethyl acetate layers were combined and dried with sodium sulfate, followed by removal of the solvent in vacuo, yielding 17.0 g (99.5% yield) of the title compound as a white solid. HPLC: t=18.5 minutes in a 5% to 75% acetonitrile gradient in 0.1% aqueous TFA buffer on a 4.6×250 mm, 5 micron particle, 100 angstrom pore, C18 column at a 1 ml/minute flow rate. NMR(CDCl$_3$): 5.5 ppm (m, 1H), 4.45 ppm (bs, 1H), 3.82–3.95 ppm (m, 3H), 3.52–3.6 ppm (m, 1H), 1.85–1.97 ppm (m, 1H), 1.2 ppm (s, 9H), 0.9 ppm (d, 6H).

Example 75
Preparation of i-butoxycarbonyl-D-Ser(t-Bu)-L-Ala-O-t-Bu (2-3)

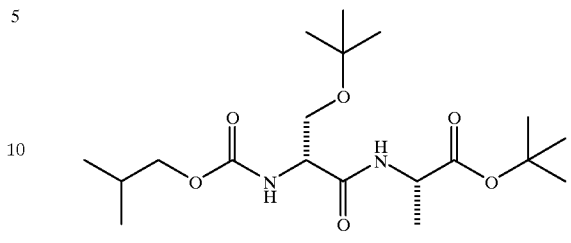

A solution of the compound of Example 74 (2-2) (10 g, 38.3 mmol), L-alanine t-butyl ester, HCl salt (10.43 g, 57.4 mmol), EDC (11.05 g, 57 mmol), and hydroxybenzotriazole (5.85 g, 38.3 mmol) in acetonitrile (153 ml) was stirred for 15 minutes at room temperature. Diisopropylethylamine (32.7 ml, 191 mmol) was added and the reaction mixture stirred for 18 hours. The solvent was removed under reduced pressure; the resulting residue was resuspended in ethyl acetate (1000 ml) and 1M HCl (100 ml). The ethyl acetate layer was washed with 0.5M HCl (100 ml), saturated with sodium bicarbonate (2×100 ml), and brine (100 ml). The ethyl acetate layer was dried with sodium sulfate and solvent was removed in vacuo, resulting in a quantitative yield of title compound. HPLC: $t_r$=18.7 minutes in a 5% to 90% acetonitrile gradient in 0.1% aqueous TFA buffer on a 4.6×250 mm, 5 micron particle, 100 angstrom pore, C18 column at a 1 ml/minute flow rate. NMR(CDCl$_3$): 7.15 ppm (bs, 1H), 5.6 ppm (bs, 1H), 4.4–4.5 ppm (m, 1H), 4.2 ppm (bs, 1H), 3.87–3.95 ppm (m, 3H), 3.3–3.4 ppm (m, 1H), 1.85–1.95 ppm (m, 1H), 1.45 ppm (s, 9H), 1.39 ppm (d, 3H), 1.2 ppm (s, 9H), 0.9 ppm (d, 6H).

Example 76
Preparation of i-butoxycarbonyl-D-Ser-L-Ala-OH (2-4)

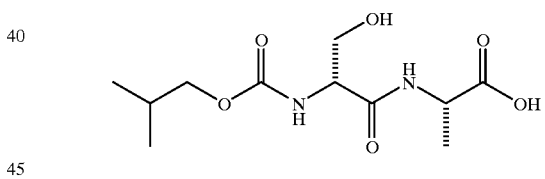

To a solution of the compound of Example 75 (2-3) (7.15 g, 18.4 mmol) in dichloromethane (35 ml), was added trifluoroacetic acid (35 ml). This mixture was stirred for two hours, then solvent was removed under reduced pressure. Toluene was added and the solvents were removed in vacuo to remove the trifluoroacetic acid. A quantitative yield of the title compound as a viscous yellow oil was then carried on to the next step. $t_r$=10.5 minutes in a 5% to 90% acetonitrile gradient in 0.1% aqueous TFA buffer on a 4.6×250 mm, 5 micron particle, 100 angstrom pore, C18 column at a 1 ml/minute flow rate.

Example 77
Preparation of 2-cyano-5-methylthiophene (3-2)

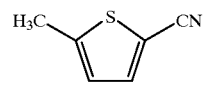

A solution of 2-bromo-5-methylthiophene (3-1) (TCI chemicals, 5 g, 28 mmol) and copper(I) cyanide (Aldrich, 2.53 g, 28 mmol) in DMF (10 ml) was heated at reflux for 4 hours. After cooling to ambient temperature, ethyl acetate (500 ml) and a 10% NaCN aqueous solution (500 ml) was added. After separation of aqueous and organic layers, the aqueous layer was extracted with ethyl acetate (300 ml). The combined organic layers were concentrated to an oil, which was further purified by a flash column chromatography (ethyl acetate) to give the title compound (3.03 g, 87%). TLC: Rf 0.30 (1:1 of hexane/ethyl acetate); $^1$H NMR (CDCl$_3$): δ 2.55 (m, 3H), 6.76 (d, 1H, J=3.6 Hz), 7.42 (d, 1H, J=3.6 Hz).

Example 78

Preparation of 2-cyano-5-(bromomethyl)thiophene (3-3)

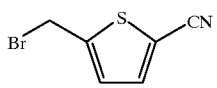

A solution of 2-cyano-5-methylthiophene (compound 3-2, 3.0 g, 24 mmol), N-bromosuccinimide (Aldrich, 4.8 g, 27 mmol), and 2,2'-azobisisobutyronitrile (Aldrich, 0.4 g, 2.4 mmol) in CCl$_4$ (Aldrich, 60 ml) was heated at reflux for 5 hours. After cooling to ambient temperature, the solvent was removed under vacuum to give a yellow oil. The oil was purified by a flash column chromatography (1:1 hexane/ethyl acetate) to give the title compound (4.5 g, 91%). TLC: Rf 0.91 (1:1 of hexane/ethyl acetate); $^1$H NMR (CDCl$_3$): δ 4.66 (s, 2H), 7.10 (d, 1H, J=3.8 Hz), 7.48 (d, 1H, J=3.8 Hz).

Example 79

Preparation of 2-cyano-5-(azidomethyl)thiophene (3-4)

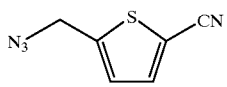

A solution of 2-cyano-5-(bromomethyl)thiophene (compound 3-3, 3.5 g, 17.3 mmol) and sodium azide (Aldrich, 1.7 g, 26 mmol) in DMF (Aldrich, 60 ml) was stirred at ambient temperature for 10 hours. Flash column chromatography (20% ethyl acetate in hexane) gave the title compound (2.35 g, 83%). TLC: Rf 0.48 (20% of ethyl acetate in hexane); $^1$H NMR (CDCl$_3$): δ 4.56 (s, 2H), 7.01 (d, 1H, J=3.7 Hz), 7.55 (d, 1H, J=3.7 Hz).

Example 80

Preparation of 2-cyano-5-(aminomethyl)thiophene (3-5)

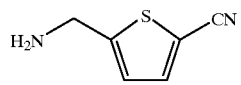

Triphenylphosphine (Aldrich, 5.7 g) was added to a solution of 2-cyano-5-(azidomethyl)thiophene (compound 3-4, 2.5 g, 10 mmol) in THF (Aldrich, 40 ml) and water (10 ml) at 0° C. The solution was allowed to warm to room temperature and stirred at ambient temperature for 10 hours. RP-HPLC purification gave the title compound (2.3 g, 94%). MS (electrospray): 139 (M+1); $^1$H NMR (CDCl$_3$): δ 4.01 (s, 2H), 4.75 (br s, 2H, NH$_2$), 6.82 (d, 1H, J=3.5 Hz), 7.08 (d, 1H, J=3.5 Hz).

Example 81

Preparation of 2-cyano-5-(t-butoxycarbonylaminomethyl)thiophene (3-6)

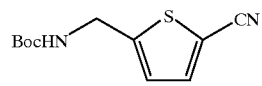

Potassium carbonate (Aldrich, 2 g) was added to a solution of 2-cyano-5-(aminomethyl)thiophene (compound 3-5, 0.6 g, 4 mmol), Boc$_2$O (Fluka, 0.95 g, 4 mmol) in water (4 ml) and 1,4-dioxane (Aldrich). The resulting mixture was stirred at ambient temperature for 12 hours. Flash chromatography (1:1 hexane/ethyl acetate) gave the title compound (0.58 g, 56%). MS (electrospray): 239 (M+1); $^1$H NMR (CDCl$_3$): δ 1.44 (s, 9H), 4.55 (s, 2H), 4.90 (br s, 1H, NH), 6.88 (d, 1H, J=3.6 Hz), 7.07 (d, 1H, J=3.6 Hz).

Example 82

Preparation of 2-(N-hydroxyamidinyl)-5-(t-butoxycarbonylaminomethyl)thiophene (3-7)

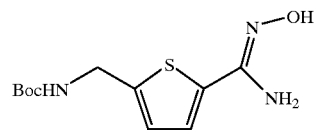

A solution of 2-cyano-5-(t-butoxycarbonylmethyl)thiophene (compound 3-6, 560 mg, 2.44 mmol), hydroxylamine hydrochloride (Aldrich, 330 mg, 4.8 mmol) and 4-methylmorpholine (Aldrich, 1 ml, 9.1 mmol) in methanol (5 ml) was stirred at ambient temperature for 12 hours. Flash chromatography (5:95:1 isopropyl alcohol/methylene chloride/triethylamine) gave the title compound (550 mg, 86%). MS (electrospray): 272 (M+1).

Example 83

Preparation of 2-amidinyl-5-(aminomethyl)thiophene (3-8)

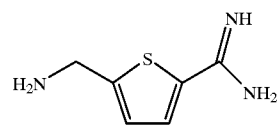

10% Pd-on-C (Aldrich, 100 mg) was added to a solution of 2-(N-Hydroxyamidinyl)-5-(t-butoxycarbonylaminomethyl)thiophene (compound 3-7, 900 mg, 3.3 mmol) in methanol (10 ml). The resulting mixture was hydrogenated (45 psi of H$_2$) in a Parr apparatus at room temperature for 10 hours. The catalyst was removed by filtering and the solvent was evaporated under vacuum to give the Boc protected intermediate [900 mg, 94%, MS (electrospray) 256 (M+1)] which was treated with 4 M HCl in 1,4-dioxane (Aldrich, 5 ml) for 3 hours at ambient temperature to yield the title compound (460 mg, 84%). MS (electrospray): 56 (M+1); $^1$H NMR (CD$_3$OD): δ 4.43 (s, 2H), 7.42 (d, 1H, J=3.5 Hz), 7.78 (d, 1H, J=3.5 Hz)

Example 84
Preparation of 2-[N-(propyloxy)amidinyl]-5-(aminomethyl)thiophene (3-9)

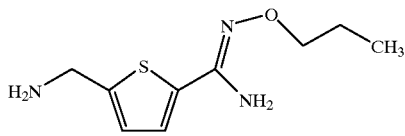

CsCO₃ (Aldrich, 0.5 g) was added to a solution of 2-(N-Hydroxyamidinyl)-5-(t-butoxycarbonylaminomethyl)thiophene (compound 3-7, 271 mg, 1.0 mmol) and iodopropane (Aldrich, 200 mg, 1.2 mmol) in DMF. The reaction mixture was stirred at ambient temperature for 10 hours. Flash chromatography (5:95:1 isopropyl alcohol/methylene chloride/triethylamine) gave the Boc protected intermediate [MS (electrospray) 314 (M+1)] which was treated with 4M HCl in 1,4-dioxane (Aldrich) for 3 hours at ambient temperature to yield the title compound (201 mg, 81). MS (electrospray): 214 (M+1); ¹H NMR (CDCl₃): δ 0.95 (t, 3H, J=7.5 Hz), 1.55 (br s, 2H, NH₂), 1.70 (m, 2H), 4.00 (t, 2H, J=7.5 Hz), 4.01 (d, 2H, J=7.5 Hz), 4.70 (br s, 2H, NH₂), 6.80 (d, 1H, J=3.6 Hz), 7.08 (d, 1H, J=3.6 Hz)

Example 85
Preparation of α-azido-4-cyanotoluene (4-2)

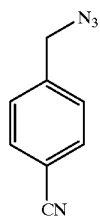

Sodium azide (Aldrich, 3.5 g, 54 mmol) was added to a solution of p-cyanobenzyl bromide (Aldrich, 10 g, 51 mmol) in DMF (100 ml), and the resulting mixture was stirred at ambient temperature for 5 hours. The reaction mixture was then diluted with water (350 ml) and extracted with ether (2×100 ml). Combined organic layers were washed with brine and dried (MgSO₄). Removal of solvent gave the title compound (8 g, 96%). ¹H NMR (CDCl₃): δ 4.42 (s, 2H), 7.41 (d, 2H, J=8.1 Hz), 7.65 (d, 2H, J=8.1 Hz).

Example 86
Preparation of p-cyanobenzylamine (4-3)

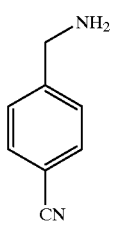

10% Pd-on-C (Aldrich, 800 mg) catalyst was added to a solution of α-azido-4-cyanotoluene (compound 4-2, 8 g, 51 mmol) in EtOAc (150 ml). The reaction mixture was hydrogenated (H₂, 45 psi) in a Parr apparatus for 11 hours. Catalyst was removed by filtering and the solvent was removed under vacuum to give the title compound (6.3 g, 93%). ¹H NMR (CDCl₃): δ 3.85 (s, 2H), 7.45 (d, 2H, J=8.1), 7.60 (d, 2H, J=8.1 Hz), 7.78 (s, 2H, NH₂).

Example 87
Preparation of 4-(aminomethyl)phenyl-N-hydroxyamidine (4-4)

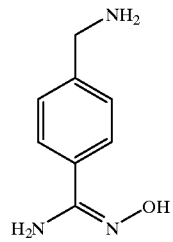

Hydroxylamine hydrochloride (7 g) was added to a solution of compound 4-3 (7 g) and NMM (4 ml) in methanol (100 ml). The mixture was stirred at ambient temperature for 3 days. The compound was purified by RP HPLC to give the title compound (7 g, 89%). MS (electrospray): 166 (M+1).

Example 88
Preparation of 4-(aminomethyl)phenylamidine (4-5)

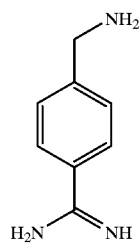

10% Pd-on-C (Aldrich, 800 mg) was added to a solution of 4-(aminomethyl)phenyl-N-hydroxyamidine (compound 4-4, 7 g) in methanol (150 ml). The reaction mixture was hydrogenated (H₂, 45 psi) in a Parr apparatus for 48 hours. Catalyst was removed by filtering and the solvent was removed under vacuum to give the title compound (6.3 g, 99%). MS (electrospray): 150 (M+1).

Example 89
Preparation of 2-fluoro-4-cyanotoluene (5-2)

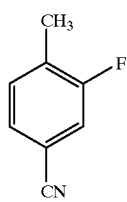

Copper(I) cyanide (Aldrich, 3.6 g, 40 mmol) was added to a solution of 4-bromo-2-fluorotoluene (Aldrich, 5 g, 27 mmol) in DMF (60 ml). The reaction mixture was heated at 150° C. for 11 hours. After cooling to room temperature, the mixture was partitioned between water and EtOAc (500 ml each). The organic layer was dried (MgSO₄), and solvent was removed under vacuum to give the title compound (2.08, 58%). ¹H NMR (CDCl₃) δ 2.36 (s, 3H), 7.30 (m, 3H), 7.35 (d, 1H, J=8.1 Hz).

Example 90
Preparation of 3-fluoro-4-(bromomethyl)benzonitrile (5-3)

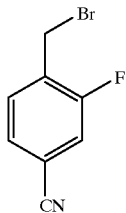

NBS (Aldrich, 3.02 g, 17 mmol) and benzoylperoxide (Aldrich, 0.37 g, 1.5 mmol) was added to a solution of 2-fluoro-4-cyanotoluene (compound 5-2, 2.08 g, 15 mmol) in CCl$_4$. The reaction mixture was heated at 80° C. for 14 hours. After cooling down to ambient temperature, the mixture was diluted with ether (100 ml) and washed with aqueous Na$_2$S$_3$O$_3$, and dried (MgSO$_4$). Removal of solvent under vacuum led to a yellow oil which was purified by flash chromatography. The title compound 5-3 (1.4 g, 42%) was obtained, together with a by-product, 3-fluoro-4-(bromomethyl)benzonitrile (5-4) (1.0 g, 30%). For the title compound (5-3): 1H NMR (CDCl$_3$): δ 4.46 (s, 2H), 7.35 (d, 1H, J=8.0 Hz), 7.42 (d, 1H, J=8.0 Hz), 7.52 (t, 1H, J=8.0 Hz). For the by-product (5-4): $^1$H NMR (CDCl$_3$): δ 6.90 (s, 1H), 7.35 (d, 1H, J=8.0 Hz), 7.55 (d, 1H, J=8.0 Hz), 7.96 (t, 1H, J=8.0 Hz).

Example 91
Preparation of 3-fluoro-4-(azidomethyl)benzonitrile (5-5)

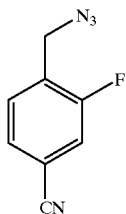

Sodium azide (Aldrich, 0.63 g, 9.8 mmol) was added to a solution of 3-fluoro-4-(bromomethyl)benzonitrile (compound 5-3, 1.4 g, 6.5 mmol) in DMF (15 ml). After stirring at ambient temperature for 20 hours, the reaction mixture was partitioned in EtOAc and water (100 ml, each). Organic layer was then dried (MgSO$_4$), and solvent was removed under vacuum to give the title compound (0.995 g, 86%). $^1$H NMR (CDCl$_3$): δ 4.50 (s, 2H), 7.38 (d, 2H, J=8.1 Hz), 7.52 (m, 2H)

Example 92
Preparation of 3-fluoro-4-(azidomethyl)-phenyl-N-hydroxyamidine (5-6)

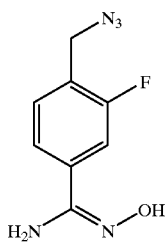

Hydroxylamine hydrochloride (Aldrich, 800 mg, 11.6 mmol) was added to a solution of 3-fluoro-4-(azidomethyl)benzonitrile (compound 5-5, 1.2 g, 6.8 mmol) and NMM (2 ml) in methanol (25 ml). After stirring at room temperature for 3 days, the reaction mixture was diluted with EtOAc and washed with brine. Removal of solvent under vacuum yielded the title compound (1.38, 82%). $^1$H NMR (CD$_3$OD): δ 4.41 (s, 2H), 7.45 (m, 3H)

Example 93
Preparation of 3-fluoro-4-(azidomethyl)phenyl(-N-propyloxy)amidine (5-7)

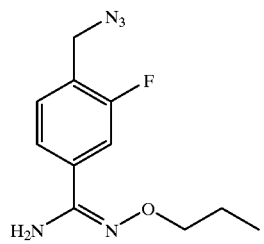

Cesium carbonate (Aldrich, 3.2 g, 9.9 mmol) was added to a solution of iodopropane (1 ml, 10 mmol) and 3-fluoro-4-(azidomethyl)phenyl-N-hydroxyamidine (compound 5-6, 1.38 g, 6.6 mmol) in DMF (20 ml). The reaction mixture was heated at 50° C. for 20 hours. After cooling down to ambient temperature, water was added and resulting mixture was extracted with ether. The organic layer was washed with brine and dried (MgSO$_4$). Flash chromatography gave the title compound (1.03 g, 62%). $^1$H NMR (CDCl$_3$): δ 0.99 (t, 3H, J=7.5 Hz), 1.75 (m, 2H), 4.08 (t, 2H, J=7.5 Hz), 4.40 (s, 2H), 4.78 (br s, 2H), 7.40 (m, 3H).

Example 94
Preparation of 3-fluoro-4-(aminomethyl)phenyl(-N-propyloxy)amidine (5-8)

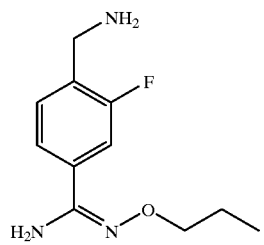

Triphenylphosphine (Aldrich, 1.6 g, 6.2 mmol) was added to a solution of 3-fluoro-4-(azidomethyl)phenyl(-N-propyloxy)amidine (compound 5-7, 1.03 g, 4.1 mmol) in THF (15 ml). The reaction mixture was stirred at ambient temperature for 20 hours. NaOH (3M) was added to the reaction mixture until pH=14. The resulting solution was extracted with EtOAc (2×100 ml). The combined organic layers were washed brine and dried (MgSO$_4$). Removal of solvent under vacuum gave the title compound (825 mg, 77%). $^1$H NMR (CD$_3$OD): δ 0.98 (t, 3H, J=7.5 Hz), 1.72 (m, 2H), 3.82 (s, 2H), 3.95 (t, 2H, J=7.5 Hz), 7.35 (d, 1H, J=8.0 Hz), 7.40 (m, 2H)

Example 95
Preparation of N-α-benzyloxycarbonyl-D-Ser(O-t-butyl)-L-Ala t-butyl Ester

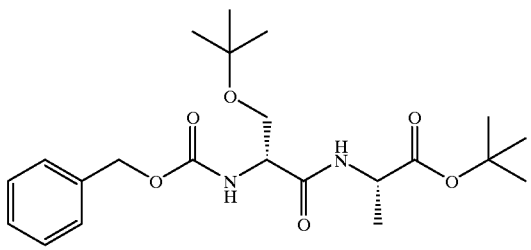

To a solution of N-α-Cbz-D-serine t-butyl ether (5.02 g, 17 mmol) in acetonitrile (100 ml) was added EDC (4.90 g, 25.5 mmol, 1.5 equiv) and 1-hydroxybenzotriazole (2.60 g, 17 mmol). After stirring for 45 minutes, alanine t-butyl ester, HCl salt (3.55 g, 19.6 mmol, 1.15 equiv) and 4-methylmorpholine (7.5 ml, 68 mmol, 4 equiv) were added. The reaction mixture was stirred for 1.5 hours. TLC indicated the reaction was complete. The reaction mixture was concentrated under reduced pressure. The residue was dissolved in ethyl acetate (100 ml), then washed successively with 1N HCl, saturated sodium bicarbonate, water and brine (25 ml each). The solvent was removed in vacuo to give an oil which crystallized on standing. The title compound (6.95 g) was obtained as a pale yellow solid in 97% yield. $R_f$=0.63 (5% isopropanol in dichloromethane).

Example 96
Preparation of D-Ser(O-t-butyl)-L-Ala t-butyl Ester

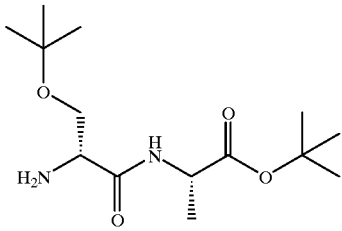

A solution of the compound of Example 95 (1.14 g, 2.69 mmol) in methanol was hydrogenated over palladium hydroxide (110 mg) at balloon pressure for 1.5 hours. The reaction mixture was filtered through celite, and the solvent was removed in vacuo to afford the title compound in quantitative yield as a yellow oil. $R_f$=0.44 (5% methanol in dichloromethane).

Example 97
Preparation of Phenethylsulfonyl-D-Ser(O-t-butyl)-L-Ala t-butyl Ester

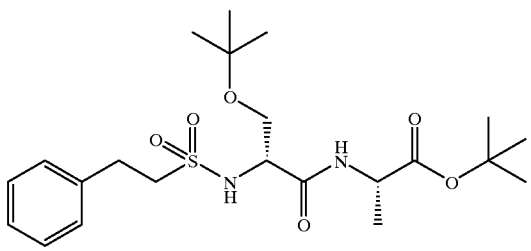

To a stirred solution of the compound of Example 96 (4.2 g, 14.6 mmol) and phenethylsulfonyl chloride (3.58 g, 17.5 mmol, 1.2 equiv) in acetonitrile (100 ml) cooled in an ice bath, was added 2,4,6-collidine (4.8 ml, 36.5 mmol, 2.5 equiv). The reaction mixture was allowed to warm to room temperature, then stirred overnight. The reaction mixture was concentrated under reduced pressure. The residue was dissolved in ethyl acetate (80 ml); the resulting solution was washed successively with 1.0N HCl, saturated sodium bicarbonate, water and brine, then dried over sodium sulfate. The solvent was removed in vacuo. The residue was chromatographed through silica gel eluting with 0–60% ethyl acetate/hexanes. The title compound was isolated in 89% yield as a yellow oil. $R_f$=0.84 (5% methanol in dichloromethane).

C. Synthetic Routes for Compounds Having Acyl or Carbonate Esters at P3

Example 98
Preparation of n-butylsulfonyl-D-(isopropyloxycarbonyl)serine-alanine-4-amidinobenzylamide

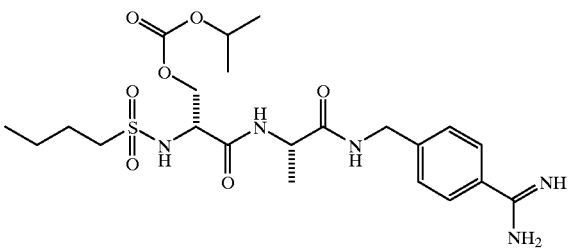

To a solution of the compound of Example 9 (2.32 g, 4.3 mmol) in pyridine (100 ml) cooled in an ice bath, is added isopropyl chloroformate (21 ml of a 1M solution in toluene, 21 mmol, 5 equiv). The reaction is monitored until determined to be complete by analytical HPLC. The reaction mixture is diluted with toluene (300 ml); the solvent is removed under reduced pressure. The residue is dissolved in acetonitrile (400 ml) and the solvent is removed under reduced pressure. The residue is dissolved in acetonitrile (30 ml) and ethyl acetate (30 ml). Ether was added, and the precipitate was isolated. The solid is washed with ether, then dried in vacuo. The solid is washed with ether and ethyl acetate (2×200 ml of a 1:1 mixture), then dried in vacuo to give the title compound.

Example 99
Following the protocol of Example 98, with the noted substitution for isopropyl chloroformate, the following compounds are prepared:

| compound name | Substitution in Example 99 |
|---|---|
| n-butylsulfonyl-D-[(+)-menthyloxycarbonyl]-serine-alanine-4-amidinobenzylamide | (+)-menthyl chloroformate |
| n-butylsulfonyl-D-(phenoxycarbonyl)-serine-alanine-4-amidinobenzylamide | phenyl chloroformate |

Example A
In vitro Enzyme Assays for Specificity Determination

The ability of compounds of the present invention to act as selective inhibitors of urokinase catalytic activity was assessed by determining the concentration of test compound which inhibited the activity of this enzyme by 50%, ($IC_{50}$), and comparing this value to that determined for all or some of the following related serine proteases: recombinant tissue plasminogen activator (rt-PA), plasmin, activated protein C, chymotrypsin, factor Xa, thrombin and trypsin.

The buffer used for all assays was HBSA (10 mM HEPES, pH 7.5, 150 mM sodium chloride, 0.1% bovine serum albumin).

The assay for $IC_{50}$ determinations was conducted by combining in appropriate wells of a Corning microtiter plate, 50 microliters of HBSA, 50 microliters of the test compound at a specified concentration (covering a broad concentration range) diluted in HBSA (or HBSA alone for VO (uninhibited velocity) measurement), and 50 microliters of the enzyme diluted in HESA. Following a 30 minute incubation at ambient temperature, 50 microliters of the substrate at the concentrations specified below were added to the wells, yielding a final total volume of 200 microliters (about 4 times Km). The initial velocity of chromogenic substrate hydrolysis was measured by the change in absorbance at 405 nm using a Thermo Max® Kinetic Microplate Reader over a 5 minute period in which less than 5% of the added substrate was utilized. The concentration of added inhibitor which caused a 50% decrease in the initial rate of hydrolysis was defined as the $IC_{50}$ value. $K_i$ may be calculated from the $IC_{50}$ value.

Urokinase Assay

Urokinase catalytic activity was determined using the chromogenic substrate 150 mM S-2444 (L-Pyroglutamyl-glycyl-L-arginine-p-nitroaniline hydrochloride), obtained from DiaPharma Group, Inc. Urokinase (Abbokinase), manufactured by Abbott Laboratories, was obtained from Priority Pharmaceuticals and diluted to 750 pM in the HBSA assay buffer prior to use. The assay buffer was HBS (10 mM HEPES, 150 mM sodium chloride pH 7.4) with 0.1% BSA. $K_i$ was calculated using the $IC_{50}$ value.

Thrombin (fIIa) Assay

Enzyme activity was determined using the chromogenic substrate, Pefachrome t-PA ($CH_3SO_2$-D-hexahydrotyrosine-glycyl-L-Arginine-p-nitroaniline, obtained from Pentapharm Ltd.). The substrate was reconstituted in deionized water prior to use. Purified human α-thrombin was obtained from Enzyme Research Laboratories, Inc. The buffer used for all assays was HBSA (10 mM HEPES, pH 7.5, 150 mM sodium chloride, 0.1% bovine serum albumin).

$IC_{50}$ determinations were conducted where HBSA (50 μL), α-thrombin (50 μl) (the final enzyme concentration is 0.5 nM) and inhibitor (50 μl) (covering a broad concentration range), were combined in appropriate wells and incubated for 30 minutes at room temperature prior to the addition of substrate Pefachrome-t-PA (50 μl) (the final substrate concentration is 250 μM, about 5 times Km). The initial velocity of Pefachrome t-PA hydrolysis was measured by the change in absorbance at 405 nm using a Thermo Max© Kinetic Microplate Reader over a 5 minute period in which less than 5% of the added substrate was utilized. The concentration of added inhibitor which caused a 50% decrease in the initial rate of hydrolysis was defined as the $IC_{50}$ value.

Factor Xa

Factor Xa catalytic activity was determined using the chromogenic substrate S-2765 (N-benzyloxycarbonyl-D-arginine-L-glycine-L-arginine-p-nitroaniline), obtained from DiaPharma Group (Franklin, Ohio). All substrates were reconstituted in deionized water prior to use. The final concentration of S-2765 was 250 μM (about 5-times Km). Purified human Factor X was obtained from Enzyme Research Laboratories, Inc. (South Bend, Ind.) and Factor Xa (FXa) was activated and prepared from it as described [Bock, P. E., Craig, P. A., Olson, S. T., and Singh, P., Arch. Biochem. Biophys. 273:375–388 (1989)]. The enzyme was diluted into HBSA prior to assay in which the final concentration was 0.25 nM.

Recombinant Tissue Plasminogen Activator (rt-PA) Assay rt-PA catalytic activity was determined using the substrate, Pefachrome t-PA ($CH_3SO_2$-D-hexahydrotyrosine-glycyl-L-arginine-p-nitroaniline, obtained from Pentapharm Ltd.). The substrate was made up in deionized water followed by dilution in HBSA prior to the assay in which the final concentration was 500 micromolar (about 3-times Km). Human rt-PA (Activase®) was obtained from Genentech Inc. The enzyme was reconstituted in deionized water and diluted into HBSA prior to the assay in which the final concentration was 1.0 nM.

Plasmin Assay

Plasmin catalytic activity was determined using the chromogenic substrate, S-2366 [L-pyroglutamyl-L-prolyl-L-arginine-p-nitroaniline hydrochloride], which was obtained from DiaPharma Group. The substrate was made up in deionized water followed by dilution in HBSA prior to the assay in which the final concentration was 300 micromolar (about 2.5-times Km). Purified human plasmin was obtained from Enzyme Research Laboratories, Inc. The enzyme was diluted into HBSA prior to assay in which the final concentration was 1.0 nM.

Activated Protein C (aPC) Assay aPC catalytic activity was determined using the chromogenic substrate, Pefachrome PC (delta-carbobenzyloxy-D-lysine-L-prolyl-L-arginine-p-nitroaniline dihydrochloride), obtained from Pentapharm Ltd.). The substrate was made up in deionized water followed by dilution in HBSA prior to the assay in which the final concentration was 400 micromolar (about 3 times Km). Purified human aPC was obtained from Hematologic Technologies, Inc. The enzyme was diluted into HBSA prior to assay in which the final concentration was 1.0 nM.

Chymotrypsin Assay

Chymotrypsin catalytic activity was determined using the chromogenic substrate, S-2586 (methoxy-succinyl-L-arginine-L-prolyl-L-tyrosyl-p-nitroanilide), which was obtained from DiaPharma Group. The substrate was made up in deionized water followed by dilution in HBSA prior to the assay in which the final concentration was 100 micromolar (about 9-times Km). Purified (3x-crystallized; CDI) bovine pancreatic α-chymotrypsin was obtained from Worthington Biochemical Corp. The enzyme was reconstituted in deionized water and diluted into HBSA prior to assay in which the final concentration was 0.5 nM.

Trysin Assay

Trypsin catalytic activity was determined using the chromogenic substrate, S-2222 (benzoyl-L-isoleucine-L-glutamic acid-[gamma-methyl ester]-L-arginine-p-nitroanilide), which was obtained from DiaPharma Group. The substrate was made up in deionized water followed by dilution in HBSA prior to the assay in which the final concentration was 250 micromolar (about 4-times Km). Purified (3x-crystallized; TRL3) bovine pancreatic trypsin was obtained from Worthington Biochemical Corp. The enzyme was reconstituted in deionized water and diluted into HBSA prior to assay in which the final concentration was 0.5 nM.

Table I

Table I lists the determined $K_i$ or $IC_{50}$ values for certain of the enzymes listed above for compounds of the present invention that demonstrate a high degree of specificity for the inhibition of urokinase compared to other serine proteases.

TABLE I

| Compound | Ki uPA* | IC50 tPA* | IC50 Plasmin* |
|---|---|---|---|
| A | A | D | D |
| B | C | D | E |
| C | C | E | D |
| D | B | D | D |
| E | A | E | NT |
| F | A | E | NT |
| G | B | D | E |
| H | B | D | D |
| I | A | D | D |
| J | A | D | C |
| K | A | D | C |
| L | A | D | D |
| M | B | E | E |
| N | A | D | D |
| O | A | D | D |
| P | A | E | D |
| Q | A | E | D |
| R | A | E | D |
| S | B | E | E |
| T | A | D | C |
| U | A | C | C |
| V | A | D | C |
| W | B | E | E |
| X | A | D | D |
| Y | A | D | D |
| Z | A | E | D |
| AA | A | E | D |
| AB | A | E | D |
| AC | B | E | E |
| AD | A | D | C |
| AE | A | C | C |
| AF | A | D | C |
| AG | A | E | E |
| AH | A | C | D |
| AI | B | E | E |
| AJ | A | D | D |
| AK | A | D | D |
| AL | A | D | D |
| AM | A | E | E |
| AN | A | E | E |
| AO | B | E | E |
| AP | A | E | D |
| AQ | A | E | D |
| AR | C | E | E |
| AS | A | E | D |
| AT | A | E | D |
| AU | C | E | E |
| AV | A | E | E |
| AW | C | E | E |

*
A = less than 100 nM
B = 100–250 nM
C = 250–2500 nM
D = greater than 2500 nM
E = Not Active
NT = Not tested

Example B
Evaluation of Test Compound as an Inhibitor of Angiogenesis In vivo The chicken CAM (chick embryo chorioallantoic membrane) model, a standard angiogenesis assay, is used to evaluate the ability of a test compound to inhibit angiogenesis. This model is an established model for evaluation of activity of a test compound to affect formulation of new blood vessels.

A filter disc saturated with a 0.5 µg/ml solution of basic fibroblast growth factor (bFGF) is placed on the CAM of 10 day old chick embryos to induce angiogenesis. Twenty four hours later, 0 to 1 µg of Test Compound, in a total volume of 100 µl of sterile PBS, is injected intravenously into the embryo. Approximately 48 hours later, the embryos are sacrificed and the filter discs and surrounding CAM tissue are excised for analysis. Angiogenesis is quantitated by counting the number of blood vessel branch points within the confined region of the filter [Brooks, P. C., et al, Methods in Molecular Biology 120:257–269 (1999)]. The angiogenic index is defined as the difference in the number of blood vessel branch points between an experimental group and the untreated, control embryos. Each experimental group will contain 8 to 10 chicken embryos.

Example C
Evaluation of Test Compound to Inhibit the Growth of Human Tumor Cells in a Chick Embryo Model A chicken embryo model is used to evaluate the activity of Test Compound to inhibit the growth of human tumor cells in vivo. A single cell suspension of human fibrosarcoma cells (HT 1080), containing $4 \times 10^5$ cells in a total volume of 40 µl, is applied to 10 day old chick embryos as described by Brooks, et al ("Brooks, P. C., et al, "Integrin $\alpha_v\beta_3$ Antagonists Promote Tumor Regression by Inducing Apoptosis of Angiogenic Blood Vessels", Cell 79:1157–1164 (1994)). Twenty-four hours later 0 to 10 µg of Test Compound are injected intravenously into the embryos. Following this single administration of compound, control and treated embryos are incubated for a total of 7 days and then sacrificed. Tumors are excised, trimmed free of surrounding CAM tissue, and weighed. The wet weights for tumors excised in this experiment are tabulated. Each experimental group will contain 10 to 12 chicken embryos.

We claim:

1. A compound of the formula:

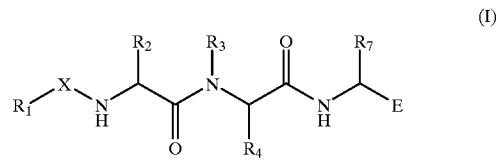

(I)

wherein:
(a) X is selected from the group consisting of —S(O)$_2$—, N(R)—S(O)$_2$—, —(C=O)—, —OC(=O)—, —NH—C(=O)—, —P(O)(R')—, and a direct link, wherein R' is independently hydrogen, alkyl of 1 to 4 carbon atoms, aryl of 6 to 14 carbon atoms or aralkyl of 7 to 16 carbon atoms, with the proviso that when X is —P(O)(R')—, then R' is not hydrogen;
(b) R$_1$ is selected from the group consisting of:
(1) alkyl of 1 to 12 carbon atoms which is optionally substituted with Y$_1$ and/or Y$_2$,
(2) alkyl of 1 to 3 carbon atoms substituted with cycloalkyl of 3 to 8 carbon atoms which is optionally mono-, di- or tri-substituted with Y$_1$, Y$_2$, and/or Y$_3$,
(3) cycloalkyl of 3 to 15 carbon atoms, which is optionally mono-, di-, or tri-substituted on the ring with Y$_1$, Y$_2$, and/or Y$_3$,
(4) heterocycloalkyl of 4 to 10 ring atoms with the ring atoms selected from carbon and heteroatoms, wherein the heteroatoms are selected from the group consisting of oxygen, nitrogen, and $S(O)_i$, wherein i is 0, 1 or 2, which is optionally mono-, di-, or tri-substituted on the ring with $Y_1$, $Y_2$, and/or $Y_3$, (5) heterocyclo of 4 to 10 ring atoms with the ring atoms selected from carbon and heteroatoms, wherein the heteroatoms are selected from the group consisting of oxygen nitrogen, and $S(O)_i$ wherein i is 0, 1, or 2, including,

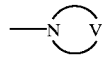

wherein

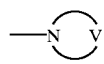

is a 5 to 7 member heterocycle having 3 to 6 ring carbon atoms, where V is —$CH_2$—, —O—, —S(=O)—, —$S(O)_2$— or —S—, which is optionally mono-, di-, or tri-substituted on the ring carbons with $Y_1$, $Y_2$, and/or $Y_3$, (6) alkenyl of 2 to 6 carbon atoms which is optionally substituted with cycloalkyl of 3 to 8 carbon atoms, which is optionally mono-, di-, or tri-substituted on the ring with $Y_1$, $Y_2$, and/or $Y_3$, (7) aryl of 6 to 14 carbon atoms which is optionally mono-, di- or tri-substituted with $Y_1$, $Y_2$, and/or $Y_3$, (8) heteroaryl of 5 to 14 ring atoms with the ring atoms selected from carbon and heteroatoms, wherein the heteroatoms are selected from oxygen, nitrogen, and sulfur, and which is optionally mono-, di- or tri-substituted with $Y_1$, $Y_2$, and/or $Y_3$, (9) aralkyl of 7 to 15 carbon atoms which is optionally substituted on the alkyl chain with hydroxy or halogen and which is optionally mono-, di-, or tri-substituted on the aryl ring with $Y_1$, $Y_2$ and/or $Y_3$,

(10) heteroaralkyl of 5 to 14 ring atoms with the ring atoms selected from carbon and heteroatoms, wherein the heteroatoms are selected from oxygen, nitrogen, and sulfur, which is optionally substituted on the alkyl chain with hydroxy or halogen and optionally mono-, di- or tri-substituted on the ring with $Y_1$, $Y_2$ and/or $Y_3$,

(11) aralkenyl of 8 to 16 carbon atoms which is optionally mono-, di-, or tri-substituted on the aryl ring with $Y_1$, $Y_2$ and/or $Y_3$,

(12) heteroaralkenyl of 5 to 14 ring atoms with the ring atoms selected from carbon and heteroatoms, wherein the heteroatoms are selected from oxygen, nitrogen, and sulfur, and which is optionally mono-, di- or tri-substituted on the ring carbons with $Y_1$, $Y_2$ and/or $Y_3$,

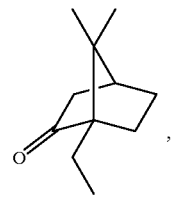

(13)

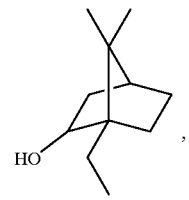

(14)

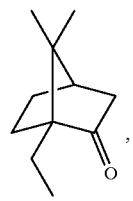

(15)

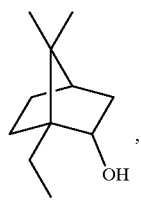

(16)

(17) fused carbocyclic alkyl of 9 to 15 carbon atoms,
(18) difluoromethyl or perfluoroalkyl of 1 to 12 carbon atoms,
(19) perfluoroaryl of 6 to 14 carbon atoms,
(20) perfluoroaralkyl of 7 to 15 carbon atoms, and
(21) hydrogen when X is a direct link; wherein each $Y_1$, $Y_2$, and $Y_3$ is independently selected and is
  (i) selected from the group consisting of halogen, cyano, nitro, tetrazolyl, guanidino, amidino, methylguanidino, —$CF_3$, —$CF_2CF_3$, —$CH(CF_3)_2$, —$C(OH)(CF_3)_2$, —$OCF_3$, —$OCF_2H$, —$OCF_2CF_3$, —$OC(O)NH_2$, —$OC(O)NHZ_1$, —$OC(O)NX_1Z_2$, —$NHC(O)Z_1$, —$NHC(O)NH_2$, —$NHC(O)NZ_1$, —$NHC(O)NZ_1Z_2$, —$C(O)OH$, —$C(O)OZ_1$, —$C(O)NH_2$, —$C(O)NHZ_1$, —$C(O)NZ_1Z_2$, —$P(O)_3H_2$, —$P(O)_3(Z_1)_2$, —$S(O)_3H$, —$S(O)_mZ_1$, —$Z_1$, —$OZ_1$, —OH, —$NH_2$, —$NHZ_1$, —$NZ_1Z_2$, —N-morpholino, and $S(O)_m(CF_2)_qCF_3$, wherein m is 0, 1 or 2, q is an integer from 0 to 5, and $Z_1$ and $Z_2$ are independently selected from the group consisting of alkyl of 1 to 12 carbon atoms, aryl of 6 to 14 carbon atoms, heteroaryl of 5 to 14 ring atoms, aralkyl of 7 to 15 carbon atoms, and heteroaralkyl of 5 to 14 ring atoms, or
  (ii) $Y_1$ and $Y_2$ are selected together to be —$O[C(Z_3)(Z_4)]_rO$— or —$O[C(Z_3)(Z_4)]_{r+1}$—, wherein r is an integer from 1 to 4 and $Z_3$ and $Z_4$ are independently selected from the group consisting of hydrogen, alkyl of 1 to 12 carbon atoms, aryl of 6 to 14 carbon atoms, heteroaryl of 5 to 14 ring atoms, aralkyl of 7 to 15 carbon atoms, and heteroaralkyl of 5 to 14 ring atoms;

(c) $R_2$ is selected from the group consisting of —$CH_3$, —$C_2H_5$, —$(CH_2)_2OH$, —$(CH_2)_2OA_1$, —$CH(R_5)OH$, —$CH(R_5)OA_1$ and —$CH_2NH$—X'—$R_6$ wherein $A_1$ is —C(=O)O$R_6$, —C(=O)$R_6$ or —C(=O)N$R_5R_6$; X' is selected from the group consisting of —S(O)$_2$—, —S(O)$_2$—N(R")—, —(C=O)—, —C(=O)—O—, —C(=O)—NH—, —P(O)(R")—, and a direct link, wherein R" is hydrogen, alkyl of 1 to 4 carbon atoms, aryl of 6 to 14 carbon atoms or aralkyl of 7 to 16 carbon atoms with the proviso that when X' is —P(O)(R")—, then R" is not hydrogen; $R_5$ is selected from the group consisting of:

(1) alkyl of 1 to 4 carbon atoms, optionally substituted with $Y_1$ and/or $Y_2$,
(2) alkyl of 1 to 3 carbon atoms substituted with cycloalkyl of 3 to 6 carbon atoms, which is optionally mono-, di-, or tri-substituted on the ring with $Y_1$, $Y_2$, and/or $Y_3$,
(3) cycloalkyl of 3 to 6 carbon atoms, which is optionally mono-, di-, or trisubstituted on the ring with $Y_1$, $Y_2$, and/or $Y_3$,
(4) heterocycloalkyl of 4 to 6 ring atoms with the ring atoms selected from carbon and heteroatoms, wherein the heteroatoms are selected from the group consisting of oxygen, nitrogen, and S(O)$_i$, wherein i is 0, 1 or 2, which is optionally mono-, di-, or tri-substituted on the ring with $Y_1$, $Y_2$ and/or $Y_3$,
(5) heterocyclo of 4 to 6 ring atoms with the ring atoms selected from carbon and heteroatoms, wherein the heteroatoms are selected from the group consisting of oxygen, nitrogen, and S(O)$_i$, wherein i is 0, 1, or 2, including

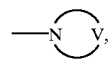

wherein

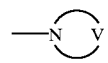

is a 5 to 6 member heterocycle having 3 to 5 ring carbon atoms, where V is —$CH_2$—, —O—, —S(=O)—, —S(O)$_2$— or —S—, which is optionally mono-, di-, or tri-substituted on the ring carbons with $Y_1$, $Y_2$ and/or $Y_3$,
(6) alkenyl of 2 to 6 carbon atoms which is optionally substituted with cycloalkyl of 3 to 6 carbon atoms, which is optionally mono-, di-, or tri-substituted on the ring with $Y_1$, $Y_2$ and/or $Y_3$,
(7) phenyl which is optionally mono-, di- or tri-substituted with $Y_1$, $Y_2$ and/or $Y_3$,
(8) heteroaryl of 5 to 6 ring atoms with the ring atoms selected from carbon and heteroatoms, wherein the heteroatoms are selected from oxygen, nitrogen, and sulfur, and which is optionally mono-, di- or tri-substituted with $Y_1$, $Y_2$ and/or $Y_3$,
(9) alkyl of 1 to 4 carbon atoms substituted with phenyl and which is optionally mono-, di-, or tri-substituted on the phenyl ring with $Y_1$, $Y_2$ and/or $Y_3$,

(10) heteroaralkyl of 5 to 6 ring atoms with the ring atoms selected from carbon and heteroatoms, wherein the heteroatoms are selected from oxygen, nitrogen, and sulfur, and which is optionally substituted on the alkyl chain with hydroxy or halogen and optionally mono-, di- or tri-substituted on the ring with $Y_1$, $Y_2$ and/or $Y_3$,
(11) aralkenyl of 8 to 12 carbon atoms which is optionally mono-, di-, or tri-substituted on the aryl ring with $Y_1$, $Y_2$ and/or $Y_3$,
(12) heteroalkenyl of 5 to 6 ring atoms with the ring atoms selected from carbon and heteroatoms, wherein the heteroatoms are selected from oxygen, nitrogen, and sulfur, and which is optionally mono-, di- or tri-substituted on the ring carbons with $Y_1$, $Y_2$ and/or $Y_3$, and
(13) hydrogen; and $R_6$ is selected from the group consisting of:
(1) alkyl of 1 to 12 carbon atoms, optionally substituted with $Y_1$ and/or $Y_2$,
(2) alkyl of 1 to 3 carbon atoms substituted with cycloalkyl of 3 to 8 carbon atoms, which is optionally mono-, di-, or tri-substituted on the ring with $Y_1$, $Y_2$ and/or $Y_3$,
(3) cycloalkyl of 3 to 15 carbon atoms, which is optionally mono-, di-, or trisubstituted on the ring with $Y_1$, $Y_2$ and/or $Y_3$,
(4) heterocycloalkyl of 4 to 10 ring atoms with the ring atoms selected from carbon and heteroatoms, wherein the heteroatoms are selected from the group consisting of oxygen, nitrogen, and S(O)$_i$, wherein i is 0, 1 or 2, which is optionally mono-, di-, or tri-substituted on the ring with $Y_1$, $Y_2$ and/or $Y_3$,
(5) heterocyclo of 4 to 10 ring atoms with the ring atoms selected from carbon and heteroatoms, wherein the heteroatoms are selected from the group consisting of oxygen, nitrogen, and S(O)$_i$, wherein i is 0, 1, or 2, including

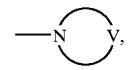

wherein

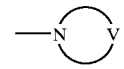

is a 5 to 7 member heterocycle having 3 to 6 ring carbon atoms, where V is —$CH_2$—, —O—, —S(=O)—, —S(O)$_2$— or —S—, which is optionally mono-, di-, or tri-substituted on the ring carbons with $Y_1$, $Y_2$ and/or $Y_3$,
(6) aryl of 6 to 14 carbon atoms which is optionally mono-, di- or tri-substituted with $Y_1$, $Y_2$ and/or $Y_3$,
(7) heteroaryl of 5 to 14 ring atoms with the ring atoms selected from carbon and heteroatoms, wherein the heteroatoms are selected from oxygen, nitrogen, and sulfur, and which is optionally mono-, di- or tri-substituted with $Y_1$, $Y_2$ and/or $Y_3$,
(8) aralkyl of 7 to 15 carbon atoms which is optionally mono-, di-, on tri-substituted on the aryl ring with $Y_1$, $Y_2$ and/or $Y_3$, (9) heteroaralkyl of 5 to 14 ring atoms with the ring atoms selected from carbon and heteroatoms, wherein the heteroatoms are selected from oxygen, nitrogen, and sulfur, and which is optionally substituted on the alkyl chain with hydroxy or halogen and optionally mono-, di- or tri-substituted on the ring with $Y_1$, $Y_2$ and/or $Y_3$, and

(10) hydrogen, with the proviso that $R_6$ is not hydrogen when $A_1$ is —C(=O)OR$_6$;

(d) $R_3$ is selected from H and methyl, or $R_3$ and $R_4$ are selected together as set forth in (f);

(e) the carbon bearing $R_4$ is of the S configuration and is selected from the group consisting of H, —CH$_2$—S—CH$_3$, —CH$_2$OH, —CH$_2$CN, lower alkyl of 1 to 3 carbon atoms, —CH$_2$C≡CH, —CH$_2$CH=CH$_2$ and —CH=CH$_2$ or $R_3$ and $R_4$ are selected together as set forth in (f);

(f) alternatively, the carbon bearing $R_4$ is of the S configuration and $R_3$ and $R_4$ are selected together to give a group at P2 selected from the group consisting of prolyl, pipecolyl, azetidine-2-carbonyl, 4-hydroxyprolyl, 3-hydroxyprolyl, 3,4-methanoprolyl and 3,4-dehydroprolyl;

(g) $R_7$ is hydrogen or alkyl of 1 to 4 carbon atoms; and (h) E is selected from

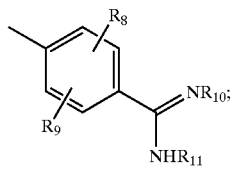
(1)

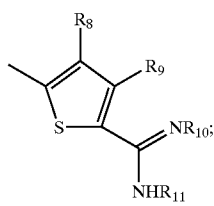
(2)

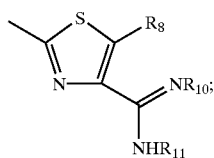
(3)

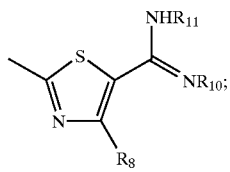
(4)

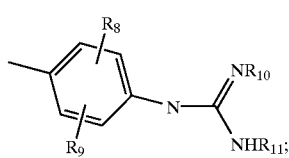
(5)

-continued

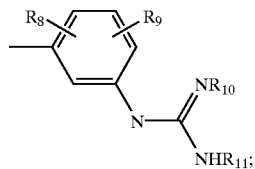
(6)

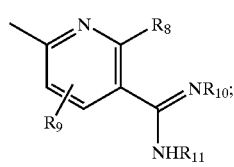
(7)

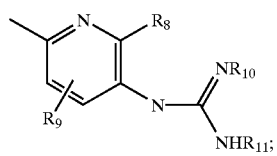
(8)

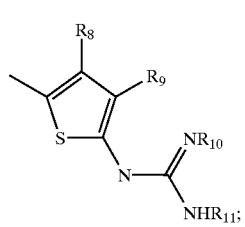
(9)

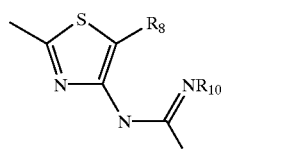
(10)

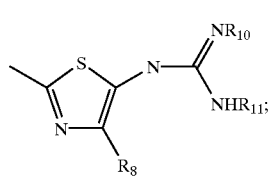
(11)

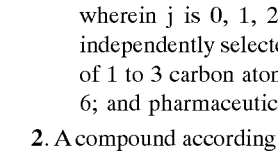

wherein $R_8$ and $R_9$ are independently selected from hydrogen, hydroxy, halogen, alkyl of 1 to 4 carbon atoms, alkyl of 1 to 4 carbon atoms substituted with alkoxy of 1 to 4 carbon atoms, alkoxy of 1 to 6 carbon atoms, and trifluoromethyl; $R_{10}$ and $R_{11}$ are independently hydrogen, hydroxy, alkoxy of 1 to 3 carbon atoms, trihydrocarbylsilyl of 3 to 16 carbon atoms, alkyl of 1 to 3 carbon atoms or —C(=O)R$_{12}$; $R_{11}$ is hydrogen or alkyl of 1 to 3 carbon atoms with the proviso that $R_{10}$ and $R_{11}$ are not both hydroxy or alkoxy; $R_{12}$ is hydrogen, alkyl of 1 to 6 carbon atoms, alkoxy of 1 to 6 carbon atoms or (CF$_2$)$_j$CF$_3$ wherein j is 0, 1, 2 or 3; each of $R_{13}$ and $R_{14}$ is independently selected from hydrogen or lower alkyl of 1 to 3 carbon atoms; and t is an integer from 0 to 6; and pharmaceutically acceptable salts thereof.

2. A compound according to claim 1 wherein E is selected from the group consisting of

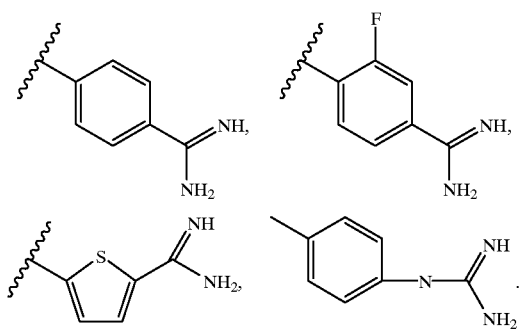

3. A compound according to claim 2 wherein X is —S(O₂)— or —O—C(=O)—.

4. A compound according to claim 3 wherein R₂ is —CH₃ or —CH (R₅) OH.

5. A compound according to claim 4 wherein R₅ is hydrogen or alkyl optionally substituted with Y₁.

6. A compound according to claim 5 wherein R₂ is —CH₂OH or —CH(CH₃)OH.

7. A compound according to claim 6 wherein R₂ is —CH(CH₃)OH and both the carbon bearing R₂ (alpha carbon) and the methyl group of R₂ (beta carbon) have the R configuration.

8. A compound according to claim 6 wherein R₃ is hydrogen.

9. A compound according to claim 8 wherein R₄ is methyl or propargyl.

10. A compound according to claim 6 wherein R₃ and R₄ are selected together to give a group at P₂ selected from the group consisting of prolyl, pipecolyl, azetidine-2-carbonyl, 4-hydroxyprolyl, 3-hydroxyprolyl, 3,4-methanoprolyl and 3,4-dehydroprolyl.

11. A compound according to claim 10 wherein R₃ and R₄ are selected together to give a group at P₂ selected from the group consisting of prolyl, 4-cis-hydroxyprolyl, 3,4-dehydroprolyl, 3,4-methanoprolyl and azetidine-2-carbonyl.

12. A compound according to claim 4 wherein R₅ is H.

13. A compound according to claim 1 wherein X is selected from —S(O)₂—, —OC(=O)—, —NH—C(=O)— and a direct link.

14. A compound according to claim 13 wherein X is —S(O)₂— or —OC(=O)—.

15. A compound according to claim 14 wherein R₁, is selected from phenyl, benzyl, 2-phenylethyl, isobutyl, n-butyl, 3-phenylpropyl; 4-chlorobenzyl, 3-chlorobenzyl and 2-fluorobenzyl.

16. A compound according to claim 15 wherein R₁—X— is selected from phenyl-S(O)₂—, benzyl-S(O)₂—, 2-phenylethyl-S(O)₂—, 3-phenylpropyl-S(O)₂—, n-butyl-S(O)₂—, benzyl-OC(=O)—, isobutyl-OC(=O)—, 4-chlorobenzyl-S(O)₂—, 3-chlorobenzyl-S(O)₂— and 2-fluorobenzyl-S(O)₂—.

17. A compound according to claim 16 wherein R₂ is selected to give a D-seryl group at P3.

18. A compound according to claim 17 wherein E is 4-amidinophenyl, 4-guanidinophenyl or 5-(2-amidinothienyl).

19. A compound according to claim 18 wherein (i) R₃ and R₄ are selected together to give a group at P2 selected from the group consisting of prolyl, azetidine-2-carbonyl, 3,4-methanoprolyl and 3,4-dehydroprolyl or (ii) R₃ is hydrogen and R₄ is methyl.

20. A compound according to claim 16 wherein E is 4-amidinophenyl, 4-guanidinophenyl or 5(2-amidinothienyl).

21. A compound according to claim 20 wherein (i) R₃ and R₄ are selected together to give a group at P2 selected from the group consisting of prolyl, azetidine-2-carbonyl, 3,4-methanoprolyl and 3,4-dehydroprolyl or (ii) R₃ is hydrogen and R₄ is methyl.

22. A compound according to claim 16 wherein (i) R₃ and R₄ are selected together to give a group at P2 selected from the group consisting of prolyl, azetidine-2-carbonyl, 3,4-methanoprolyl, and 3,4-dehydroprolyl or (ii) R₃ is hydrogen and R₄ is methyl.

23. A compound according to claim 1 wherein R₂ is selected from —CH₂NH(X')(R₆) and —CH(R₅)OH.

24. A compound according to claim 23 wherein R₅ is selected from hydrogen, alkyl optionally substituted with Y₁ and alkyl of 1 to 4 carbon atoms substituted with phenyl and which is optionally mono-, di- or tri-substituted with Y₁, Y₂ and/or Y₃.

25. A compound according to claim 24 wherein R₂ is selected to give a group at P3 selected from D-seryl, (R,R)D-allothreonyl, D-2-aminobutyryl, N-β-methyloxycarbonyl-D-2,3-diaminopropionyl, N-β-(2-phenylethylcarbonyl)-D-2,3-diaminopropionyl, and N-β-benzyloxycarbonyl-D-2,3-diaminopropionyl.

26. A compound according to 25 wherein the group at P3 is D-seryl or (R,R)D-allothreonyl.

27. A compound according to claim 1 wherein R₃ is hydrogen.

28. A compound according to claim 1 wherein R₄ is methyl, vinyl, allyl or propargyl.

29. A compound according to claim 1 wherein R₃ and R₄ are selected together to give a group at P2 selected from prolyl, pipecolyl, azetidine-2-carbonyl, 4-hydroxyprolyl, 3-hydroxyprolyl, 3,4-methanoprolyl, and 3,4-dehydroprolyl.

30. A compound according to claim 29 wherein R₃ and R₄ are selected together to give a group at P2 selected from prolyl, 4-cis-hydroxyprolyl, 3,4-dehydroprolyl, 3,4-methanoprolyl and azetidine-2-carbonyl.

31. A compound according to claim 30 wherein R₂ is selected to give a group at P3 selected from D-seryl and (R,R) D-allothreonyl.

32. A compound according to claim 1 wherein R₂ is selected to give a group at P3 selected from D-seryl and (R,R)-D-allothreonyl R₃ is hydrogen and R₄ is methyl.

33. A compound according to claim 1 wherein R₃ and R₄ are selected together to give a group at P2 selected from prolyl, azetidine-2-carbonyl, 3,4-methanoprolyl and 3,4-dehydroprolyl.

34. A compound according to claim 6 wherein R₂ is —CH₂OH and the carbon bearing R₂ (alpha carbon) has the R configuration.

35. A compound according to claim 1 wherein R₂ is —(CH₂)₂OA₁ or —CH (R₅) OA₁.

36. A compound according to claim 35 wherein R₂ is —CH(R₅)OA₁.

37. A compound according to claim 36 wherein R₅ is selected from hydrogen, alkyl optionally substituted with Y₁, and alkyl of 1 to 4 carbon atoms substituted with phenyl and which is optionally mono-, di- or tri-substituted with Y₁, Y₂ and/or Y₃.

38. A compound according to claim 37 wherein R₂ is selected to give a group at P3 selected from acyl and carbonate esters of D-seryl.

39. A compound according to claim 38 wherein R₃ is hydrogen.

40. A compound according to claim 39 wherein R₄ is methyl, vinyl, allyl or propargyl.

41. A compound according to claim 38 wherein $R_3$ and $R_4$ are selected together to give a group at P2 selected from prolyl, pipecolyl, azetidine-2-carbonyl, 4-hydroxyprolyl, 3-hydroxyprolyl, 3,4-methanoprolyl and 3,4-dehydroprolyl.

42. A compound according to claim 1 wherein $R_2$ is selected to give a group at P3 selected from acyl and carbonate esters of D-seryl.

43. A compound according to claim 42 wherein $R_3$ is hydrogen and $R_4$ is methyl.

44. A compound according to claim 42 wherein $R_3$ and $R_4$ are selected together to give a group at P2 selected from prolyl, azetidine-2-carbonyl, 3,4-methanoprolyl and 3,4-dehydroprolyl.

45. A compound according to claim 1 wherein $R_2$ is selected to give a group at P3 selected from acyl and carbonate esters of D-seryl.

46. a compound according to claim 1 which is selected from the group consisting of

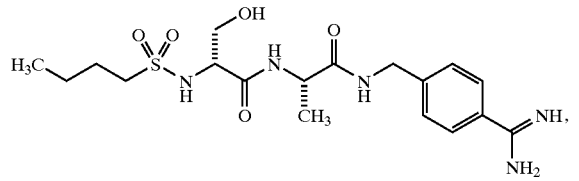
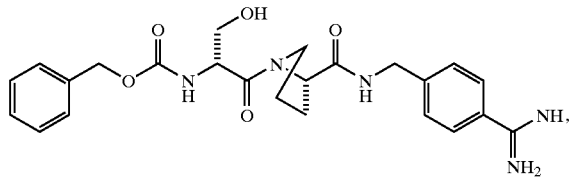
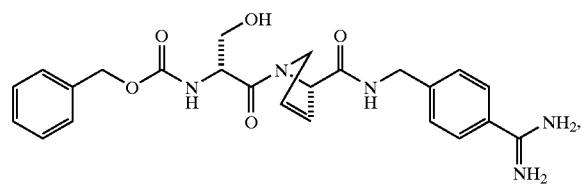
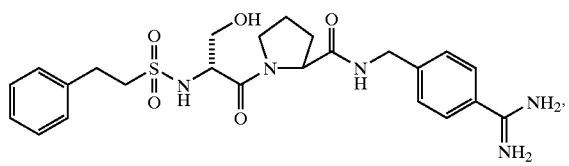
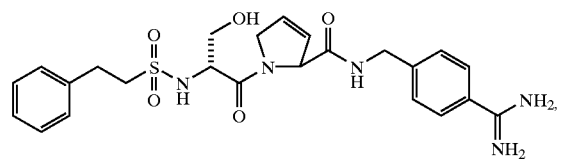
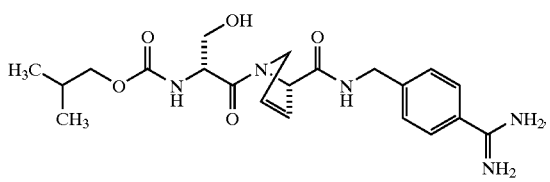
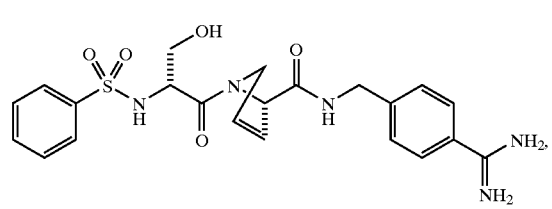
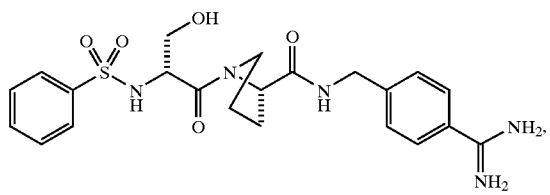
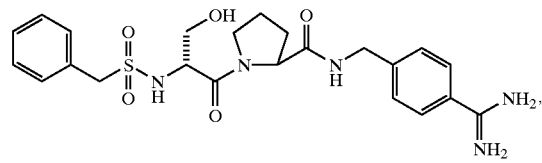
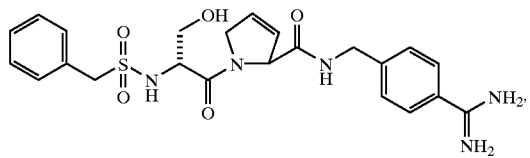
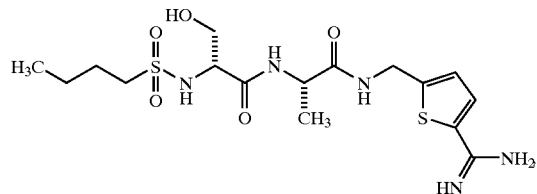
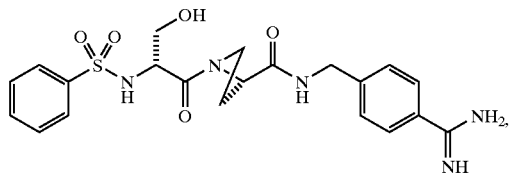
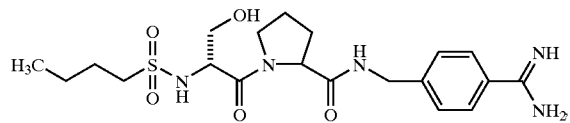
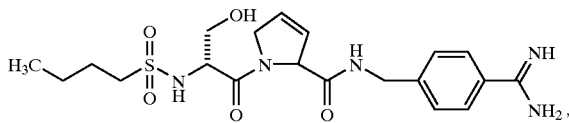
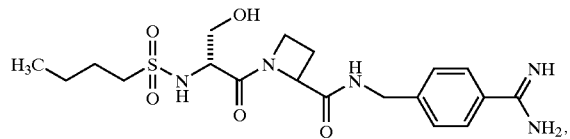
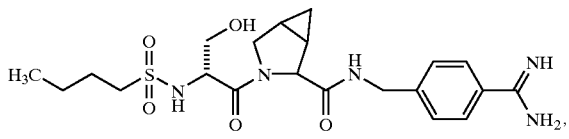

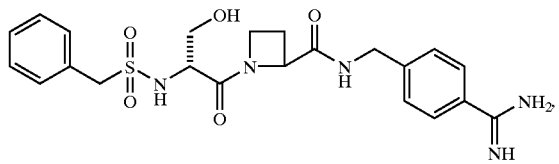
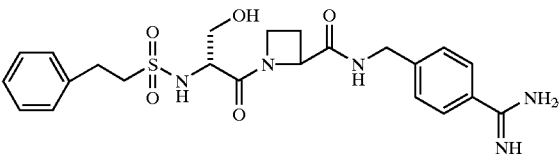
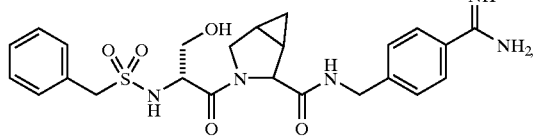
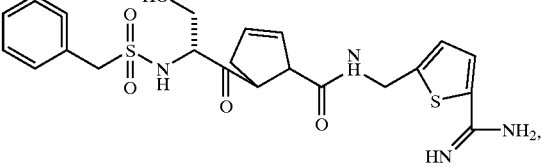
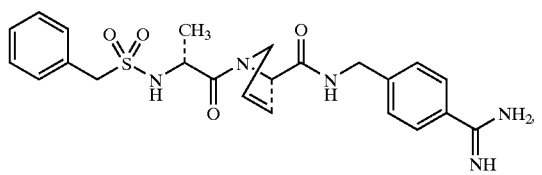
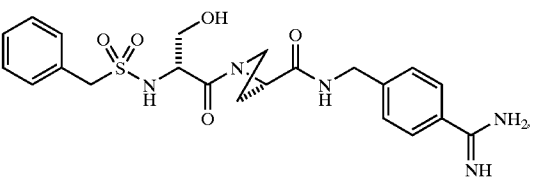
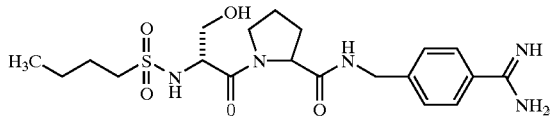
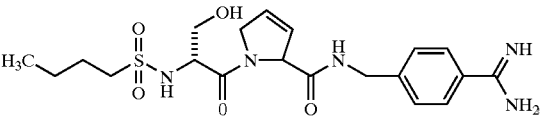
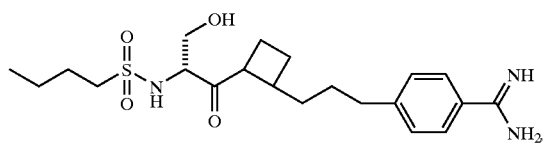
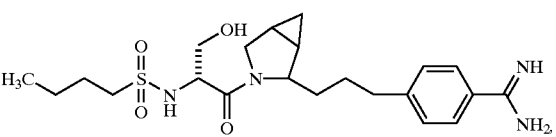
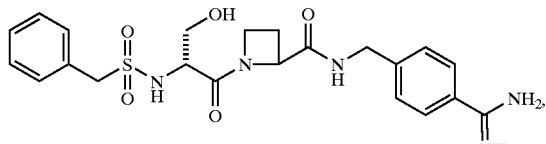
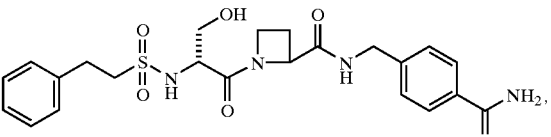
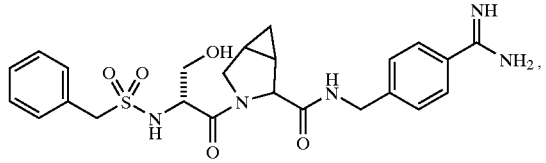
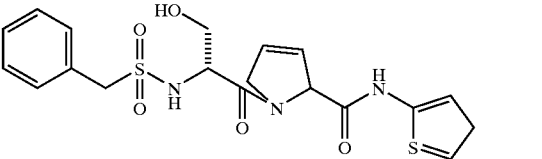
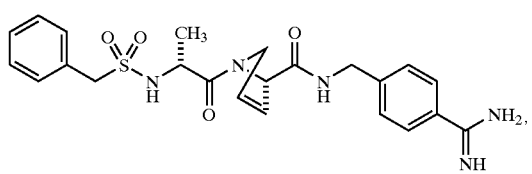
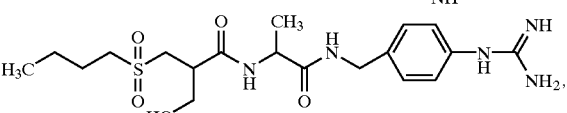
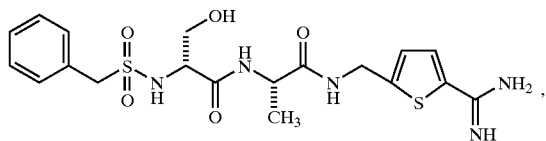
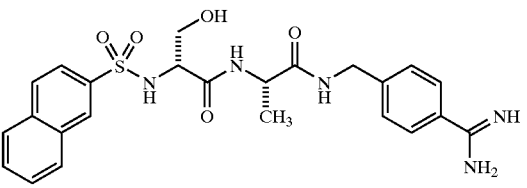
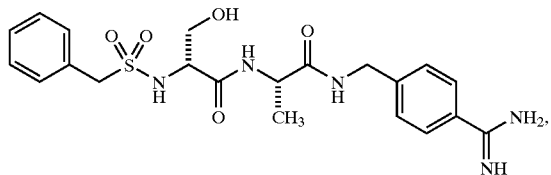
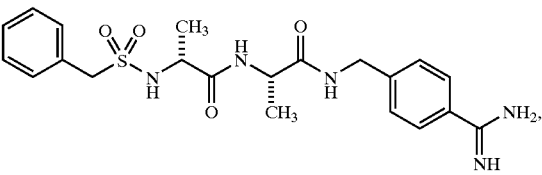

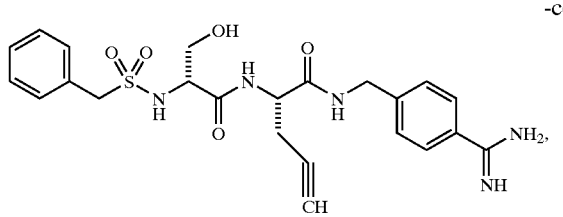
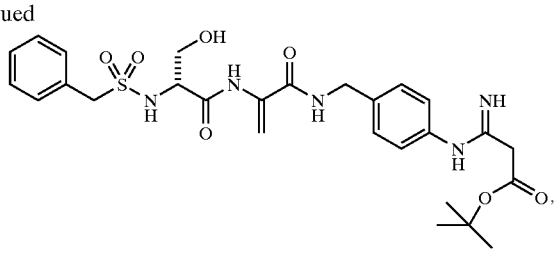
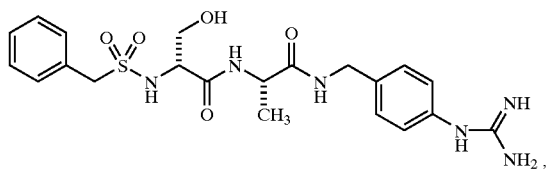
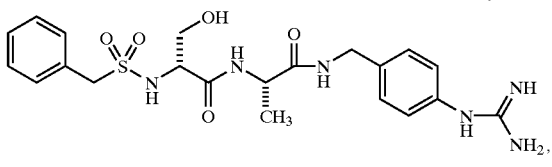
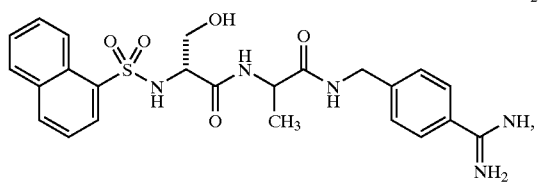
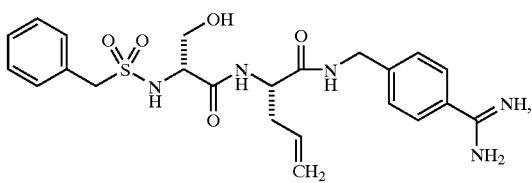
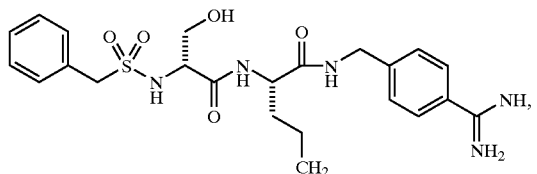
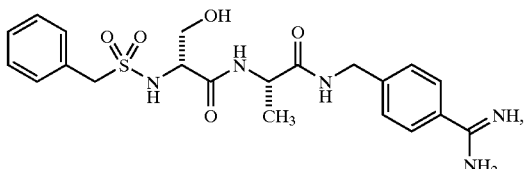
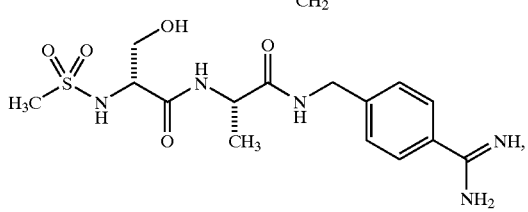
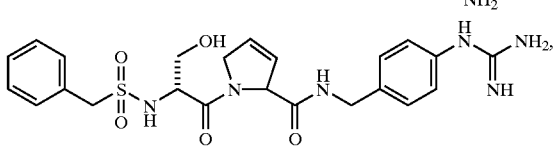
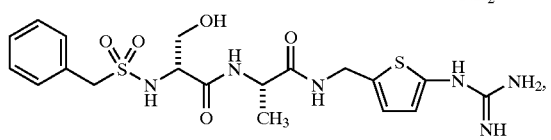
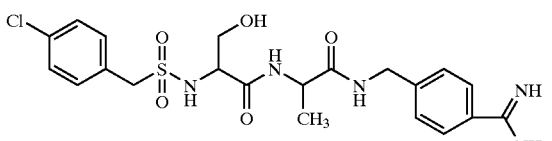
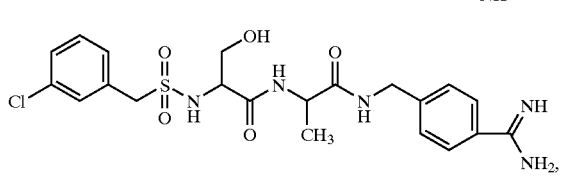
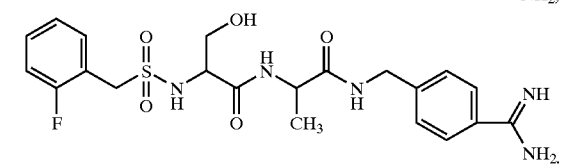

and

47. A composition comprising a compound according to claim 1 and a pharmaceutically acceptable carrier.

48. A composition comprising a compound according to claim 5 and a pharmaceutically acceptable carrier.

49. A composition comprising a compound according to claim 16 and a pharmaceutically acceptable carrier.

50. A composition comprising a compound according to claim 26 and a pharmaceutically acceptable carrier.

51. A composition comprising a compound according to claim 31 and a pharmaceutically acceptable carrier.

52. A composition comprising a compound according to claim 38 and a pharmaceutically acceptable carrier.

53. A composition comprising a compound according to claim 40 and a pharmaceutically acceptable carrier.

54. A composition comprising a compound according to claim 41 and a pharmaceutically acceptable carrier.

55. A composition comprising a compound according to claim 43 and a pharmaceutically acceptable carrier.

56. A composition comprising a compound according to claim 44 and a pharmaceutically acceptable carrier.

57. A composition comprising a compound according to claim 46 and a pharmaceutically acceptable carrier.

58. A method of inhibiting urokinase comprising administering to a mammal in need thereof a compound according to claim 1 for a time and under conditions effective to inhibit urokinase.

59. A method of inhibiting urokinase comprising administering to a mammal in need thereof a compound according to claim 5 for a time and under conditions effective to inhibit urokinase.

60. A method of inhibiting urokinase comprising administering to a mammal in need thereof a compound according to claim 16 for a time and under conditions effective to inhibit urokinase.

61. A method of inhibiting urokinase comprising administering to a mammal in need thereof a compound according to claim 26 for a time and under conditions effective to inhibit urokinase.

62. A method of inhibiting urokinase comprising administering to a mammal in need thereof a compound according to claim 31 for a time and under conditions effective to inhibit urokinase.

63. A method of inhibiting urokinase comprising administering to a mammal in need thereof a compound according to claim 38 for a time and under conditions effective to inhibit urokinase.

64. A method of inhibiting urokinase comprising administering to a mammal in need thereof a compound according to claim 40 for a time and under conditions effective to inhibit urokinase.

65. A method of inhibiting urokinase comprising administering to a mammal in need thereof a compound according to claim 41 for a time and under conditions effective to inhibit urokinase.

66. A method of inhibiting urokinase comprising administering to a mammal in need thereof a compound according to claim 43 for a time and under conditions effective to inhibit urokinase.

67. A method of inhibiting urokinase comprising administering to a mammal in need thereof a compound according to claim 44 for a time and under conditions effective to inhibit urokinase.

68. A method of inhibiting urokinase comprising administering to a mammal in need thereof a compound according to claim 46 for a time and under conditions effective to inhibit urokinase.

69. A method of inhibiting angiogenesis comprising administering to a mammal in need thereof a compound according to claim 1 for a time and under conditions effective to inhibit urokinase.

70. A method of inhibiting angiogenesis comprising administering to a mammal in need thereof a compound according to claim 5 for a time and under conditions effective to inhibit urokinase.

71. A method of inhibiting angiogenesis comprising administering to a mammal in need thereof a compound according to claim 16 for a time and under conditions effective to inhibit urokinase.

72. A method of inhibiting angiogenesis comprising administering to a mammal in need thereof a compound according to claim 26 for a time and under conditions effective to inhibit urokinase.

73. A method of inhibiting angiogenesis comprising administering to a mammal in need thereof a compound according to claim 31 for a time and under conditions effective to inhibit urokinase.

74. A method of inhibiting angiogenesis comprising administering to a mammal in need thereof a compound according to claim 38 for a time and under conditions effective to inhibit urokinase.

75. A method of inhibiting angiogenesis comprising administering to a mammal in need thereof a compound according to claim 40 for a time and under conditions effective to inhibit urokinase.

76. A method of inhibiting angiogenesis comprising administering to a mammal in need thereof a compound according to claim 41 for a time and under conditions effective to inhibit urokinase.

77. A method of inhibiting angiogenesis comprising administering to a mammal in need thereof a compound according to claim 43 for a time and under conditions effective to inhibit urokinase.

78. A method of inhibiting angiogenesis comprising administering to a mammal in need thereof a compound according to claim 44 for a time and under conditions effective to inhibit urokinase.

79. A method of inhibiting angiogenesis comprising administering to a mammal in need thereof a compound according to claim 46 for a time and under conditions effective to inhibit urokinase.

80. A method of inhibiting growth of tumor cells comprising administering to a mammal in need thereof a compound according to claim 1 for a time and under conditions effective to inhibit urokinase.

81. A method of inhibiting growth of tumor cells comprising administering to a mammal in need thereof a compound according to claim 5 for a time and under conditions effective to inhibit urokinase.

82. A method of inhibiting growth of tumor cells comprising administering to a mammal in need thereof a compound according to claim 16 for a time and under conditions effective to inhibit urokinase.

83. A method of inhibiting growth of tumor cells comprising administering to a mammal in need thereof a compound according to claim 26 for a time and under conditions effective to inhibit urokinase.

84. A method of inhibiting growth of tumor cells comprising administering to a mammal in need thereof a compound according to claim 31 for a time and under conditions effective to inhibit urokinase.

85. A method of inhibiting growth of tumor cells comprising administering to a mammal in need thereof a compound according to claim 38 for a time and under conditions effective to inhibit urokinase.

86. A method of inhibiting growth of tumor cells comprising administering to a mammal in need thereof a compound according to claim 40 for a time and under conditions effective to inhibit urokinase.

87. A method of inhibiting growth of tumor cells comprising administering to a mammal in need thereof a compound according to claim 41 for a time and under conditions effective to inhibit urokinase.

88. A method of inhibiting growth of tumor cells comprising administering to a mammal in need thereof a compound according to claim 43 for a time and under conditions effective to inhibit urokinase.

89. A method of inhibiting growth of tumor cells comprising administering to a mammal in need thereof a compound according to claim 44 for a time and under conditions effective to inhibit urokinase.

90. A method of inhibiting growth of tumor cells comprising administering to a mammal in need thereof a compound according to claim 46 for a time and under conditions effective to inhibit urokinase.

* * * * *